US010746732B2

(12) United States Patent
Rajasekaran et al.

(10) Patent No.: US 10,746,732 B2
(45) Date of Patent: Aug. 18, 2020

(54) METHODS, SYSTEMS, AND ARRAYS FOR BIOMOLECULAR ANALYSIS

(71) Applicant: Vibrant Holdings, LLC, San Carlos, CA (US)

(72) Inventors: John J. Rajasekaran, Hillsborough, CA (US); Vasanth Jayaraman, San Mateo, CA (US); Tianhao Wang, San Mateo, CA (US); Kang Bei, San Mateo, CA (US); Hari Krishnan Krishnamurthy, San Mateo, CA (US)

(73) Assignee: Vibrant Holdings, LLC, San Carlos, CA (US)

( * ) Notice: Subject to any disclaimer, the term of this patent is extended or adjusted under 35 U.S.C. 154(b) by 0 days.

(21) Appl. No.: 15/977,951

(22) Filed: May 11, 2018

(65) Prior Publication Data

US 2019/0018006 A1    Jan. 17, 2019

Related U.S. Application Data

(63) Continuation of application No. 14/432,200, filed as application No. PCT/US2013/062773 on Sep. 30, 2013, now Pat. No. 10,006,909, which is a continuation-in-part of application No. PCT/US2013/025190, filed on Feb. 7, 2013.

(60) Provisional application No. 61/707,758, filed on Sep. 28, 2012, provisional application No. 61/732,221, filed on Nov. 30, 2012, provisional application No. 61/765,584, filed on Feb. 15, 2013, provisional application No. 61/805,884, filed on Mar. 27, 2013, provisional application No. 61/866,512, filed on Aug. 15, 2013, provisional application No. 61/726,515, filed on Nov. 14, 2012, provisional application No. 61/761,347, filed on Feb. 6, 2013.

(51) Int. Cl.
| | |
|---|---|
| *G01N 33/543* | (2006.01) |
| *G01N 35/00* | (2006.01) |
| *C40B 40/10* | (2006.01) |
| *C40B 40/06* | (2006.01) |
| *G01N 35/10* | (2006.01) |

(52) U.S. Cl.
CPC ....... *G01N 33/54366* (2013.01); *C40B 40/06* (2013.01); *C40B 40/10* (2013.01); *G01N 33/54386* (2013.01); *G01N 35/00029* (2013.01); *G01N 35/00069* (2013.01); *G01N 35/0099* (2013.01); *G01N 2035/00158* (2013.01); *G01N 2035/00168* (2013.01); *G01N 2035/00326* (2013.01); *G01N 2035/1034* (2013.01)

(58) Field of Classification Search
CPC ..... G01N 33/54366; C40B 40/06; B01J 19/00
See application file for complete search history.

(56) References Cited

U.S. PATENT DOCUMENTS

| | | | |
|---|---|---|---|
| 5,069,996 A | * | 12/1991 | Rogler ............... G03F 7/022 430/165 |
| 5,143,854 A | | 9/1992 | Pirrung et al. |
| 5,240,811 A | | 8/1993 | Taylor et al. |
| 5,310,687 A | | 5/1994 | Bard et al. |
| 5,866,434 A | | 2/1999 | Massey et al. |
| 5,919,523 A | | 7/1999 | Sundberg et al. |
| 6,017,696 A | | 1/2000 | Heller |
| 6,040,138 A | | 3/2000 | Lockhart et al. |
| 6,083,697 A | | 7/2000 | Beecher et al. |
| 6,140,045 A | | 10/2000 | Wohlstadter et al. |
| 6,319,726 B1 | | 11/2001 | Schuppan et al. |
| 6,506,558 B1 | | 1/2003 | Fodor et al. |
| 6,521,181 B1 | | 2/2003 | Northrup et al. |
| 6,943,034 B1 | | 9/2005 | Winkler et al. |
| 7,510,841 B2 | | 3/2009 | Stuelpnagel et al. |
| 7,544,638 B2 | | 6/2009 | Gao et al. |
| 8,128,908 B2 | | 3/2012 | Santra et al. |
| 9,417,236 B2 | | 8/2016 | Rajasekaran et al. |
| 10,006,909 B2 | | 6/2018 | Rajasekaran et al. |
| 10,040,818 B2 | | 8/2018 | Jayaraman et al. |
| 2002/0076834 A1 | | 6/2002 | Detlef et al. |
| 2002/0086319 A1 | | 7/2002 | Ellson et al. |
| 2003/0068446 A1 | | 4/2003 | Mirkin et al. |
| 2003/0082294 A1 | | 5/2003 | Bruhn et al. |
| 2003/0124029 A1 | | 7/2003 | Webb et al. |

(Continued)

FOREIGN PATENT DOCUMENTS

| | | |
|---|---|---|
| CN | 103675291 A | 3/2014 |
| JP | H05-294995 A | 11/1993 |

(Continued)

OTHER PUBLICATIONS

Alawode, O. E. et al., "Clean Photodecompositionof 1-Methyl-4-Phenyl-1HTetrazole-5(4H)-Thiones to Carbodiimides Proceeds via a Biradical," The Journal of Organic Chemistry, Jan. 7, 2011, pp. 216-222, vol. 76, No. 1.

Arimitsu K et al., "Development of Highly Sensitive Photoreactive Materials Utilizig Photobase-generating Reactions and Base Proliferation Reactions", Journal of Synthetic Organic Chemistry Japan, Jan. 1, 2012, pp. 508-516, vol. 70(5), Yuki Gosei Kagaku Kaokai, Tokyo, JP (with English Abstract).

Beyer et al. (Dec. 21, 2007) Science vol. 318 p. 1888 Supporting Online Material, 6 Pages.

(Continued)

*Primary Examiner* — Narayan K Bhat
(74) *Attorney, Agent, or Firm* — Goodwin Procter LLP

(57) ABSTRACT

Disclosed herein are formulations, substrates, and arrays. Also disclosed herein are methods for manufacturing and using the formulations, substrates, and arrays. Also disclosed are methods for identifying peptide sequences useful for diagnosis and treatment of disorders, and methods for using the peptide sequences for diagnosis and treatment of disorders, e.g., celiac disorder. In certain embodiments, substrates and arrays comprise a porous layer for synthesis and attachment of polymers or biomolecules.

18 Claims, 59 Drawing Sheets

Specification includes a Sequence Listing.

(56) References Cited

U.S. PATENT DOCUMENTS

| | | |
|---|---|---|
| 2003/0148401 A1 | 8/2003 | Agrawal et al. |
| 2003/0228605 A1 | 12/2003 | Sloostra et al. |
| 2004/0038388 A1 | 2/2004 | Yamamoto et al. |
| 2005/0221351 A1 | 10/2005 | Ryu |
| 2005/0244863 A1 | 11/2005 | Mir |
| 2005/0260611 A1 | 11/2005 | Wang et al. |
| 2006/0088863 A1 | 4/2006 | Yamamoto et al. |
| 2006/0172340 A1 | 8/2006 | Wohlstadter et al. |
| 2007/0122841 A1 | 5/2007 | Rajasekaran et al. |
| 2007/0122842 A1 | 5/2007 | Rajasekaran et al. |
| 2007/0154946 A1 | 7/2007 | Rajasekaran et al. |
| 2007/0231794 A1 | 10/2007 | Dill et al. |
| 2008/0108149 A1 | 5/2008 | Sundararajan et al. |
| 2009/0311727 A1 | 12/2009 | Watkins et al. |
| 2009/0325816 A1 | 12/2009 | Mirkin et al. |
| 2010/0028559 A1 | 2/2010 | Yan et al. |
| 2010/0093554 A1 | 4/2010 | Chu |
| 2010/0120630 A1 | 5/2010 | Huang et al. |
| 2010/0240555 A1 | 9/2010 | Sundararajan et al. |
| 2010/0245057 A1 | 9/2010 | Chamarti et al. |
| 2011/0097762 A1 | 4/2011 | Gao et al. |
| 2011/0190210 A1 | 8/2011 | Adini et al. |
| 2011/0281766 A1 | 11/2011 | Cooper |
| 2011/0293644 A1 | 12/2011 | Anderson et al. |
| 2011/0303027 A1 | 12/2011 | Shirazi et al. |
| 2012/0172309 A1 | 7/2012 | Dal Farra et al. |
| 2012/0183981 A1 | 7/2012 | Norman et al. |
| 2012/0245057 A1 | 9/2012 | Albert et al. |
| 2014/0072963 A1 | 3/2014 | Qin |
| 2017/0168047 A1 | 6/2017 | Aghvanyan et al. |
| 2019/0366291 A1 | 12/2019 | Rajasekaran et al. |

FOREIGN PATENT DOCUMENTS

| | | |
|---|---|---|
| JP | H06-500308 A | 1/1994 |
| JP | 2002-500362 A | 1/2002 |
| JP | 2002-502698 A | 1/2002 |
| JP | 2002-525577 A | 8/2002 |
| JP | 2003-517149 A | 5/2003 |
| JP | 2003-523348 A | 8/2003 |
| JP | 2003-342354 A | 12/2003 |
| JP | 2005-512032 A | 4/2005 |
| JP | 2005-513999 A | 5/2005 |
| JP | 2005-521032 A | 7/2005 |
| JP | 2005-264156 A | 9/2005 |
| JP | 2005-530983 A | 10/2005 |
| JP | 2007-504462 A | 3/2007 |
| JP | 2008-170449 A | 7/2008 |
| JP | 2009-075131 A | 4/2009 |
| JP | 2009-534200 A | 9/2009 |
| JP | 2009-534200 A | 9/2009 |
| JP | 2010-507099 A | 3/2010 |
| JP | 2010-215816 A | 9/2010 |
| JP | 2011-017711 A | 1/2011 |
| JP | 2011-519168 A | 6/2011 |
| JP | 2011-234723 A | 11/2011 |
| JP | 2012-163491 A | 8/2012 |
| JP | 2012-518294 A | 8/2012 |
| WO | WO 94/28075 A1 | 12/1994 |
| WO | WO 1998/03872 A2 | 1/1998 |
| WO | WO 98/12539 A1 | 3/1998 |
| WO | WO 99/41007 A2 | 8/1999 |
| WO | WO 00/16089 A2 | 3/2000 |
| WO | WO 01/43870 A2 | 6/2001 |
| WO | WO 03/001889 A2 | 1/2003 |
| WO | WO 03/023360 A2 | 3/2003 |
| WO | WO 03/038033 A2 | 5/2003 |
| WO | WO 2003/104273 A2 | 12/2003 |
| WO | 2004/027093 A1 | 4/2004 |
| WO | WO 2004/027093 A1 | 4/2004 |
| WO | WO 2005/014696 A1 | 2/2005 |
| WO | 2005/240811 A | 10/2005 |
| WO | WO 2007/038647 A2 | 4/2007 |
| WO | WO 2007/078868 A1 | 7/2007 |
| WO | WO 2008/097370 A2 | 8/2008 |
| WO | WO 2008/118167 A1 | 10/2008 |
| WO | WO 2014/078606 A2 | 10/2008 |
| WO | WO 2008/151146 A2 | 12/2008 |
| WO | WO 2009/132321 A1 | 10/2009 |
| WO | WO 2010/060155 A1 | 6/2010 |
| WO | WO 2010/085763 A1 | 7/2010 |
| WO | WO 2010/096593 A2 | 8/2010 |
| WO | WO 2011/034620 A2 | 3/2011 |
| WO | WO 2011/058136 A1 | 5/2011 |
| WO | WO 2012/122929 A1 | 9/2012 |
| WO | WO 2012/154594 A1 | 11/2012 |
| WO | WO 2012/174479 A1 | 12/2012 |
| WO | WO 2013/119845 A1 | 8/2013 |
| WO | WO 2014/052989 A2 | 4/2014 |
| WO | WO 2015/016315 A1 | 2/2015 |
| WO | WO 2015/029691 A1 | 3/2015 |

OTHER PUBLICATIONS

Beyer, M. et al., "Combinatorial Synthesis of Peptide Arrays Onto a Microchip," Science, Dec. 21, 2007, p. 1888, vol. 318, No. 5858.
Camarero, J., "Recent Developments in the Site-Specific Immobilization of Proteins Onto Solid Supports," Biopolymers, 2008, pp. 450-458, vol. 90, No. 3.
Canadian First Office Action, Canadian Application No. 2,864,080, dated Nov. 19, 2015, 6 pages.
Canadian Office Action, Canadian Application No. 2,864,080, dated Jul. 10, 2017, 5 pages.
Canadian Office Action, Canadian Application No. 2,885,839, dated Jul. 22, 2016, 4 pages.
Canadian Office Action, Canadian Application No. 2,885,839, dated Sep. 15, 2017, 4 pages.
Canadian Office Action, Canadian Application No. 2,891,651, dated Jun. 2, 2016, 5 pages.
Canadian Office Action, Canadian Application No. 2,891,651, dated Sep. 15, 2017, 4 pages.
Canadian Office Action, Canadian Application No. 2,901,029, dated Dec. 2, 2016, 7 pages.
Canadian Office Action, Canadian Application No. 2,901,029, dated Jul. 5, 2017, 8 pages.
Canadian Office Action, Canadian Application No. 2,901,029, dated May 5, 2016, 7 pages.
Canadian Office Action, Canadian Application No. 2,901,029, dated Sep. 8, 2015, 4 pages.
Canadian Second Office Action, Canadian Application No. 2,864,080, dated Dec. 1, 2016, 5 pages.
Canadian Second Office Action, Canadian Application No. 2,885,839, dated Apr. 20, 2017, 4 pages.
Canadian Second Office Action, Canadian Application No. 2,891,651, dated Feb. 10, 2017, 4 pages.
Carra, C. et al., "Proton-Coupled Electron Transfer in a Model for Tyrosine Oxidation in Photosystem II," Journal of the American Chemical Society, 2003, pp. 10429-10436, vol. 125.
Compound Summary for: CID 44140583, Tris(2,2'-bipyridine)ruthenium(II) dicholoride, 2009, 2 pages, [Online] [Retrieved on Jun. 29, 2014] Retrieved from the Internet URL:http://pubchem.ncbi.nlm.nih.gov/summary/summary.cgi?cid=44140593&loc=ec_rcs]>.
European Communication Under Rule 164(2)(a) EPC, European Application No. 13798499.3, dated Jun. 29, 2016, 4 pages.
European Examination Report, European Application No. 13747275.9, dated Sep. 21, 2017, 6 pages.
European Examination Report, European Application No. 13783134.3, dated Apr. 1, 2016, 4 pages.
European Examination Report, European Application No. 13783134.3, dated Dec. 19, 2017, 5 pages.
European Examination Report, European Application No. 13783134.3, dated Jun. 29, 2016, 12 pages.
European Examination Report, European Application No. 13798499.3, dated Sep. 23, 2016, 10 pages.
European Examination Report, European Application No. 14751871.6, dated Jul. 20, 2017, 5 pages.

(56) References Cited

OTHER PUBLICATIONS

European Extended Search Report, European Application No. 13747275.9, dated Sep. 25, 2015, 9 pages.

European Extended Search Report, European Application No. 14751871.6, dated Aug. 2, 2016, 6 pages.

European Invitation to Pay Additional Search Fees, European Application No. 13783134.3, dated May 2, 2016, 4 pages.

European Second Examination Report, European Application No. 13798499.3, dated May 23, 2017, 6 pages.

Gundagola, A.S.V., Synthesis, Photochemistry, and DNA Photocleavage of Compounds Containing Tetrazolethione Scaffolds, Kansas State University, 2011, 3 pages, [Online] [Retrieved on May 1, 2015] Retrieved from the Internet<URL:http://krex.kstate.edu/dspace/handle/2097/12022>.

Han, S-Y. et al., "Recent Development of Peptide Coupling Reagents in Organic Synthesis," Tetrahedron, 2004, pp. 2447-2467, vol. 60.

Japanese Office Action, Japanese Application No. 2015-558184, dated Jan. 25, 2016, 4 pages.

Japanese Office Action, Japanese Application No. 2014-556684, dated Apr. 4, 2016, 5 pages.

Japanese Office Action, Japanese Application No. 2015-534809, dated Aug. 28, 2017, 6 pages.

Japanese Office Action, Japanese Application No. 2016-126181, dated May 22, 2017, 10 pages.

Japanese Office Action, Japanese Application No. 2016-148004, dated Jun. 21, 2017, 7 pages.

Lim, J-H. et al., "Direct-Write Dip-Pen Nanolithography of Proteins on Modified Silicon Oxide Surfaces," Angewandte Chemie International Edition Wiley—VCH Verlag GmbH & Co. KGAA, May 25, 2003, pp. 2309-2312, vol. 42, No. 20.

Lin et al., "Synthesis of Water Soluble Photoinitiators of Thioxanthone Derivatives III" Huadong Ligong Daxue Xuebao, Journal of East China University of Science and Technology, 2000, pp. 212-214, 220, vol. 26, No. 2 (with English abstract).

Meinl, E. et al., "Myelin Basic Protein-Specific T Lymphocyte Repertoire in Multiple Sclerosis, Complexity of the Response and Dominance of Nested Epitopes Due to Recruitment of Multiple T Cell Clones," The Journal of Clinical Investigation, Dec. 1993, pp. 2633-2643, vol. 92, No. 6.

Merrifield, R.B., "Solid Phase Peptide Synthesis. I. The Synthesis of a Tetrapeptide," J Am. Chem. Soc., Jul. 20, 1963, pp. 2149-2154, vol. 85, No. 14.

PCT International Preliminary Report on Patentability for PCT International Application No. PCT/US13/25190, dated Apr. 4, 2014, 18 pages.

PCT International Preliminary Report on Patentability for PCT International Application No. PCT/US13/62773, dated Dec. 18, 2014, 7 pages.

PCT International Preliminary Report on Patentability for PCT International Application No. PCT/US14/16737, dated Feb. 24, 2015, 6 pages.

PCT International Preliminary Report on Patentability for PCT International Application No. PCT/US2013/070207, dated Mar. 30, 2015, 12 pages.

PCT International Search Report and Written Opinion, PCT Application No. PCT/US13/25190, dated Jun. 26, 2013, 22 pages.

PCT International Search Report and Written Opinion, PCT Application No. PCT/US14/16737, dated Aug. 11, 2014, 17 pages.

PCT International Search Report and Written Opinion, PCT Application No. PCT/US15/17173, dated Jun. 3, 2015, 16 pages.

PCT International Search Report and Written Opinion, PCT Application No. PCT/US15/49528, dated Feb. 1, 2016, 18 pages.

PCT International Search Report and Written Opinion, PCT Application No. PCT/US2013/062773, dated May 28, 2014, 20 pages.

PCT International Search Report and Written Opinion, PCT Application No. PCT/US2013/070207, dated Jun. 23, 2014, 19 pages.

PCT Invitation to Pay Additional Fees, PCT Application No. PCT/US13/25190, dated May 1, 2013, 4 pages.

PCT Invitation to Pay Additional Fees, PCT Application No. PCT/US14/16737, dated May 19, 2014, 2 pages.

PCT Invitation to Pay Additional Fees, PCT Application No. PCT/US15/49528, dated Nov. 20, 2015, 3 pages.

PCT Invitation to Pay Additional Fees, PCT Application No. PCT/US2013/062773, dated Mar. 7, 2014, 9 pages.

PCT Invitation to Pay Additional Fees, PCT Application No. PCT/US2013/070207, dated Mar. 14, 2014, 8 pages.

PCT Written Opinion for PCT International Application No. PCT/US2013/070207, dated Feb. 12, 2015, 13 pages.

Pellois, J.P. et al., "Individually Addressable Parallel Peptide Synthesis on Microchips". Nature Biotechnology, Sep. 2002, pp. 922-926, vol. 20, No. 9.

"Proteomics 2010: Solid-Phase Peptide Synthesis (SPPS) and Applications of Synthetic Peptides," Jan. 2010, 63 pages [Online] [Retrieved on Sep. 16, 2015] Retrieved from the Internet<URL:http://bas.niu.edu.tw/download.php?filename=12155_cf09f16c.ppt&dir=communicty_forum/31&title=Topic+10-SPPS>.

Resch-Genger et al., "Quantum Dots Versus Organic Dyes as Fluorescent Labels," Nature Methods, Sep. 2008, pp. 763-775, vol. 5, No. 9.

Sardesai, N.P. et al., "A Microfluidic Electrochemiluminescent Device for Detecting Cancer Biomarker Proteins," Anal. Bioanal. Chem. Epub Jan. 11, 2013, pp. 3831-3138, vol. 405, No. 11.

Shin et al., "Automated Maskless Photolithography System for Peptide Microarray Synthesis on a Chip," J. Comb. Chem., 2010, pp. 463-471, vol. 12, No. 4.

Sun X. et al., "Bicyclic Guanidinium Tetraphenylborate: A Photobase Generator and a Photocatalyst for living Anionic Ring-Opening Polymerization and Cross-Linking of Polymeric Materials Containing Ester and Hydroxy Groups" Journal of The American Chemical Society, Jul. 1, 2008, pp. 8130-8131, vol. 130(26).

Suyama K. et al., "Photobase Generators: Recent Progress and Application Trend in Polymer Systems", Progress in Polymer Science, Feb. 1, 2009, pp. 194-209, vol. 34(2), Pergamon Press, Oxford, GB.

Tapia, V. et al., "Evaluating the Coupling Efficiency of Phosphorylated Amino Acids for Spot Synthesis," J. Peptide Sci., 2008, pp. 1309-1314, vol. 14, No. 12.

Uddayasankar, U. "Towards a Surface Microarray Based Multiplexed Immunoassay on a Digital Microfluidics Platform," Master of Science Thesis, 2010, 78 pages, [Online] [Retrieved on Jun. 29, 2014] Retrieved from the Internet<URL:https://cipweb.cardinal-lp.com/PCTSRS/PCTSRS_DATA/PCT-US%2014-16737/PRIOR_ART_PCT-US_14-16737_Uddayasankar_Master_Thesis_2010.pdf>.

United States Office Action, U.S. Appl. No. 14/432,200, dated Jul. 19, 2017, 17 pages.

United States Office Action, U.S. Appl. No. 14/454,554, dated Mar. 16, 2015, 14 pages.

United States Office Action, U.S. Appl. No. 14/672,123, dated Dec. 21, 2015, 10 pages.

United States Office Action, U.S. Appl. No. 14/768,196, dated Sep. 22, 2017, 18 pages.

Wagner, "Quality Control for Peptide Chip Array Production," PhD Thesis, 2011, 140 pages, [Online] [Retrieved on Jun. 14, 2013] Retrieved from the Internet<URL:http://archiv.ub.uni-heidelberg.de/volltextserver/12602/1/report.pdf>.

Wang, L. et al., "Microfluidic DNA Microarray Analysis: A Review," Analytica Chimica Acta 687, 2011, pp. 12-27.

Wei, H. et al., "Electrochemiluminescence of tris(2,2'-bipyridyl)ruthenium and Its Applications in Bioanalysis: A Review," Luminescence, Mar.-Apr. 2011, pp. 77-85, vol. 26, Issue 2.

Young, J.D. et al., "Coupling Efficiencies of Amino Acids in the Solid Phase Synthesis of Peptides," Peptide Research, Jul./Aug. 1990, pp. 194-200, vol. 3, No. 4.

Yuan, L., et al., "Integrated Tyramide and Polymerization-Assisted Signal Amplification for a Highly-Sensitive Immunoassay," Anal. Chem., 2012, pp. 10737-10744, vol. 84, No. 24.

Zhao, Y. et al., "A Fluorescent Amino Acid Probe to Monitor Efficiency of Peptide Conjugation to Glass Surfaces for High Density Microarrays," Mol. Biosyst., Epub Jan. 13, 2012, pp. 879-887, vol. 8, No. 3.

Piehler, J. et al., "Protein Interaction in Covalently Attached Dextran Layers," Colloids and Surfaces B: Biointerfaces 13 (1999) pp. 325-336.

(56) References Cited

OTHER PUBLICATIONS

United States Office Action, U.S. Appl. No. 14/432,200, dated Feb. 8, 2017, 22 pages.
United States Office Action, U.S. Appl. No. 14/768,196, dated May 30, 2018, 16 pages.
United States Office Action, U.S. Appl. No. 14/941,404, dated May 30, 2018, ten pages.
Ballew, J.T., "Antibody Biomarker Discovery Through in Vitro Directed Evolution of Consensus Recognition Epitopes," Proceedings of the National Academy of Sciences of the United States of America, Nov. 26, 2013, pp. 19330-19335, vol. 110, No. 48.
Buus, S. et al., "High-Resolution Mapping of Linear Antibody Epitopes Using Ultrahigh-Density Peptide Microarrays," Molecular & Cellular Proteomics, Dec. 2012, pp. 1790-1800, vol. 11, No. 12.
Chen, "Solid-Phase Peptide Synthesis (SPPS) and Applications of Synthetic Peptides," Proteomics 2010.
Choung, R.S. et al., "Determination of B-Cell Epitopes in Patients with Celiac Disease: Peptide Microarrays," Plos One, e0147777, Jan. 29, 2016, pp. 1-16, vol. 11, No. 1.
Fathalla, E., et al., "Efficient Synthesis of 1-Substituted-4-phenyl-1, 4-dihydro-5H-tetrazole-5-thione and (1-Phenyl-1H-tetrazol-5-yl)thiozcetyl Derivatives," Heteroatom Chemistry, 2007, vol. 18, No. 6, pp. 637-643.
Gomez-Zavaglia, A. et al., "Molecular structure, vibrational spectra and photochemistry of 5-mercapto-1-methyltetrazole," Journal of Molecular Structure, 2006, vol. 786, pp. 182-192.
Piehler et al., "Protein interactions in covalently attached dextran layers", Colloids and Surfaces B Biointerfaces, vol. 13, pp. 325-336 (Jul. 1999).
Sun, X. et al., Bicyclic Guanidinium Tetraphenylborate: A Photobase Generator and A Photocatalyst for Living Anionic, J. Am. Chem. Soc., 2008, vol. 130, No. 26, pp. 8130-8131.
United States Office Action, U.S. Appl. No. 14/941,404, dated Dec. 11, 2018, 9 pages.
United States Office Action, U.S. Appl. No. 15/120,452, dated Sep. 18, 2017, 14 pages.
United States Office Action, U.S. Appl. No. 16/019,449, dated Apr. 29, 2019, 7 pages.
United States Office Action, U.S. Appl. No. 16/287,968, dated Jan. 6, 2020, 8 pages.
Wang et al, Microfluidic DNA microarray analysis: A review, 2011, Analytica Chimica Acta, 687, 12-27.

\* cited by examiner

Example of Well plate using PDMS Film on Glass slide

Top View

- Each well is 4mm by 4mm
- Spacing between wells is 1mm
- Glass slide-1 inch by 3 inch 1.2mm thick micro slides Well plate using PDMS Film Side View

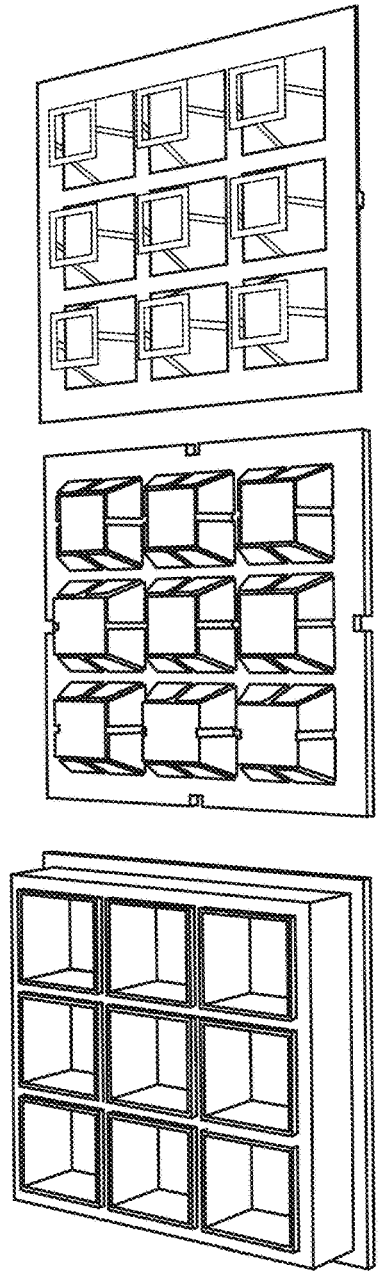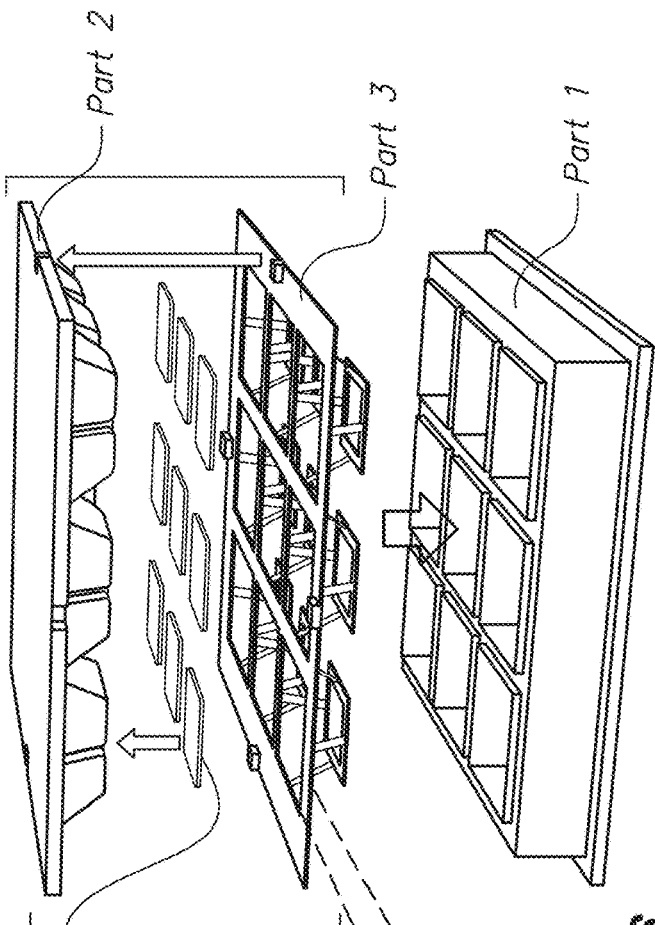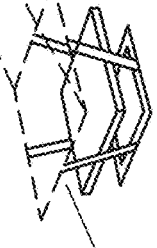
FIG. 16

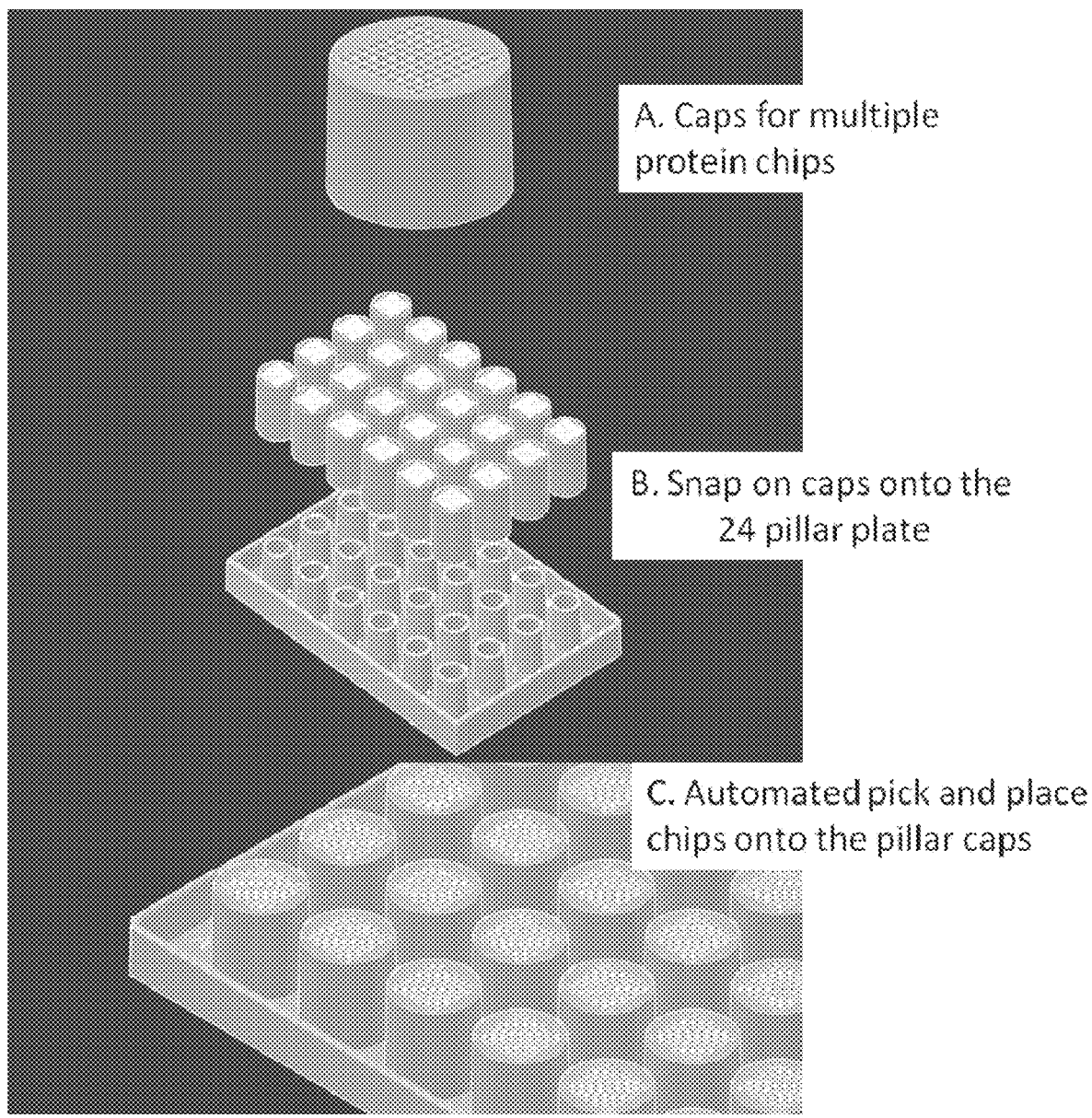
Figure 17A-C

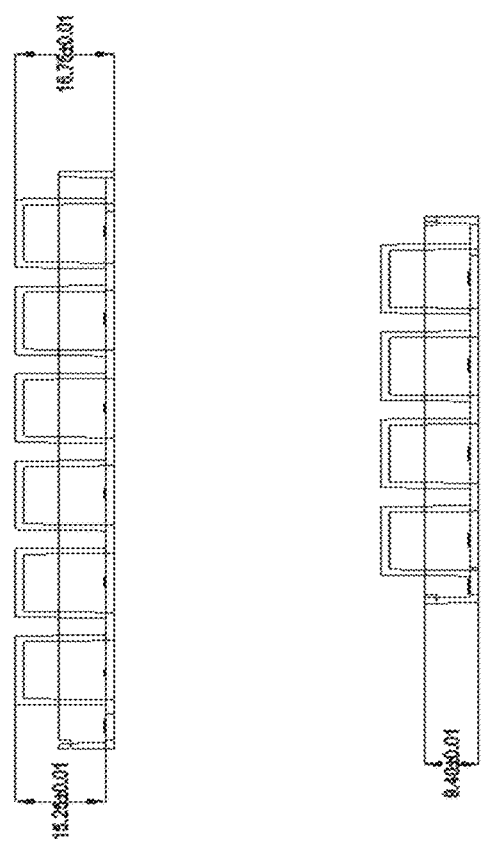
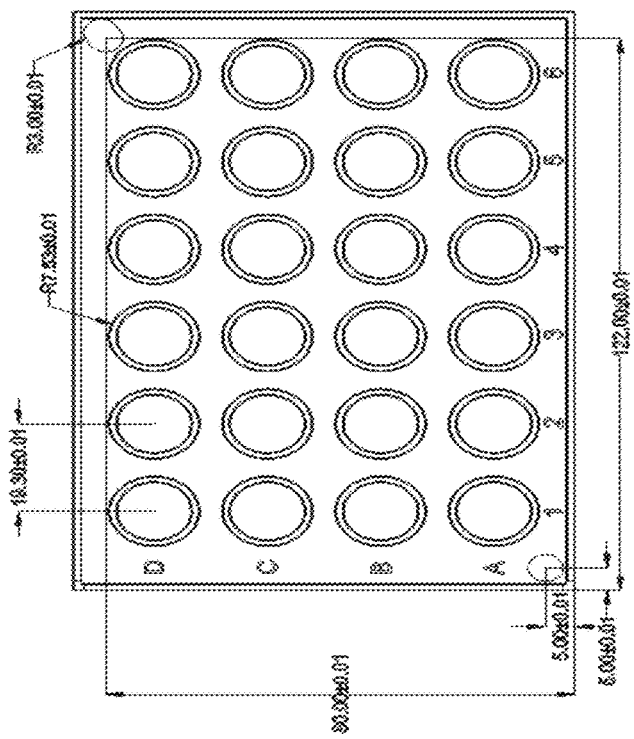
Figure 17D

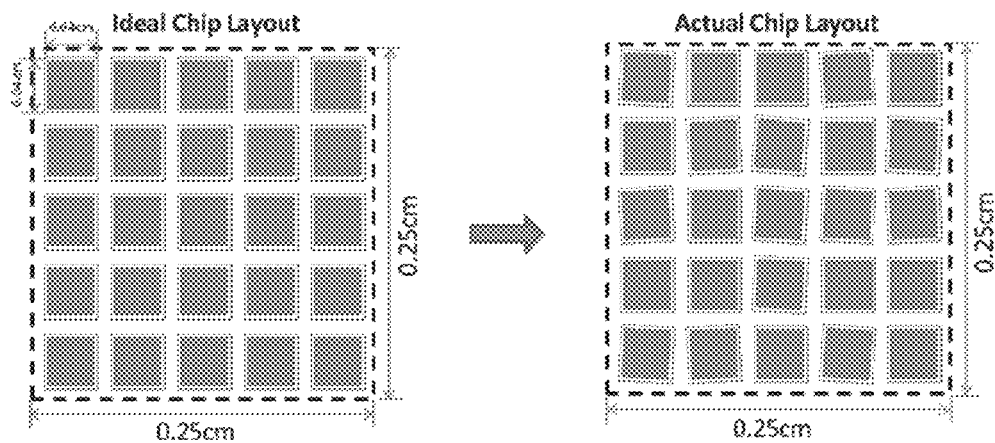
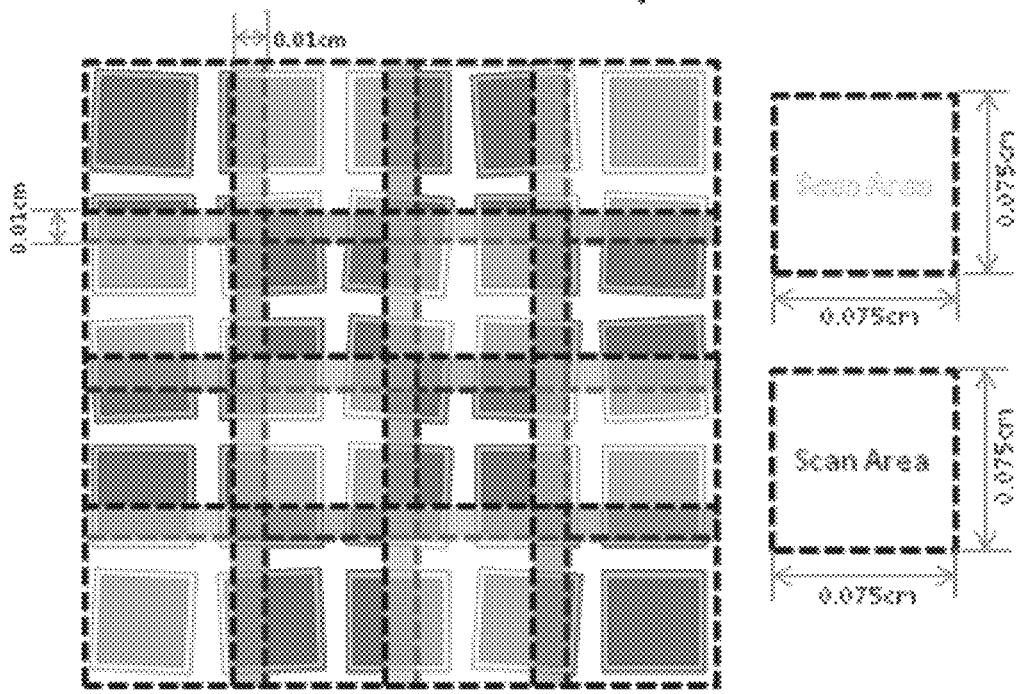
Figure 26

Process Flow

Step 1 — Chips are mounted on pillar plate with the help of the alignment with caps present on the front corners.

Process Flow

Step 2 — Pillar plate and it's stage are placed on the microscope stage and angle of rotation of the first chip about it's center (θ1) is determined Measure θ1

Process Flow

Step 5 — After the first chip is scanned, the second chip is processed for scanning and θ is determined for the second chip θ determined for second chip

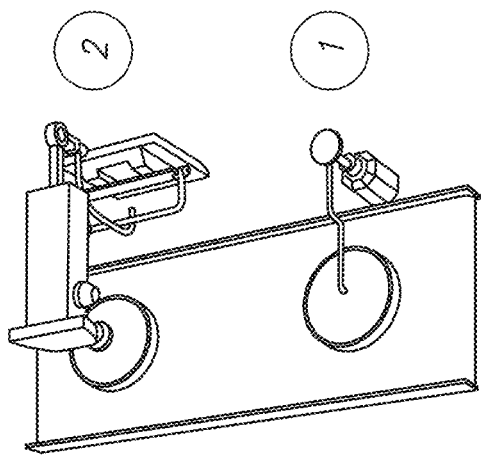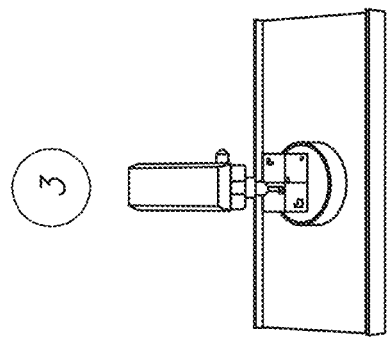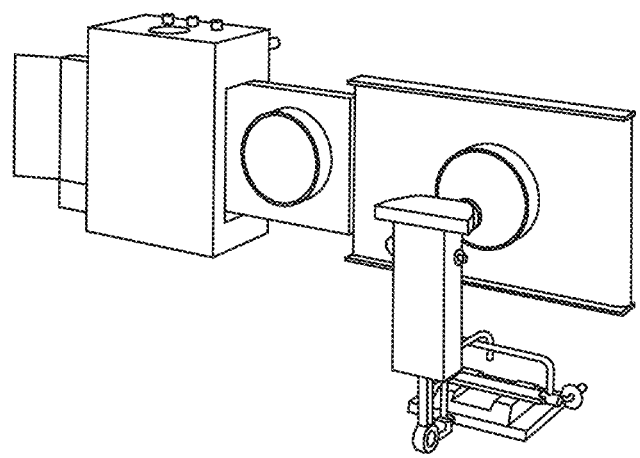
FIG. 42

METHODS, SYSTEMS, AND ARRAYS FOR BIOMOLECULAR ANALYSIS

CROSS-REFERENCE TO RELATED APPLICATIONS

This application is a continuation U.S. application Ser. No. 14/432,200, filed Sep. 14, 2015, which is a national phase application under 35 U.S.C. § 371 of International Patent Application No. PCT/US2013/062773, filed Sep. 30, 2013 which claims the benefit of U.S. Provisional Patent Application No. 61/707,758 filed Sep. 28, 2012, U.S. Provisional Patent Application No. 61/732,221, filed Nov. 30, 2012, U.S. Provisional Patent Application No. 61/805,884, filed Mar. 27, 2013, U.S. Provisional Patent Application No. 61/765,584, filed Feb. 15, 2013, U.S. Provisional Patent Application No. 61/866,512, filed Aug. 15, 2013, and which is also a continuation in part of International Patent Application No. PCT/US2013/025190, filed Feb. 7, 2013, which claims the benefit of U.S. Provisional Patent Application No. 61/726,515, filed Nov. 14, 2012, and U.S. Provisional Patent Application 61/761,347, filed Feb. 6, 2013, the disclosures of which are incorporated by reference in their entirety for all purposes.

BACKGROUND

A typical microarray system is generally comprised of biomolecular probes, such as DNA, proteins, or peptides, formatted on a solid planar surface like glass, plastic, or silicon chip, plus the instruments needed to handle samples (automated robotics), to read the reporter molecules (scanners) and analyze the data (bioinformatic tools). Microarray technology can facilitate monitoring of many probes per square centimeter. Advantages of using multiple probes include, but are not limited to, speed, adaptability, comprehensiveness and the relatively cheaper cost of high volume manufacturing. The uses of such an array include, but are not limited to, diagnostic microbiology, including the detection and identification of pathogens, investigation of anti-microbial resistance, epidemiological strain typing, investigation of oncogenes, analysis of microbial infections using host genomic expression, and polymorphism profiles.

SEQUENCE LISTING

The instant application contains a Sequence Listing which has been submitted electronically in ASCII format and is hereby incorporated by reference in its entirety. Said ASCII copy, created on May 11, 2018, is named 40566US_sequencelisting.txt and is 3,441 bytes in size.

Recent advances in genomics have culminated in sequencing of entire genomes of several organisms, including humans. Genomics alone, however, cannot provide a complete understanding of cellular processes that are involved in disease, development, and other biological phenomena; because such processes are often directly mediated by polypeptides. Given that huge numbers of polypeptides are encoded by the genome of an organism, the development of high throughput technologies for analyzing polypeptides is of paramount importance.

Peptide arrays with distinct analyte-detecting regions or probes can be assembled on a single substrate by techniques well known to one skilled in the art. A variety of methods are available for creating a peptide microarray. These methods include: (a) chemo selective immobilization methods; and (b) in situ parallel synthesis methods which can be further divided into (1) SPOT synthesis and (2) photolithographic synthesis.

SUMMARY

The invention encompasses, in several embodiments formulations, substrates, and arrays. The invention also includes methods for manufacturing and using the formulations, substrates, and arrays.

In one embodiment, the invention includes a method for obtaining peptide binding data, comprising: obtaining a peptide array, said array comprising at least 10,000 peptide features/square millimeter; contacting said array with a sample comprising a plurality of ligands for at least a subset of said 100,000 peptide features under conditions that promote ligand binding; and imaging said array to identify binding of said plurality of ligands to said peptide array.

In some embodiments of the method, a total number of features is at least about 500,000, 1,000,000, 2,000,000, or 18,000,000. In other embodiments of the method, said microarray has an area that is less than or equal to 0.2, 1, 10, 100, or 150 square millimeters. In yet other embodiments of the method, said sample has a volume that is less than or equal to 100, 50, 10, 5, 1.5, or 1 pt. In some embodiments of the method, an elapsed time from sample contacting to imaging is less than 20, 5, or 1 minutes. In some embodiments of the method, a coefficient of variation of data obtained from said array is not greater than 5, 2, or 1 percent. In some embodiments of the method, said microarray comprises at least 1,000,000, 10,000,000, 15,000,000 features per square centimeter. In some embodiment of the method, said contacting occurs at a concentration of said plurality of ligands that is within the range of approximately 1 µg/ml to approximately 1,000 µg/ml in said sample. In some embodiment of the method, said imaging comprises identifying binding of at least 1,000, 100,000, 1,000,000, 10,000,000, 15,000,000 or 100,000,000 ligands to said features of said microarray. In some embodiment of the method, said features are selected from a group consisting of proteins, DNA binding sequences, antibodies, peptides, oligonucleotides, nucleic acids, peptide nucleic acids, deoxyribonucleic acids, ribonucleic acids, peptide mimetics, nucleotide mimetics, chelates, and biomarkers.

In one embodiment, the invention includes an inverted pillar plate for assaying microarrays, comprising: a plurality of chip mounts, each chip mount configured to affix at least one of a plurality of microarrays and to prevent the at least one microarray from being displaced from the chip mount when the chip mount is placed facing downwards into a well containing an assay solution; and a plate comprising a plurality of inverted plate pillars that extend approximately perpendicular from the plate, each inverted plate pillar configured to be coupled to one of the plurality of chip mounts, wherein each chip mount is affixed to at least one of the plurality of inverted plate pillars so that each chip mount is prevented from being displaced from the at least one inverted plate pillar when the plate is turned upside down.

In some embodiment, the invention includes a method of assaying chip arrays, comprising: providing a plurality of chip mounts, each chip mount configured to affix a microarray and to prevent the microarray from being displaced from the chip mount when the chip mount is placed facing downwards into a well containing an assay solution; affixing a plurality of microarrays onto the chip mounts; providing a pillar plate comprising a plurality of inverted plate pillars that extend approximately perpendicular from the pillar plate, each plate pillar configured to be coupled to one of the plurality of chip mounts; affixing the chip mounts with the affixed microarrays to at least one of the plurality of plate pillars so that each chip mount is prevented from being displaced from the at least one plate pillar when the pillar plate is turned upside down; and assaying the plurality of microarrays by turning the pillar plate upside down and placing each microarray into a well comprising assay solution.

In some embodiment, the invention includes a method of assuring uniformly high quality of a microarray of features that are attached to a surface of the microarray at positionally-defined locations, comprising: soft-baking the microarray coated with a coupling formulation, the coupling formulation comprising the features; determining the thickness of the soft-baked microarray; responsive to the thickness of the soft-backed microarray falling outside a first threshold range starting over soft-baking the microarray after stripping off the coat; exposing the soft-baked microarray to light under a photomask; hard-baking the exposed microarray; and responsive to the thickness of the hard-backed microarray falling outside a second threshold range starting over with soft-baking the microarray after stripping off the coat.

In some embodiment, the invention includes a method of assuring uniformly high quality of a microarray of features that are attached to a surface of the microarray at positionally-defined locations, comprising: soft-baking the microarray coated with a coupling formulation, the coupling formulation comprising the features; exposing the soft-baked microarray to light under a photomask, the photomask comprising a diffusion pattern and a overlay pattern; hard-baking the exposed microarray; and responsive to the diffusion pattern or the overlay pattern of the hard-backed microarray falling outside a tolerance range when compared to a standard diffusion or overlay pattern starting over with soft-baking the microarray after stripping off the coat.

In one embodiment, the invention includes a method for collecting data from a chip array and for piecewise real-time scanning and stitching of said data, comprising steps of: providing a chip array comprising of: a plurality of microarrays, each microarray comprising features that are attached to a surface of the microarray at positionally-defined locations, aligning a first region of the chip array with a scan mask of a microscope; imaging the first region of the chip array under the scan mask by the microscope; and rotating, by using a computer processor, the imaged first region of the chip array into standard orientation based on an alignment mark on a surface of a microarray that is at a positionally-defined location within the imaged first region.

In some embodiment, the data-collecting method further comprises steps of: aligning a second region of the chip array with the scan mask so that the second region partially overlaps with the first region; imaging the second region of the chip array under the scan mask by the microscope; and rotating, by using a computer processor, the imaged second region of the chip array into standard orientation based on an alignment mark on a surface of a microarray that is at a positionally-defined location within the imaged second region. In some of these embodiments, the method further comprises steps of combining the rotated images of the first and second region for analyzing the features located on the surface of the microarrays within the imaged first and second region, wherein any overlapping parts of the imaged first and second region are averaged for the analysis.

In some embodiment, the data-collecting method further comprises steps of: storing the rotated images of the first and second region within a image database.

BRIEF DESCRIPTION OF THE SEVERAL VIEWS OF THE DRAWINGS

These and other features, embodiments, and advantages of the present invention will become better understood with regard to the following description, and accompanying drawings, where:

FIG. 16 shows schematics of a chip array with well plates using inverted pillars and its use with a 3×3 well plate in an assay, according to one embodiment.

FIGS. 17A-E show a chip array structure of multiple chips on top of pillar caps with the pillar caps attached to a pillar plate, according to one embodiment. FIG. 17A shows a chip or a plurality of chips placed onto a pillar cap. FIG. 17B shows the interface of each pillar cap with a pillar plate of 24 pillars. FIG. 17C shows the assembled chip array structure. FIGS. 17D and E show the dimensions of a 24-pillar and 96-pillar plate, respectively.

FIG. 26 shows an ideal and actual layout of chips on a chip array and corresponding areas on the chip array scanned by confocal microscope, according to one embodiment.

FIG. 42 shows a chip array system for performing inline quality control on a chip array, according to one embodiment.

FIG. 41A includes a chart that translates measured intensities to a grey-scale displayed in the intensity profiles.

DETAILED DESCRIPTION

Definitions

Figure 1:
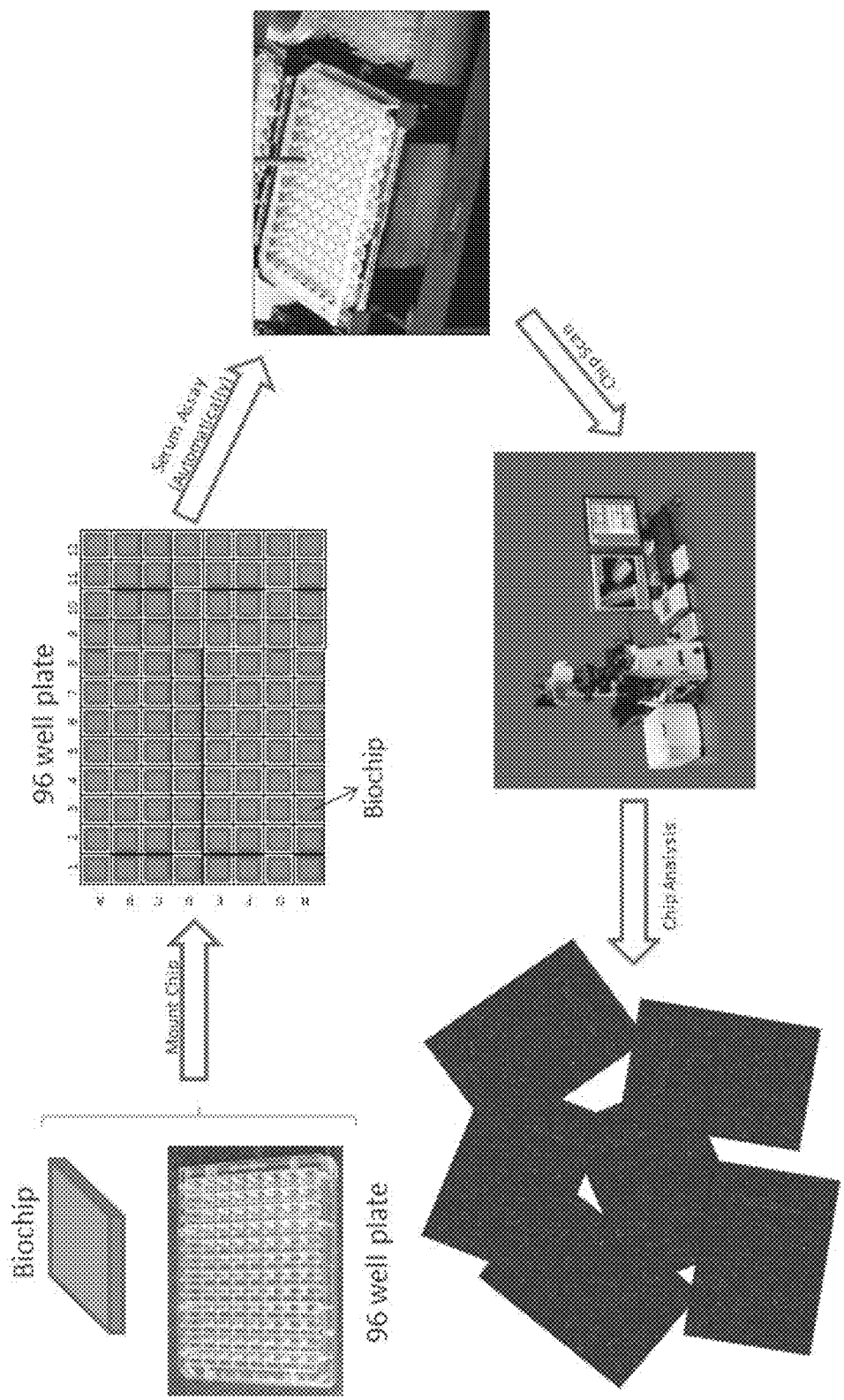
FIG. 1 shows a flow chart for performing an assay using a chip array with a robotic device, according to one embodiment.

Terms used in the claims and specification are defined as set forth below unless otherwise specified.

As used herein the term "wafer" refers to a slice of semiconductor material, such as a silicon or a germanium crystal generally used in the fabrication of integrated circuits. Wafers can be in a variety of sizes from, e.g., 25.4 mm (1 inch) to 300 mm (11.8 inches) along one dimension with thickness from, e.g., 275 µm to 775 µm.

As used herein the term "photoresist" or "resist" or "photoactive material" refers to a light-sensitive material that changes its solubility in a solution when exposed to ultra violet or deep ultra violet radiation. Photoresists are organic or inorganic compounds that are typically divided into two types: positive resists and negative resists. A positive resist is a type of photoresist in which the portion of the photoresist that is exposed to light becomes soluble to the photoresist developer. The portion of the photoresist that is unexposed remains insoluble to the photoresist developer. A negative resist is a type of photoresist in which the portion of the photoresist that is exposed to light becomes insoluble to the photoresist developer. The unexposed portion of the photoresist is dissolved by the photoresist developer.

As used herein the term "photomask" or "reticle" or "mask" refers to an opaque plate with transparent patterns or holes that allow light to pass through. In a typical exposing process, the pattern on a photomask is transferred onto a photoresist As used herein the term "coupling molecule" includes in one embodiment any natural or artificially synthesized amino acid with its amino group protected with a fluorenylmethyloxycarbonyl (Fmoc) or tert-Butyloxycarbonyl (boc) group. These amino acids may optionally have their side chains protected. Examples of coupling molecules include, but are not limited to, boc-Gly-COOH, Fmoc-Trp-COOH. Other embodiments of coupling molecules include monomer molecules and combinations thereof that can form polymers upon coupling, e.g., nucleotides, sugars and the like, and are described below.

As used here in the term "coupling" or "coupling process" or "coupling step" refers to a process of forming a bond between two or more molecules such as a linker molecule or a coupling molecule. A bond can be a covalent bond such as a peptide bond. A peptide bond can a chemical bond formed between two molecules when the carboxyl group of one coupling molecule reacts with the amino group of the other coupling molecule, releasing a molecule of water ($H_2O$). This is a dehydration synthesis reaction (also known as a condensation reaction), and usually occurs between amino acids. The resulting —C(=O)NH— bond is called a peptide bond, and the resulting molecule is an amide.

As used herein the terms "polypeptide," "peptide," or "protein" are used interchangeably to describe a chain or polymer of amino acids that are linked together by bonds. Accordingly, the term "peptide" as used herein includes a dipeptide, tripeptide, oligopeptide, and polypeptide. The term "peptide" is not limited to any particular number of amino acids. In some embodiments, a peptide contains about 2 to about 50 amino acids, about 5 to about 40 amino acids, or about 5 to about 20 amino acids. A molecule, such as a protein or polypeptide, including an enzyme, can be a "native" or "wild-type" molecule, meaning that it occurs naturally in nature; or it may be a "mutant," "variant," "derivative," or "modification," meaning that it has been made, altered, derived, or is in some way different or changed from a native molecule or from another molecule such as a mutant. A "point mutation" refers to the mutation of one amino acid among the amino acids in a sequence of a peptide.

As used herein the term "biomarkers" includes, but is not limited to DNA, RNA, proteins (e.g., enzymes such as kinases), peptides, sugars, salts, fats, lipids, ions and the like.

As used herein the term "linker molecule" or "spacer molecule" includes any molecule that does not add any functionality to the resulting peptide but spaces and extends out the peptide from the substrate, thus increasing the distance between the substrate surface and the growing peptide. This generally reduces steric hindrance with the substrate for reactions involving the peptide (including uni-molecular folding reactions and multi-molecular binding reactions) and so improves performance of assays measuring one or more embodiments of peptide functionality.

As used herein the term "developer" refers to a solution that can selectively dissolve the materials that are either exposed or not exposed to light. Typically developers are water-based solutions with minute quantities of a base added. Examples include tetramethyl ammonium hydroxide in water-based developers. Developers are used for the initial pattern definition where a commercial photoresist is used. Use of developers is described in Example 1 below.

As used herein the term "protecting group" includes a group that is introduced into a molecule by chemical modification of a functional group in order to obtain chemoselectivity in a subsequent chemical reaction. "Chemoselectivity" refers to directing a chemical reaction along a desired path to obtain a pre-selected product as compared to another. For example, the use of boc as a protecting group enables chemoselectivity for peptide synthesis using a light mask and a photoacid generator to selectively remove the protecting group and direct pre-determined peptide coupling reactions to occur at locations defined by the light mask.

As used herein the term "microarray," "array" or "chip" refers to a substrate on which a plurality of probe molecules of protein or specific DNA binding sequences have been affixed at separate locations in an ordered manner thus forming a microscopic array. Protein or specific DNA binding sequences may be bound to the substrate of the chip through one or more different types of linker molecules. A "chip array" refers to a plate having a plurality of chips, for example, 24, 96, or 384 chips.

As used herein the term "probe molecules" refers to, but is not limited to, proteins, DNA binding sequences, antibodies, peptides, oligonucleotides, nucleic acids, peptide nucleic acids ("PNA"), deoxyribonucleic acids (DNA), ribonucleic acids (RNA), peptide mimetics, nucleotide mimetics, chelates, biomarkers and the like. As used herein, the term "feature" refers to a particular probe molecule that has been attached to a microarray. As used herein, the term "ligand" refers to a molecule, agent, analyte or compound of interest that can bind to one or more features.

As used herein the term "microarray system" or a "chip array system" refers to a system usually comprised of probe molecules formatted on a solid planar surface like glass, plastic or silicon chip plus the instruments needed to handle samples (automated robotics), to read the reporter molecules (scanners) and analyze the data (bioinformatic tools).

As used herein the term "patterned region" or "pattern" or "location" refers to a region on the substrate on which are grown different features. These patterns can be defined using photomasks.

As used herein the term "derivatization" refers to the process of chemically modifying a surface to make it suitable for bio molecular synthesis. Typically derivatization includes the following steps: making the substrate hydrophilic, adding an amino silane group, and attaching a linker molecule.

As used herein the term "capping" or "capping process" or "capping step" refers to the addition of a molecule that prevents the further reaction of the molecule to which it is attached. For example, to prevent the further formation of a peptide bond, the amino groups are typically capped by acetylation in the presence of an acetic anhydride molecule.

As used herein the term "diffusion" refers to the spread of, e.g., photoacid through random motion from regions of higher concentration to regions of lower concentration.

As used herein the term "dye molecule" refers to a dye which typically is a colored substance that can bind to a substrate. Dye molecules can be useful in detecting binding between a feature on an array and a ligand, e.g. a molecule of interest.

As used herein, the terms "immunological binding" and "immunological binding properties" refer to the non-covalent interactions of the type which occur between an immunoglobulin molecule and an antigen for which the immunoglobulin is specific.

As used herein the term "biological sample" refers to a sample derived from biological tissue or fluid that can be assayed for an analyte(s) of interest or any ligand. Such samples include, but are not limited to, sputum, amniotic fluid, blood, blood cells (e.g., white cells), tissue or fine needle biopsy samples, urine, peritoneal fluid, and pleural fluid, or cells therefrom. Biological samples may also include sections of tissues such as frozen sections taken for histological purposes. Although the sample is typically taken from a human patient, the assays can be used to detect analyte(s) of interest in samples from any organism (e.g., mammal, bacteria, virus, algae, or yeast) or mammal, such as dogs, cats, sheep, cattle, and pigs. The sample may be pretreated as necessary by dilution in an appropriate buffer solution or concentrated, if desired.

As used herein, the term "assay" refers to a type of biochemical test that measures the presence or concentration of a substance of interest in solutions that can contain a complex mixture of substances.

The term "antigen" as used herein refers to a molecule that triggers an immune response by the immune system of a subject, e.g., the production of an antibody by the immune system. Antigens can be exogenous, endogenous or auto antigens. Exogenous antigens are those that have entered the body from outside through inhalation, ingestion or injection. Endogenous antigens are those that have been generated within previously-normal cells as a result of normal cell metabolism, or because of viral or intracellular bacterial infection. Auto antigens are those that are normal protein or protein complex present in the host body but can stimulate an immune response.

As used herein the term "epitope" or "immunoactive regions" refers to distinct molecular surface features of an antigen capable of being bound by component of the adaptive immune system, e.g., an antibody or T cell receptor. Antigenic molecules can present several surface features that can act as points of interaction for specific antibodies. Any such distinct molecular feature can constitute an epitope. Therefore, antigens have the potential to be bound by several distinct antibodies, each of which is specific to a particular epitope.

As used herein the term "antibody" or "immunoglobulin molecule" refers to a molecule naturally secreted by a particular type of cells of the immune system: B cells. There are five different, naturally occurring isotypes of antibodies, namely: IgA, IgM, IgG, IgD, and IgE.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information website.

It must be noted that, as used in the specification and the appended claims, the singular forms "a," "an," and "the" include plural referents unless the context clearly dictates otherwise.

Compositions

Substrates

Also disclosed herein are substrates. In some embodiments, a substrate comprises a planar (e.g., 2-dimensional) layer. In some embodiments, the surface of a substrate comprises pillars for attachment or synthesis of molecules, e.g. peptides, or a first monomer building block. In other embodiments, a substrate includes a porous (i.e., a 3-dimensional) layer comprising functional groups for binding a first monomer building block. In some embodiments, a porous layer is added to the top of the pillars. In some embodiments, the substrate comprises a porous layer coupled to the planar layer. In other embodiments, the substrate comprises a plurality of pillars coupled to the planar layer.

In some embodiment, the planar layer can comprise any metal or plastic or silicon or silicon oxide or silicon nitride. In some embodiment, the planar layer has an upper surface and a lower surface. In some embodiments, the support layer is 1,000-2,000 angstroms thick. In some embodiments, the planar layer is about less than 500, 1,000, 2,000, 3,000, 4,000, 5,000, 6,000, 7,000, 8,000, 9,000, 10,000, 11,000, 12,000, or greater than 12,000 angstroms thick (or any integer in between). In some embodiments, the metal is chromium. In some embodiments, the metal is chromium, titanium, aluminum, tungsten, gold, silver, tin, lead, thallium, indium, or a combination thereof. In some embodiments, the planar layer is at least 98.5-99% metal. In some embodiments, the planar layer is 100% metal. In some embodiments, the planar layer is at least about greater than 90, 91, 92, 93, 94, 95, 96, 97, 98, 98.5, or 99% metal. In some embodiments, the planar layer is a homogenous layer of metal.

In some embodiments, a substrate surface is derivatized with free carboxylic acid groups. In other embodiments, a substrate surface is derivatized with free amine groups. In yet other embodiments, a substrate surface is derivatized with other free functional groups for solid state synthesis. A surface that is derivatized with free amine groups can be converted to free carboxylic acid groups by reacting the amine with one carboxylic acid group of a molecule having at least two free carboxylic acid groups. For example, by using carbodiimide one carboxylic acid group is first activated to form an intermediate O-acylisourea that then further reacts with the free amine groups for an amide bond and attached to the substrate surface. In some embodiments, the molecule with multiple carboxylic acid groups includes, but is not limited to, succinic anhydride, polyethylene glycol diacid, benzene-1,3,5-tricarboxylic acid, benzenehexacarboxylic acid and carboxymethyl dextran. For example, the free carboxylic acid or free amine groups bind amino acids, peptides or proteins during peptide synthesis and protein coupling. In another example, the free functional groups bind to linker molecules that couple ("link") other probe molecules or biomarkers to the substrate. In some embodiments, a coupling molecule is attached to the surface of at least one pillar. In other embodiments, a coupling molecule is attached to the surface of each pillar.

In some embodiments, a polymer is in contact with the surface of at least one of said pillars. In other embodiments, a polymer is in contact with the surface of each pillar. In some embodiments, a gelatinous form of a polymer is in contact with the surface of at least one of said pillars. In some embodiments, a solid form of a water soluble polymer is in contact with the surface of at least one of said pillars.

In some embodiments, the substrate surface comprises silicon dioxide for contacting the surface with a photoactive coupling formulation comprising a photoactive compound, a coupling molecule, a coupling reagent, a polymer, and a solvent, wherein the contracting is followed by applying ultraviolet light to positionally-defined locations located on the top of the surface and in contact with the photoactive coupling formulation.

In some embodiments, the substrate surface is a material or group of materials having rigidity or semi-rigidity. In some embodiments, the substrate surface can be substantially flat, although in some embodiments it can be desirable to physically separate synthesis regions for different molecules or features with, for example, wells, raised regions, pins, pillars, etched trenches, or the like. In certain embodiments, the substrate surface may be porous. Surface materials can include, for example, silicon, bio-compatible polymers such as, for example poly(methyl-methacrylate) (PMMA) and polydimethylsiloxane (PDMS), glass, $SiO_2$ (such as a thermal oxide silicon wafer used by the semiconductor industry), quartz, silicon nitride, functionalized glass, gold, platinum, and aluminum.

Derivatized substrate surfaces include, for example, amino-derivatized glass, carboxy-derivatized glass, and hydroxyl-derivatized glass. Additionally, a surface may optionally be coated with one or more layers to provide a second surface for molecular attachment or derivatization, increased or decreased reactivity, binding detection, or other specialized application. Substrate surface materials and/or layer(s) can be porous or non-porous. For example, a substrate surface comprises porous silicon.

Pillar Substrate

In some embodiments, a substrate comprises a planar layer comprising a metal and having an upper surface and a lower surface; and a plurality of pillars operatively coupled to the planar layer in positionally-defined locations, wherein each pillar has a planar surface extended from the planar layer, wherein the distance between the surface of each pillar and the upper surface of the planar layer is between about 1,000-5,000 angstroms, and wherein the plurality of pillars are present at a density of greater than about $10,000/cm^2$. In other embodiments, the distance between the surface of each pillar and the upper surface of the planar layer can be between about less than 1,000, 2,000, 3,000, 3,500, 4,500, 5,000, or greater than 5,000 angstroms (or any integer in between).

In some embodiments, the surface of each pillar is parallel to the upper surface of the planar layer. In some embodiments, the surface of each pillar is substantially parallel to the upper surface of the planar layer.

In some embodiments, the distance between the surface of each pillar and the lower surface of the planar layer is 2,000-7,000 angstroms. In other embodiments, the distance between the surface of each pillar and the lower surface of the planar layer is about less than 500, 1,000, 2,000, 3,000, 4,000, 5,000, 6,000, 7,000, 8,000, 9,000, 10,000, 11,000, 12,000, or greater than 12,000 angstroms (or any integer in between). In yet other embodiments, the distance between the surface of each pillar and the lower surface of the planar layer is 7,000, 3,000, 4,000, 5,000, 6,000, or 7,000 angstroms (or any integer in between).

In some embodiments, the plurality of pillars are present at a density of greater than 500, 1,000, 2,000, 3,000, 4,000, 5,000, 6,000, 7,000, 8,000, 9,000, 10,000, 11,000, or $12,000/cm^2$ (or any integer in between). In other embodiments, the plurality of pillars are present at a density of greater than $10,000/cm^2$. In yet other embodiments, the plurality of pillars are present at a density of about $10,000/cm^2$ to about 2.5 million/$cm^2$ (or any integer in between). In some embodiments, the plurality of pillars are present at a density of greater than 2.5 million/$cm^2$.

In some embodiments, the surface area of each pillar surface is at least 1 $\mu m^2$. In other embodiments, the surface area of each pillar surface can be at least 0.1, 0.5, 12, 3, 4, 5, 6, 7, 8, 9, 10, 15, 20, 25, 30, 35, 40, 45, or 50 $\mu m^2$ (or any integer in between). In yet other embodiments, the surface area of each pillar surface has a total area of less than 10,000 $\mu m^2$. In yet other embodiments, the surface area of each pillar surface has a total area of less than 500, 1,000, 2,000, 3,000, 4,000, 5,000, 6,000, 7,000, 8,000, 9,000, 10,000, 11,000, or 12,000 $\mu m^2$ (or any integer in between). In some embodiments, the surface of each pillar is square or rectangular in shape.

In some embodiments, the center of each pillar is at least 2,000 angstroms from the center of any other pillar. In other embodiments, the center of each pillar is at least about 500, 1,000, 2,000, 3,000, or 4,000 angstroms (or any integer in between) from the center of any other pillar. In yet other embodiments, the center of each pillar is at least about 2 $\mu m$ to 200 $\mu m$ from the center of any other pillar.

In some embodiments, at least one or each pillar comprises silicon. In other embodiments, at least one or each pillar comprises silicon dioxide or silicon nitride. In some of these embodiments, at least one or each pillar is at least 90, 91, 92, 93, 94, 95, 96, 97, 98, 98.5, or 99% silicon dioxide.

In some embodiments, the metal of the planar layer is chromium. In other embodiments, the metal is chromium, titanium, aluminum, tungsten, gold, silver, tin, lead, thallium, indium, or a combination thereof. In some embodiments, the planar layer is at least 98.5-99% (by weight) metal. In other embodiments, the planar layer is 100% metal. In yet other embodiments, the planar layer is at least about greater than 90, 91, 92, 93, 94, 95, 96, 97, 98, 98.5, or 99% metal. In some embodiments, the planar layer is a homogenous layer of metal.

In the surface of at least one of said pillars of the substrate is derivatized. In some embodiments, a substrate can include a polymer chain attached to the surface of at least one of said pillars. In some embodiments, the polymer chain comprises a peptide chain. In some embodiments, the attachment to the surface of said at least one pillar is via a covalent bond.

In some embodiments, the substrate can be coupled to a silicon dioxide layer. The silicon dioxide layer can be about 0.5 μm to 3 μm thick. In some embodiments, the substrate can be coupled to a wafer, e.g., a silicon wafer. The silicon wafer can be about 700 μm to 750 μm thick.

Porous Layers Substrate

In another embodiments, a substrate comprises a porous layer coupled to a plurality of pillars, wherein the porous layer comprises functional groups for attachment of a molecule to the substrate, and wherein the plurality of pillars are coupled to a planar layer in positionally-defined locations, each pillar having a planar surface extended from the planar layer by the distance between the surface of each pillar and the upper surface of the planar layer that is between about 1,000-5,000 angstroms, and the plurality of pillars are present at a density of greater than about $10,000/cm^2$.

Porous layers that can be used are flat, permeable, polymeric materials of porous structure that have a carboxylic acid functional group (that is native to the constituent polymer or that is introduced to the porous layer) for attachment of the first peptide building block. For example, a porous layer can be comprised of porous silicon with functional groups for attachment of a polymer building block attached to the surface of the porous silicon. In another example, a porous layer can comprise a cross-linked polymeric material. In some embodiments, the porous layer can employ polystyrenes, saccharose, dextrans, polyacryloylmorpholine, polyacrylates, polymethylacrylates, polyacrylamides, polyacrylolpyrrolidone, polyvinylacetates, polyethyleneglycol, agaroses, sepharose, other conventional chromatography type materials and derivatives and mixtures thereof. In some embodiments, the porous layer building material is selected from: poly(vinyl alcohol), dextran, sodium alginate, poly(aspartic acid), poly(ethylene glycol), poly(ethylene oxide), poly(vinyl pyrrolidone), poly(acrylic acid), poly(acrylic acid)-sodium salt, poly(acrylamide), poly(N-isopropyl acrylamide), poly(hydroxyethyl acrylate), poly(acrylic acid), poly(sodium styrene sulfonate), poly(2-acrylamido-2-methyl-1-propanesulfonic acid), polysaccharides, and cellulose derivatives. Preferably the porous layer has a porosity of 10-80%. In one embodiment, the thickness of the porous layer ranges from 0.01 μm to about 1,000 μm. Pore sizes included in the porous layer may range from 2 nm to about 100 μm.

In another embodiment the porous layer comprises a porous polymeric material having a porosity from 10-80%, wherein reactive groups are chemically bound to the pore surfaces and are adapted in use to interact, e.g. by binding chemically, with a reactive species, e.g., deprotected monomeric building blocks or polymeric chains. In one embodiment the reactive group is a free carboxylic acid or a free amine group. For example, the carboxylic acid group is free to bind an unprotected amine group of an amino acid, peptide or polypeptide for peptide synthesis.

Linker Molecules

In some embodiments, the substrate surface is coupled to a plurality of linker molecules. A linker molecule is a molecule inserted between a substrate surface disclosed herein and a first coupling molecule that is e.g. the N-terminal amino acid of a peptide being synthesized. A linker molecule does not necessarily convey functionality to the resulting peptide, such as molecular recognition functionality, but can instead elongate the distance between the surface and the synthesized peptide to enhance the exposure of the peptide's functionality region(s) on the surface.

In some embodiments, a linker can be about 4 to about 40 atoms long to provide exposure. The linker molecules can be, for example, aryl acetylene, ethylene glycol oligomers containing 2-10 monomer units, diamines, diacids, amino acids, and combinations thereof. Examples of diamines include ethylene diamine and diamino propane.

Alternatively, linkers can be the same molecule type as that being synthesized (e.g., nascent polymers or various coupling molecules), such as polypeptides and polymers of amino acid derivatives such as for example, amino hexanoic acids. In some embodiments, a linker molecule is a molecule having a carboxylic group at a first end of the molecule and a protecting group at a second end of the molecule. In some embodiments, the protecting group is a boc or Fmoc protecting group. In some embodiments, a linker molecule comprises an aryl-acetylene, a polyethyleneglycol (PEGs), a nascent polypeptide, a diamine, a diacid, a peptide, or combinations thereof.

The unbound portion of a linker molecule, or free end of the linker molecule, can have a reactive functional group which is blocked, protected, or otherwise made unavailable for reaction by a removable protective group, e.g., boc or Fmoc as noted above. The protecting group can be bound to a monomer, a polymer, or a linker molecule to protect a reactive functionality on the monomer, polymer, or linker molecule. Protective groups that can be used include all acid and base labile protecting groups. For example, peptide amine groups can be protected by tert-butyloxycarbonyl (boc) or benzyloxycarbonyl (CBZ), both of which are acid labile, or by 9-fluorenylmethoxycarbonyl (Fmoc), which is base labile.

Additional protecting groups that can be used include acid labile groups for protecting amino moieties: tert-amyloxycarbonyl, adamantyloxycarbonyl, 1-methylcyclobutyloxycarbonyl, 2-(p-biphenyl)propyl(2)oxycarbonyl, 2-(p-phenylazophenylyl)propyl(2)oxycarbonyl, alpha,alpha-dimethyl-3,5-dimethyloxybenzyloxy-carbonyl, 2-phenylpropyl(2)oxycarbonyl, 4-methyloxybenzyloxycarbonyl, furfuryloxycarbonyl, triphenylmethyl (trityl), p-toluenesulfenylaminocarbonyl, dimethylphosphinothioyl, diphenylphosphinothioyl, 2-benzoyl-1-methylvinyl, o-nitrophenylsulfenyl, and 1-naphthylidene; as base labile groups for protecting amino moieties: 9 fluorenylmethyloxycarbonyl, methylsulfonylethyloxycarbonyl, and 5-benzisoazolylmethyleneoxycarbonyl; as groups for protecting amino moieties that are labile when reduced: dithiasuccinoyl, p-toluene sulfonyl, and piperidino-oxycarbonyl; as groups for protecting amino moieties that are labile when oxidized: (ethylthio)carbonyl; as groups for protecting amino moieties that are labile to miscellaneous reagents, the appropriate agent is listed in parenthesis after the group: phthaloyl (hydrazine), trifluoroacetyl (piperidine), and chloroacetyl (2-aminothiophenol); acid labile groups for protecting carboxylic acids: tert-butyl ester; acid labile groups for protecting hydroxyl groups: dimethyltrityl. (See also, Greene, T. W., Protective Groups in Organic Synthesis, Wiley-Interscience, NY, (1981)).

In some embodiments, the linker molecule is silane-(boc), where (boc) represents a tert-butyloxycarbonyl protecting group. In some embodiments, the linker molecule is silane-Gly-PEG(boc). In some embodiments, the linker molecule is silane-Gly-PEG-PEG(boc). In some embodiments, the linker molecule is silane-Gly-(PEG(boc))$_2$. In some embodiments, the linker molecule is silane-PEG-Gly(boc). In some embodiments, the linker molecule is silane-Gly-cyc-PEG (boc), where Gly-cyc represents a glycine chain with a cyclic glycine chain conformation. In some embodiments, the linker molecule is silane-Gly-(PEG(boc))$_4$.

In some embodiments, linker molecules attached to the surface of each pillar of the pillar substrate described above comprise a free amine or free carboxylic acid group. In other embodiments, linker molecules attached to the surface of at least one pillar of the pillar substrate comprise a free amine or free carboxylic acid group. In some embodiments, a linker molecule having a protecting group is attached to the surface of each pillar. In other embodiments, a linker molecule having a protecting group is attached to the surface of at least one pillar.

Linker Formulations

Also disclosed herein is a linker formulation used for reacting a linker molecule with the substrate. A linker formulation can include components such as a linker molecule, a polymer, a solvent and a coupling reagent.

In some embodiments, a linker molecule is about 0.5-5 weight % of the total formulation concentration. In some embodiments, a linker molecule is about less than 0.1, 0.1, 0.2, 0.3, 0.4, 0.5, 0.6, 0.7, 0.8, 0.9, 1.0, 1.1, 1.2, 1.3., 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0 weight % of the total formulation concentration.

In some embodiments, the polymer is 1 weight % polyvinyl alcohol and 2.5 weight % poly vinyl pyrrollidone, the linker molecule is 1.25 weight % polyethylene oxide, the coupling reagent is 1 weight % 1-ethyl-3-(3-dimethylaminopropyl) carbodiimide, and the solvent includes water. In some embodiments, the polymer is 0.5-5 weight % polyvinyl alcohol and 0.5-5 weight % poly vinyl pyrrollidone, the linker molecule is 0.5-5 weight % polyethylene oxide, the coupling reagent is 0.5-5 weight % 1-ethyl-3-(3-dimethylamino-propyl) carbodiimide, and the solvent includes water.

In some embodiments, the polymer is a polyvinyl pyrrolidone and/or a polyvinyl alcohol. The general structure of polyvinyl alcohol is as follows, where n is any positive integer greater than 1:

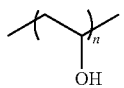

In some embodiments, the polymer is about 0.5-5 weight % of the total formulation concentration. In some embodiments, a water soluble polymer is about less than 0.1, 0.1, 0.2, 0.3, 0.4, 0.5, 0.6, 0.7, 0.8, 0.9, 1.0, 1.1, 1.2, 1.3., 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0 weight % of the total formulation concentration.

In some embodiments, the solvent is water, an organic solvent, or a combination thereof. In some embodiments, the organic solvent is N-methyl pyrrolidone, dimethyl formamide, dichloromethane, dimethyl sulfoxide, or a combination thereof. In some embodiments, the solvent is about 80-90 weight % of the total formulation concentration. In some embodiments, the solvent is about less than 70, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or greater than 99 weight % of the total formulation concentration.

In some embodiments, the coupling reagent is carbodiimide. In some embodiments, a coupling reagent is a water soluble triazole. In some embodiments, a coupling reagent is 1-ethyl-3-(3-dimethylaminopropyl) carbodiimide. In some embodiments, the coupling reagent is about 0.5-5 weight % of the total formulation concentration. In some embodiments, the coupling reagent is about less than 0.1, 0.1, 0.2, 0.3, 0.4, 0.5, 0.6, 0.7, 0.8, 0.9, 1.0, 1.1, 1.2, 1.3., 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0 weight % of the total formulation concentration.

Microarrays

Also disclosed herein are microarrays. Embodiments of a microarray ("chip") comprise a substrate and features attached to the substrate surface at positionally-defined locations.

In some embodiments, a microarray comprises two-dimensional array, wherein the positionally-defined locations occupy a 2-dimensional plane. For example, each feature can comprise: a collection of peptide chains of determinable sequence and intended length, wherein within an individual feature, the fraction of peptide chains within said collection having the intended length is characterized by an average coupling efficiency for each coupling step of about 98%. In some embodiments, the average coupling efficiency for each coupling step is at least 98.5%. In some embodiments, the average coupling efficiency for each coupling step is at least 99%. In some embodiments, the average coupling efficiency for each coupling step is at least 90, 91, 92, 93, 94, 95, 96, 97, 98, 98.5, 98.6, 98.7, 98.8, 98.9, 99.0, 99.1, 99.2, 99.3, 99.4, 99.5, 99.6, 99.7, 99.8, 99.9, or 100%.

In some embodiments, the features attached to the substrate surface are selected from a group consisting of: proteins, DNA binding sequences, antibodies, peptides, oligonucleotides, nucleic acids, peptide nucleic acids, deoxyribonucleic acids, ribonucleic acids, peptide mimetics, nucleotide mimetics, chelates, biomarkers, and the like.

In some embodiments, the substrate surface of the microarray is functionalized with free amine or free carboxylic acids for polypeptide synthesis. In some embodiments, the free carboxylic acids are activated to bind to amine groups, e.g., during polypeptide synthesis on the surface of the microarray.

In some embodiments, the surface density of features on the microarray is greater than 10/cm$^2$, 100/cm$^2$, 1,000/cm$^2$, 10,000/cm$^2$, 100,000/cm$^2$, 1,000,000/cm$^2$, 10,000,000/cm$^2$ or 20,000,000/cm$^2$. In some embodiments, the total number of features on the microarray is at least about 100,000, 200,000, 300,000, 400,000, 500,000, 600,000, 700,000, 800,000, 900,000, 1,000,000, 2,000,000, 3,000,000, 4,000,000, 5,000,000, 6,000,000, 7,000,000, 8,000,000, 10,000,000, 12,000,000, 14,000,000, 16,000,000, or 18,000,000. In other embodiments, the size of the microarray is less than or equal to 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 200, 250, 300, 400, 500, 600, 700, 800, 900, or 1,000 square millimeters.

In some embodiments, a microarray can be a three-dimensional array, e.g., the substrate comprising a porous layer with features attached to the surface of the porous layer. In some embodiments, the surface of a porous layer includes external surfaces and surfaces defining pore volume within the porous layer. In some embodiments, a three-dimensional microarray can include features attached to a surface at positionally-defined locations, said features each comprising: a collection of peptide chains of determinable sequence and intended length. In one embodiment, within an individual feature, the fraction of peptide chains within said collection having the intended length is characterized by an average coupling efficiency for each coupling step of greater than 98%. In some embodiments, the average coupling efficiency for each coupling step is at least 90, 91, 92, 93, 94, 95, 96, 97, 98, 98.5, 98.6, 98.7, 98.8, 98.9, 99.0, 99.1, 99.2, 99.3, 99.4, 99.5, 99.6, 99.7, 99.8, 99.9, or 100%.

In some embodiments, each peptide chain is from 5 to 60 amino acids in length. In some embodiments, each peptide chain is at least 5 amino acids in length. In some embodiments, each peptide chain is at least 5, 10, 15, 20, 25, 30, 35, 40, 45, 50, 55, or 60 amino acids in length. In some embodiments, each peptide chain is less than 5, at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or greater than 60 amino acids in length. In some embodiments, each peptide chain comprises one or more L amino acids. In some embodiments, each peptide chain comprises one or more D amino acids. In some embodiments, each peptide chain comprises one or more naturally occurring amino acids. In some embodiments, each peptide chain comprises one or more synthetic amino acids.

In some embodiments, a microarray can include at least 1,000 different peptide chains attached to the surface. In some embodiments, a microarray can include at least 10,000 different peptide chains attached to the surface. In some embodiments, a microarray can include at least 100, 500, 1000, 2000, 3000, 4000, 5000, 6000, 7000, 8000, 9000, 10,000, or greater than 10,000 different peptide chains attached to the surface (or any integer in between).

In some embodiments, a microarray can include a single protein, peptide chain, or antibody attached to a plurality of different types of linker molecules. In some embodiments a microarray can include at least 2 different types of linker molecules. In some embodiments, a microarray can include at least 2, 3, 4, 5, 6, 7, 8, 9, 10, 15, 20, 25, 30, 40, 50, 75, or greater than 100 different types of linker molecules attached to the substrate.

In some embodiments, each of the positionally-defined locations is at a different, known location that is physically separated from each of the other positionally-defined locations. In some embodiments, each of the positionally-defined locations is a positionally-distinguishable location. In some embodiments, each determinable sequence is a known sequence. In some embodiments, each determinable sequence is a distinct sequence.

In some embodiments, the features are covalently attached to the surface. In some embodiments, said peptide chains are attached to the surface through a linker molecule or a coupling molecule.

In some embodiments, the features comprise a plurality of distinct, nested, overlapping peptide chains comprising subsequences derived from a source protein having a known sequence. In some embodiments, each peptide chain in the plurality is substantially the same length. In some embodiments, each peptide chain in the plurality is the same length. In some embodiments, each peptide chain in the plurality is at least 5 amino acids in length. In some embodiments, each peptide chain in the plurality is at least 5, 10, 15, 20, 25, 30, 35, 40, 45, 50, 55, or 60 amino acids in length. In some embodiments, each peptide chain in the plurality is less than 5, at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or greater than 60 amino acids in length. In some embodiments, at least one peptide chain in the plurality is at least 5 amino acids in length. In some embodiments, at least one peptide chain in the plurality is at least 5, 10, 15, 20, 25, 30, 35, 40, 45, 50, 55, or 60 amino acids in length. In some embodiments, at least one peptide chain in the plurality is less than 5, at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or greater than 60 amino acids in length. In some embodiments, each polypeptide in a feature is substantially the same length. In some embodiments, each polypeptide in a feature is the same length. In some embodiments, the features comprise a plurality of peptide chains each having a random, determinable sequence of amino acids.

Chip Arrays

Also disclosed herein are chip arrays. In some embodiments, a chip array is a two-dimensional array of microarrays ("chips") on a support layer or plate. In some embodiments of chip arrays, each chip only comprises a single protein or antibody. In other embodiments, each chip comprises a plurality of proteins, antibodies, peptides, oligonucleotides, DNA, RNA, peptide nucleic acid ("PNA"), probe molecules and the like. In some embodiments, chips are packaged onto a 96 well plate. In some embodiments, epoxy is used to attach a chip to the waiver. In some embodiments, the support layer is an array of pillars, and a chip or a plurality of chips is attached to each pillar. These pillars of the support layer are of macroscopic scale and are to be distinguished from the substrate pillars described above. In other embodiments, a chip is attached to a cap which attaches to a pillar on a pillar plate.

In one embodiment, chips are formed on a silicon wafer, the silicon wafer being the support layer, and then diced into multiple chips of varying dimensions (FIG. 1). In some embodiments, each chip has a dimension of 1 mm by 1 mm up to 2 cm to 2 cm. In some embodiments, the chips formed on a wafer and diced into multiple chips fit onto 24-, 96-, 192-, or 384-well plates, or any other custom made plates. In some embodiments, these plates have a plurality of wells which act as containers for each chip. In some embodiments, the plate is used for in-vitro diagnostics, such as protein-protein interaction assays or other enzymatic reactions.

Robotic Chip Array System

Shown in FIG. 1 is a flow chart for performing an assay using a chip array with a robotic system. In some embodiments, the assay station is automated to perform liquid handling on the chip array. In some embodiments, the liquid handling assay station is any commercially available one that can use the standard or custom made well plates which hold the plurality of chips. After performing the assay using a liquid handling assay station, the chip is scanned using any commercially available confocal or CCD scanner. In some embodiments, the confocal scanner scans multiple chips loaded onto the substrate. In some embodiments, the data from the confocal scanner is analyzed on a Vibrant Bio Analyzer.

Figure 2:
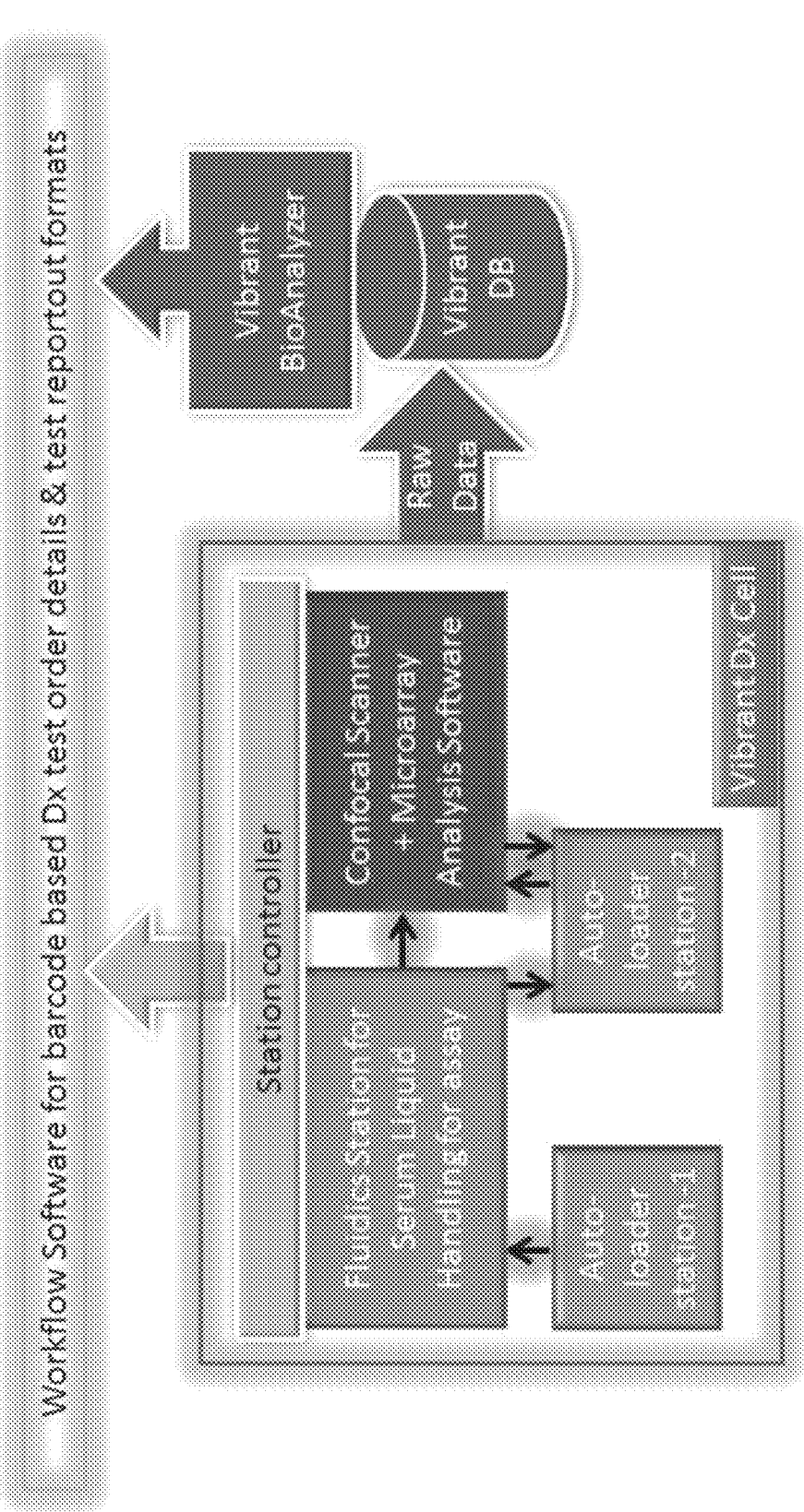
FIG. 2 shows a flow chart depicting an example of a chip array analysis process, according to one embodiment.

In some embodiments, one or several autoloader units feed the plate to the liquid handling assay station. Once the assay is performed, the chips are scanned on the confocal scanner using an autoloader. In some embodiments, one or several confocal scanners are connected to the autoloader to allow the autoloader to transfer chip arrays to a one or a plurality of scanners. A flow chart depicting an example of the chip array analysis process is shown in FIG. 2.

Figure 3:
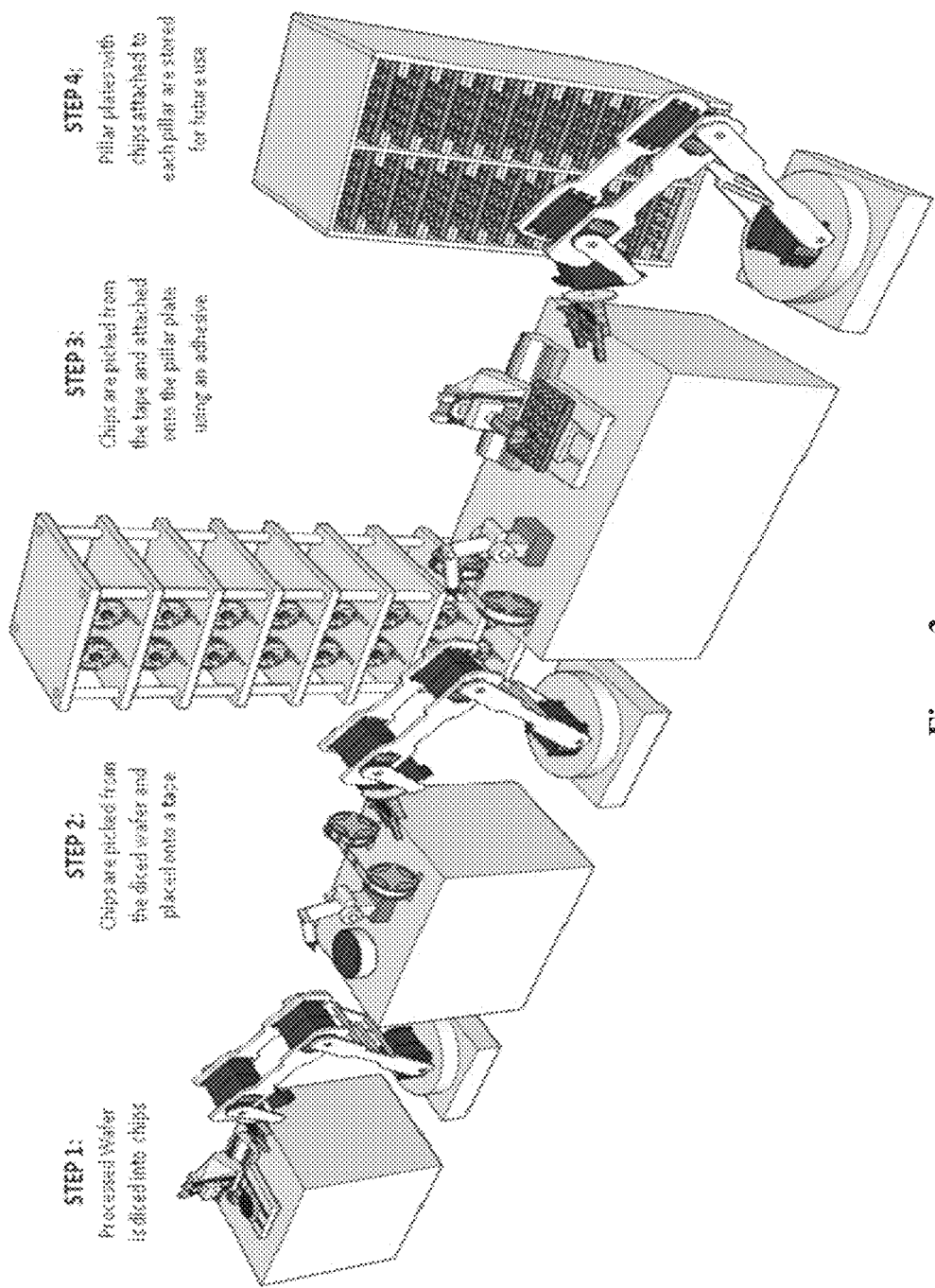
FIG. 3 shows a robotic chip array system for performing steps in a packing process of chip arrays, according to one embodiment.

FIG. 3 illustrates the packaging process of the chips including the steps of: dicing the quality controlled processed wafer into chips, picking the diced chips from the diced wafer and placing them onto a tape, picking the chips from the tape and attaching them onto a pillar plate using adhesive, and storing the pillar plates with chips attached to each pillar for future use.

Figure 4:
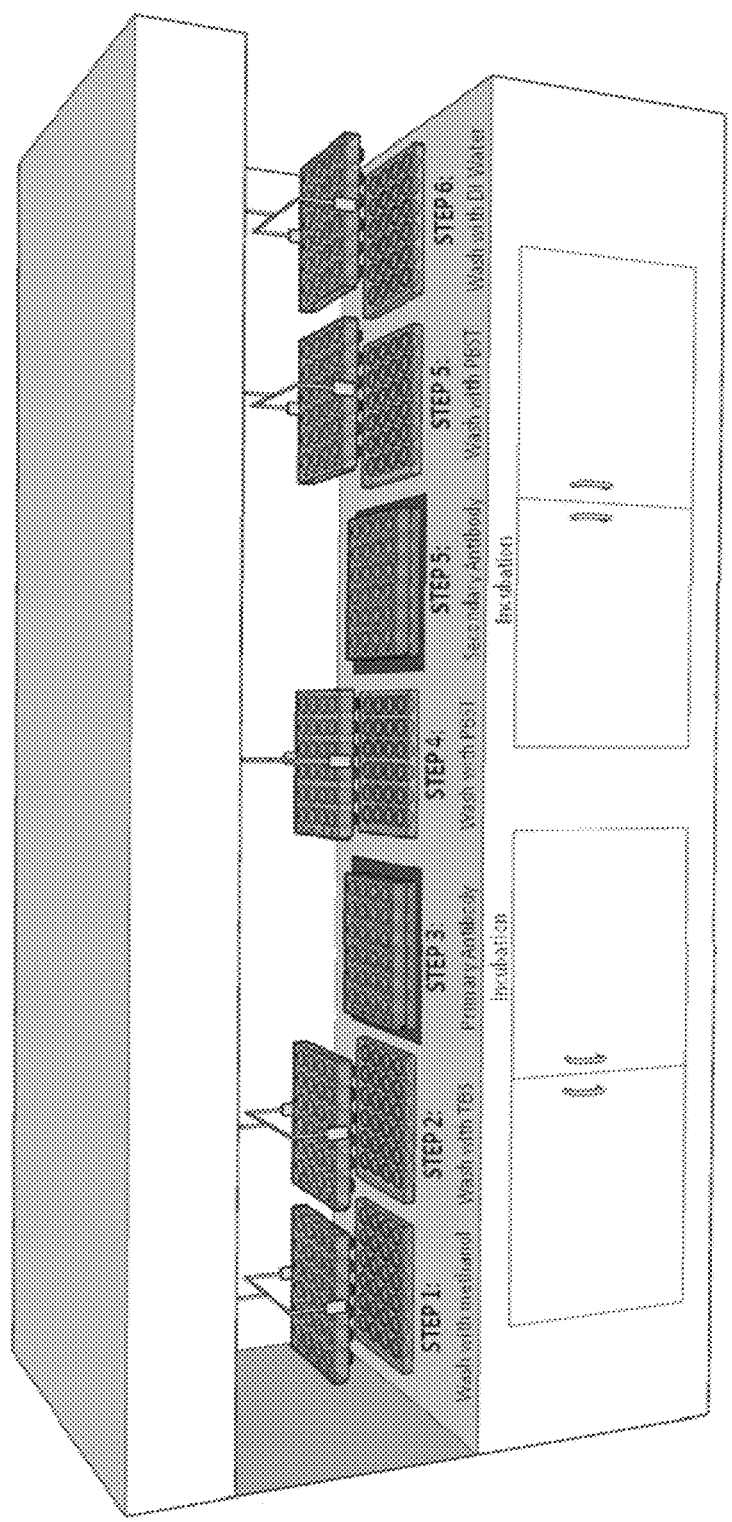
FIG. 4 shows a workbench system for performing steps in an assay using chip arrays and well plates, according to one embodiment.

FIG. 4 illustrates the bioassay process of the pillar plates with chips attached to each plate including the steps of: placing and washing the pillar plate in a first well plate filled methanol, picking up the pillar plate from the first well plate and transporting it to a second well plate filled with TBS for washing. In the third step, the process places the pillar plate in third well plate for incubation with the primary antibody, followed by washing the pillar plate in a fourth well plate containing PBST. The next step includes placing the pillar plate in a fifth well plate for incubation with the secondary antibody, followed by washing the pillar plate in a sixth well plate with PBST and then by washing it in a seventh well plate with DI water before drying the pillar plate in nitrogen for further analysis.

Figure 5:
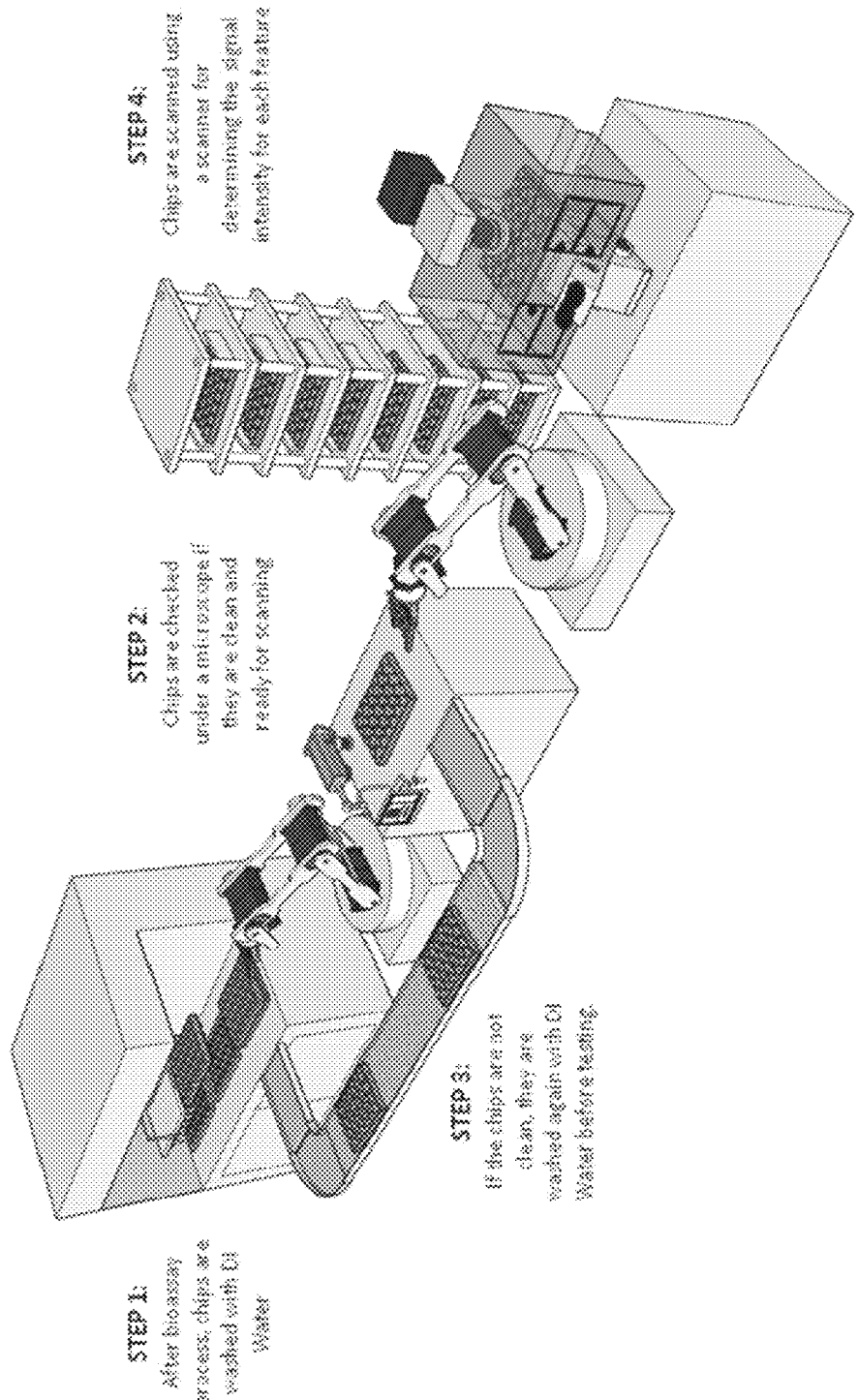
FIG. 5 shows a robotic chip array system for performing steps in scanning chip arrays, according to one embodiment.

FIG. 5 illustrates the scanning process of the assayed chips including the steps of: checking the chips under the microscope to determine if they are clean and ready for scanning, washing the chips in DI water if the chips are determined to be contaminated, scanning the chips by using a confocal scanner microscope to determine the signal intensity for each feature located on the chips.

Methods

Method of Manufacturing Substrates

Also disclosed herein are methods for making substrates. In some embodiments, a method of producing a substrate can include coupling a porous layer to a support layer. The support layer can comprise any metal or plastic or silicon or silicon oxide or silicon nitride. In one embodiment, the substrate comprises multiple carboxylic acid substrates attached to the substrate for binding peptides during peptide synthesis and protein coupling. In some embodiments, a method of producing a substrate can include coupling a porous layer to a plurality of substrate pillars, wherein the porous layer comprises functional groups for attachment of a compound to the substrate, wherein the plurality of substrate pillars are coupled to a planar layer in positionally-defined locations, wherein each substrate pillar has a planar surface extended from the planar layer, wherein the distance between the surface of each substrate pillar and the upper surface of the planar layer is between about 1,000-5,000 angstroms, and wherein the plurality of substrate pillars are present at a density of greater than about 10,000/cm$^2$.

In some embodiments, the surface of each substrate pillar is parallel to the upper surface of the planar layer. In some embodiments, the surface of each substrate pillar is substantially parallel to the upper surface of the planar layer.

In some embodiments, a method of preparing a substrate surface can include obtaining a surface comprising silicon dioxide and contacting the surface with a photoactive coupling formulation comprising a photoactive compound, a coupling molecule, a coupling reagent, a polymer, and a solvent; and applying ultraviolet light to positionally-defined locations located on the top of the surface and in contact with the photoactive formulation.

Methods of Manufacturing Microarrays

Also disclosed herein are methods for manufacturing microarrays. In some embodiments, the microarrays disclosed herein can be synthesized in situ on a surface, e.g., the substrate disclosed herein. In some instances, the microarrays are made using photolithography. For example, the substrate is contacted with a photoactive coupling solution. Masks can be used to control radiation or light exposure to specific locations on a surface provided with free linker molecules or free coupling molecules having protecting groups. In the exposed locations, the protecting groups are removed, resulting in one or more newly exposed reactive moieties on the coupling molecule or linker molecule. The desired linker or coupling molecule is then coupled to the unprotected attached molecules, e.g., at the carboxylic acid group. The process can be repeated to synthesize a large number of features in specific or positionally-defined locations on a surface (see, for example, U.S. Pat. No. 5,143,854 to Pirrung et al., U.S. Patent Application Publication Nos. 2007/0154946 (filed on Dec. 29, 2005), 2007/0122841 (filed on Nov. 30, 2005), 2007/0122842 (filed on Mar. 30, 2006), 2008/0108149 (filed on Oct. 23, 2006), and 2010/0093554 (filed on Jun. 2, 2008), each of which is herein incorporated by reference).

In some embodiments, a method of producing a three-dimensional microarray of features, can include obtaining a porous layer attached to a surface; and attaching the features to the porous layer, said features each comprising a collection of peptide chains of determinable sequence and intended length, wherein within an individual feature, the fraction of peptide chains within said collection having the intended length is characterized by an average coupling efficiency for each coupling step of at least about 98%. In some embodiments, the features are attached to the surface using a photoactive coupling formulation, comprising a photoactive compound, a coupling molecule, a coupling reagent, a polymer, and a solvent. In some embodiments, the features are attached to the surface using a photoactive coupling formulation disclosed herein. In some embodiments, the photoactive coupling formulation is stripped away using water.

In one embodiment, described herein is a process of manufacturing an microarray. A surface comprising attached carboxylic acid groups is provided. The surface is contacted with a photoactive coupling solution comprising a photoactive compound, a coupling molecule, a coupling reagent, a polymer, and a solvent. The surface is exposed to ultraviolet light in a deep ultra violet scanner tool according to a pattern defined by a photomask, wherein the locations exposed to ultraviolet light undergo photo base generation due to the presence of a photobase generator in the photoactive coupling solution. The expose energy can be from 1 mJ/cm$^2$ to 100 mJ/cm$^2$ in order to produce enough photobase.

The surface is post baked upon exposure in a post exposure bake module. Post exposure bake acts as a chemical amplification step. The baking step amplifies the initially generated photobase and also enhances the rate of diffusion to the substrate. The post bake temperature can vary between 75° Celsius to 115° Celsius, depending on the thickness of the porous surface, for at least 60 seconds and not usually exceeding 120 seconds. The free carboxylic acid group is coupled to the deprotected amine group of a free peptide or polypeptide, resulting in coupling of the free peptide or polypeptide to the carboxylic acid group attached to the surface. This surface may be a porous surface. The synthesis of peptides coupled to a carboxylic acid group attached to the surface occurs in an N→C synthesis orientation, with the amine group of free peptides attaching to carboxylic acid groups bound to the surface of the substrate. Alternatively, a diamine linker may be attached to a free carboxylic acid group to orient synthesis in a C→N direction, with the carboxylic acid group of free peptides attaching to amine groups bound to the surface of the substrate.

The photoactive coupling solution can now be stripped away. In some embodiments, provided herein is a method of stripping the photoresist completely with deionized (DI) water. This process is accomplished in a developer module. The wafer is spun on a vacuum chuck for, e.g., 60 seconds to 90 seconds and deionized water is dispensed through a nozzle for about 30 seconds.

The photoactive coupling formulation may be applied to the surface in a coupling spin module. A coupling spin module can typically have 20 nozzles or more to feed the photoactive coupling formulation. These nozzles can be made to dispense the photoactive coupling formulation by means of pressurizing the cylinders that hold these solutions or by a pump that dispenses the required amount. In some embodiments, the pump is employed to dispense 5-8 cc of the photoactive coupling formulation onto the substrate. The substrate is spun on a vacuum chuck for 15-30 seconds and the photoactive coupling formulation is dispensed. The spin speed can be set to 2000 rpm to 2500 rpm.

Optionally, a cap film solution coat is applied on the surface to prevent the non-reacted amino groups on the substrate from reacting with the next coupling molecule. The cap film coat solution can be prepared as follows: a solvent, a polymer, and a coupling molecule. The solvent that can be used can be an organic solvent like N-methyl pyrrolidone, dimethyl formamide, or combinations thereof. The capping molecule is typically acetic anhydride and the polymer can be polyvinyl pyrrolidone, polyvinyl alcohol, polymethyl methacrylate, poly-(methyl-isopropenyl)-ketone, or poly-(2-methyl-pentene-1-sulfone). In some embodiments, the capping molecule is ethanolamine.

This process is done in a capping spin module. A capping spin module can include one nozzle that can be made to dispense the cap film coat solution onto the substrate. This solution can be dispensed through pressurizing the cylinder that stores the cap film coat solution or through a pump that precisely dispenses the required amount. In some embodiments, a pump is used to dispense around 5-8 cc of the cap coat solution onto the substrate. The substrate is spun on a vacuum chuck for 15-30 seconds and the coupling formulation is dispensed. The spin speed can be set to 2000 to 2500 rpm.

The substrates with the capping solution are baked in a cap bake module. A capping bake module is a hot plate set up specifically to receive wafers just after the capping film coat is applied. In some embodiments, provided herein is a method of baking the spin coated capping coat solution in a hot plate to accelerate the capping reaction significantly. Hot plate baking generally reduces the capping time for amino acids to less than two minutes.

The byproducts of the capping reaction are stripped in a stripper module. A stripper module can include several nozzles, typically up to 10, set up to dispense organic solvents such as acetone, isopropyl alcohol, N-methyl pyrrolidone, dimethyl formamide, DI water, etc. In some embodiments, the nozzles can be designated for acetone followed by isopropyl alcohol to be dispensed onto the spinning wafer. The spin speed is set to be 2000 to 2500 rpm for around 20 seconds.

This entire cycle can be repeated as desired with different coupling molecules each time to obtain a desired sequence.

In some embodiments, a microarray comprising a surface of free carboxylic acids is used to synthesize polypeptides in an N→C orientation. In one embodiment, the carboxylic acids on the surface of the substrate are activated (e.g., converted to a carbonyl) to allow them to bind to free amine groups on an amino acid. In one embodiment, activation of carboxylic acids on the group of the surface can be done by addition of a solution comprising a carbodiimide or succinimide to the surface of the microarray. In some embodiments, carboxylic acids can be activated by addition of a solution comprising 1-ethyl-3-(3-dimethyl-aminopropyl)-carbodiimide (EDC), N-hydroxysuccinimide (NHS), 1,3-diisopropyl-carbodiimide (DIC), hydroxybenzotriazole (HOBt), O-(7-azabenzotriazol-1-yl)-N,N,N',N'-tetramethyluronium hexafluorophosphate (HATU), benzotriazol-1-yl-oxytripyrrolidinophosphonium hexafluorophosphate (PyBOP), or N,N-diisopropylethylamine (DIEA) to the surface of the microarray. The activation solution is washed away and the surface of the microarray is prepared for addition of an amino acid layer (i.e., one amino acid at each activated carboxylic acid group). Carboxylic acid groups remain activated for up to 2, 3, 4, 5, 6, 7, 8, 9, or 10 hours.

Addition of a solution comprising an amino acid with a free amine group to the activated carboxylic acid surface of the microarray results in binding of a single amino acid to each carboxylic acid group. In some embodiments, the amino acid comprises an amino acid with protected amine groups. Using a photosensitive chemical reaction, the protecting group can be removed from the amine group of selected amino acids at site-specific locations using a reticle. For example, Fmoc-protected amino acids are mixed in a solution comprising a photobase. Upon exposure of the solution on the microarray to a specific frequency of light at site-specific locations, the photobase will release a base which will deprotect the amino acid, resulting in coupling of the amino acid to the activated carboxylic acid group on the surface of the microarray. Another method of generating a base is through the use of a photoacid generator. In some embodiments, the photoacid generator is N-boc-piperidine or 1-boc-4-piperazine.

After a completed layer of amino acids is coupled, remaining uncoupled activated carboxylic acids are capped to prevent nonspecific binding of amino acids on subsequent synthesis steps. The steps of activation, addition of an amino acid layer, and capping are repeated as necessary to synthesize the desired polypeptides at specific locations on the microarray.

In one embodiment, peptides synthesized in the N→C terminus direction can be capped with a diamine molecule to enhance binding properties of selected polypeptide sequences to a biological molecule, e.g., an antibody. In other embodiments, peptides synthesized in the C→N direction can be capped with a dicarboxylic acid molecule to enhance binding properties of selected sequences to a biological molecule.

While synthesizing polypeptides in parallel on the surface of a microarray, the method described herein ensures complete activation of carboxylic acid on the surface of the microarray. Due to stability of the activated ester for an extended period of time, 2, 3, 4, 5, 6, 7, 8, 9, 10, 11, 12, 13, 14, 15, 16, 17, 18, 19, 20, 21, 22, 23, 24, 25 or more coupling cycles may be completed after a single activation step (e.g., to couple an entire layer of 2-25 or more different amino acids at different locations on the microarray). As the coupling occurs during hard bake (heating in a hot plate at 85-90° Celsius for 90 seconds immediately after coating) and due to the presence of excess amino acid in the solution, complete 100% deprotection of Fmoc-protected amino acid may not be required for significantly high coupling yields. After addition of all amino acids and capping, all free activated carboxylic acids are either coupled or capped, thus resulting in high efficiency and accuracy of polypeptide synthesis.

Methods of Use of Microarrays

Also disclosed herein are methods of using substrates, formulations, and/or microarrays. Uses of the microarrays disclosed herein can include research applications, therapeutic purposes, medical diagnostics, and/or stratifying one or more patients.

Any of the microarrays described herein can be used as a research tool or in a research application. In one embodiment, microarrays can be used for high throughput screening assays. For example, enzyme substrates (i.e., peptides on a peptide microarray described herein) can be tested by subjecting the microarray to an enzyme and identifying the presence or absence of enzyme substrate(s) on the microarray, e.g., by detecting at least one change among the features of the microarray.

Microarrays can also be used in screening assays for ligand binding, to determine substrate specificity, or for the identification of peptides that inhibit or activate proteins. Labeling techniques, protease assays, as well as binding assays useful for carrying out these methodologies are generally well-known to one of skill in the art.

In some embodiments, a microarray can be used to represent a known protein sequence as a sequence of overlapping peptides. For example, the amino acid sequence of a known protein is divided into overlapping sequence segments of any length and of any suitable overlapping frame, and peptides corresponding to the respective sequence segments are in-situ synthesized as disclosed herein. The individual peptide segments so synthesized can be arranged starting from the amino terminus of the known protein.

In some embodiments, a microarray is used in a method wherein the antigenic representation of the microarray includes at least one region where the whole antigen sequence of a known protein is spanned via epitope sliding; the immunoactive regions of the antigen are determined by contacting one or more clinical samples on the array or a plurality of different microarrays, and the set of peptide sequences required to represent the known protein antigen are reduced.

In some embodiments, a sample is applied to a microarray having a plurality of random peptides. The random peptides can be screened and BLASTed to determine homologous domains with, e.g., a 90% or more identity to a given antigenic sequence. In some embodiment, the whole antigenic sequence can then be synthesized and used to identify potential markers and/or causes of a disease of interest.

In some embodiments, a microarray is used for high throughput screening of one or more genetic factors. Proteins associated with a gene can be a potential antigen and antibodies against these proteins can be used to estimate the relation between gene and a disease.

In another example, a microarray can be used to identify one or more biomarkers. Biomarkers can be used for the diagnosis, prognosis, treatment, and management of diseases. Biomarkers may be expressed, or absent, or at a different level in an individual, depending on the disease condition, stage of the disease, and response to disease treatment. Biomarkers can be, e.g., DNA, RNA, proteins (e.g., enzymes such as kinases), sugars, salts, fats, lipids, or ions.

Microarrays can also be used for therapeutic purposes, e.g., identifying one or more bioactive agents. A method for identifying a bioactive agent can comprise applying a plurality of test compounds to a microarray and identifying at least one test compound as a bioactive agent. The test compounds can be small molecules, aptamers, oligonucleotides, chemicals, natural extracts, peptides, proteins, fragment of antibodies, antibody like molecules or antibodies. The bioactive agent can be a therapeutic agent or modifier of therapeutic targets. Therapeutic targets can include phosphatases, proteases, ligases, signal transduction molecules, transcription factors, protein transporters, protein sorters, cell surface receptors, secreted factors, and cytoskeleton proteins.

In another embodiment, a microarray can be used to identify drug candidates for therapeutic use. For example, when one or more epitopes for specific antibodies are determined by an assay (e.g., a binding assay such as an ELISA), the epitopes can be used to develop a drug (e.g., a monoclonal neutralizing antibody) to target antibodies in disease.

In one embodiment, also provided are microarrays for use in medical diagnostics. An array can be used to determine a response to administration of drugs or vaccines. For example, an individual's response to a vaccine can be determined by detecting the antibody level of the individual by using a microarray with peptides representing epitopes recognized by the antibodies produced by the induced immune response. Another diagnostic use is to test an individual for the presence of biomarkers, wherein samples are taken from a subject and the sample is tested for the presence of one or more biomarkers.

Microarrays can also be used to stratify patient populations based upon the presence or absence of a biomarker that indicates the likelihood a subject will respond to a therapeutic treatment. The microarrays can be used to identify known biomarkers to determine the appropriate treatment group. For example, a sample from a subject with a condition can be applied to a microarray. Binding to the microarray may indicate the presence of a biomarker for a condition. Previous studies may indicate that the biomarker is associated with a positive outcome following a treatment, whereas absence of the biomarker is associated with a negative or neutral outcome following a treatment. Because the patient has the biomarker, a health care professional may stratify the patient into a group that receives the treatment.

In some embodiments, a method of detecting the presence or absence of a molecule of interest (e.g., a protein, an antibody, or any other ligand) in a sample can include obtaining a microarray disclosed herein and contacted with a sample suspected of comprising the molecule of interest; and determining whether the molecule of interest is present in the sample by detecting the presence or absence of binding to one or more features of the microarray.

In some embodiments, a molecule of interest can be detected within a sample that has a volume that is less than or equal to 100, 50, 10, 5, 1.5, or 1 µL. In some embodiments, the elapsed time from the sample contacting to detection of a molecule of interest is less than 40, 30, 20, 19, 18, 17, 16, 15, 14, 13, 12, 11, 10, 9, 8, 7, 6, 5, 4, 3, 2, or 1 minutes. In some embodiment, a molecule of interest can be detected at a concentration in the contacted sample that falls within the range of about 1 µg/ml to 1,000 µg/ml.

In some embodiments, the protein of interest may be obtained from a bodily fluid, such as amniotic fluid, aqueous humour, vitreous humour, bile, blood serum, breast milk, cerebrospinal fluid, cerumen, chyle, endolymph, perilymph, feces, female ejaculate, gastric acid, gastric juice, lymph, mucus, peritoneal fluid, pleural fluid, pus, saliva, sebum, semen, sweat, synovial fluid, tears, vaginal secretion, vomit, or urine.

In some embodiments, a method of identifying a vaccine candidate can include obtaining a microarray disclosed herein contacted with a sample derived from a subject previously administered the vaccine candidate, wherein the sample comprises a plurality of antibodies; and determining the binding specificity of the plurality of antibodies to one or more features of the microarray. In some embodiments, the features comprise a plurality of distinct, nested, overlapping peptide chains comprising subsequences derived from a source protein having a known sequence.

Remote Microarray Analysis

Figure 6:
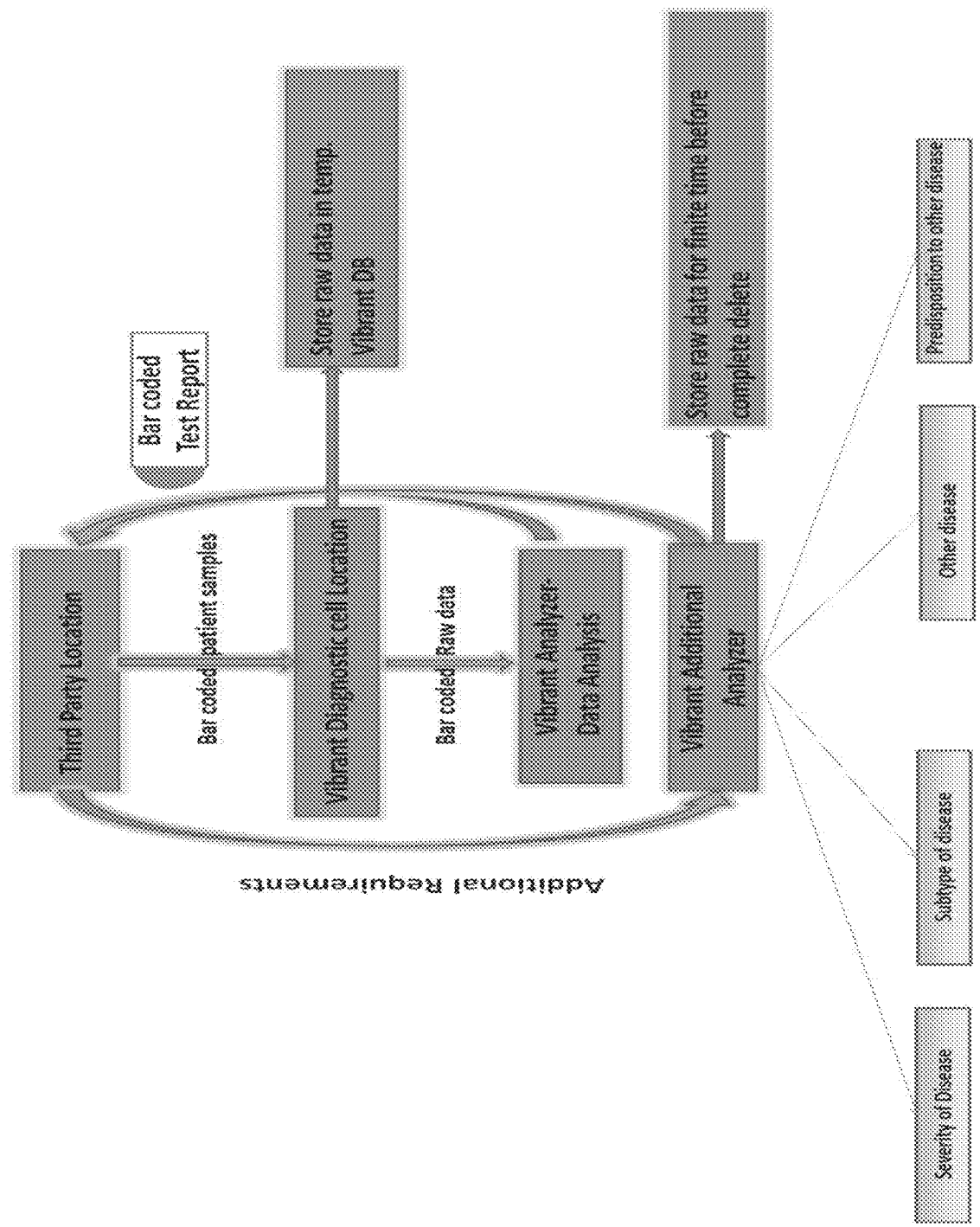
FIG. 6 shows a flow diagram depicting one embodiment of the diagnostic model provided herein, according to one embodiment.

In some embodiments, a diagnostic device comprising a chip array is located in a third party location (e.g., a reference lab or a diagnostic lab). In some embodiments, the assay is performed in one or several of the third party locations and the patient samples are barcoded. The raw data output from the chip array is input into an analyzer at a user-controlled location. This transfer may be through a VPN or via any other remote data transfer method. In some embodiments, the raw data is stored in a temporary user-controlled database for a finite time. A test report is generated and the results are provided to the third party. Any additional information requested by the third party may also be provided from additional analysis of the stored raw data. A flow diagram depicting one embodiment of the diagnostic model provided herein is shown in FIG. 6.

In some embodiments, the analysis provides information on, for example, disease presence, disease severity, subtype of disease, the presence and/or identity of multiple diseases and/or predisposition to diseases. In some embodiments, the analysis provides information from multiplexing different antibody tests, multiple analytes from the same disease, multiplexing tests for different diseases. In some embodiments, the assay is an antibody-antigen interaction assay, a peptide-peptide interaction assay, a peptide-protein interaction assay, a protein-protein interaction assay, or a kinase interaction assay. In some embodiments, the assay station is a fully or semi-automated robotic liquid handling station.

In some embodiments, after the test is complete, the raw data with no bar-code that never can be retraced is stored in a user-controlled database (one way storage). This non-retraceable raw data will be used to study the variability of the specific tests across populations and also see the correlation between different antigenic peptide analyte in designed-set to determine limits for the controls.

In some embodiments, a yearly subscription is provided to trend a set of key antigenic peptides representing different diseases to build a self-baseline for individual patients. In one embodiment of this method, the same person is tested on the same set of designed antigenic peptides that are biologically relevant or molecular mimicry, at different time frame to trend whether or not a predisposition or early detection of a diseases to identify the trend change with solid evidence of key disease related antigenic-peptides move from self-baseline and light up even to slightly higher level from the trend-range. Any improvements to the trending subscription based designed-set will always have the legacy of the earlier designed-set so the continuity to trend of the same person is not lost, but improved with new addition to reflect progress in diagnostics.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ *Ed.* (Plenum Press) Vols A and B(1992).

Example 1: Multiple Linker Molecules for Protein, Peptide, or Antibody Attachment to a Single Chip This example describes the structure of selected linker molecules for attachment to a chip. The linker molecules will attach ("link") a protein, peptide, or antibody to the chip. The structure of the linker molecule will affect the attachment of the protein, peptide, or antibody to the chip and affect the binding affinity of the protein or antibody to other proteins, peptides, or antibodies.

Figure 7:
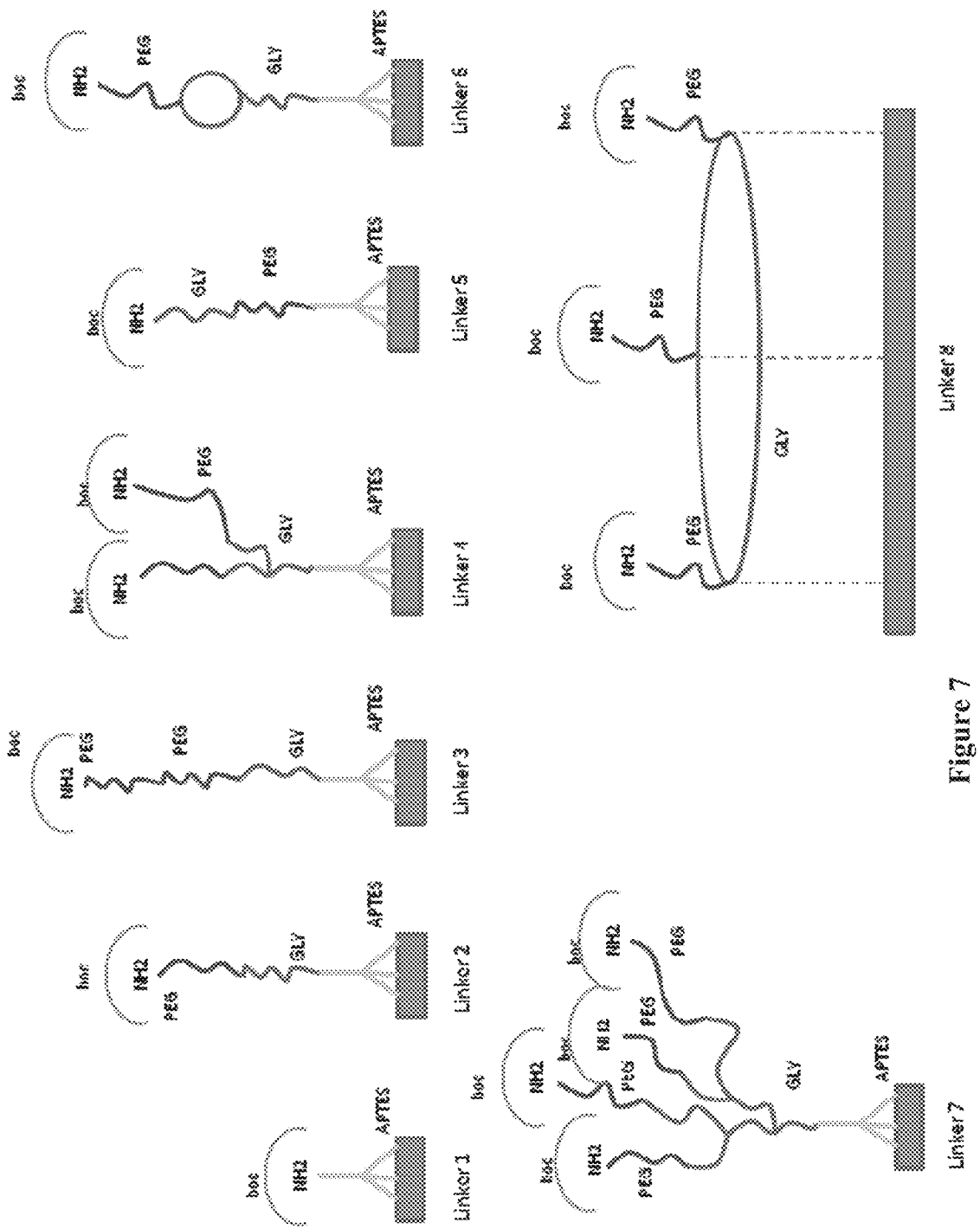
FIG. 7 shows the structure of linker molecules, including e.g. polyethylene glycol (PEG), glycine (GLY) linker chain and a protecting group of tert-Butyloxycarbonyl (boc), attached via 3-amino-triethoxysilane (APTES) on a single chip for linking a peptide or protein to the surface of the chip to the unprotected $NH_2$ group, according to one embodiment.
Figure 8:
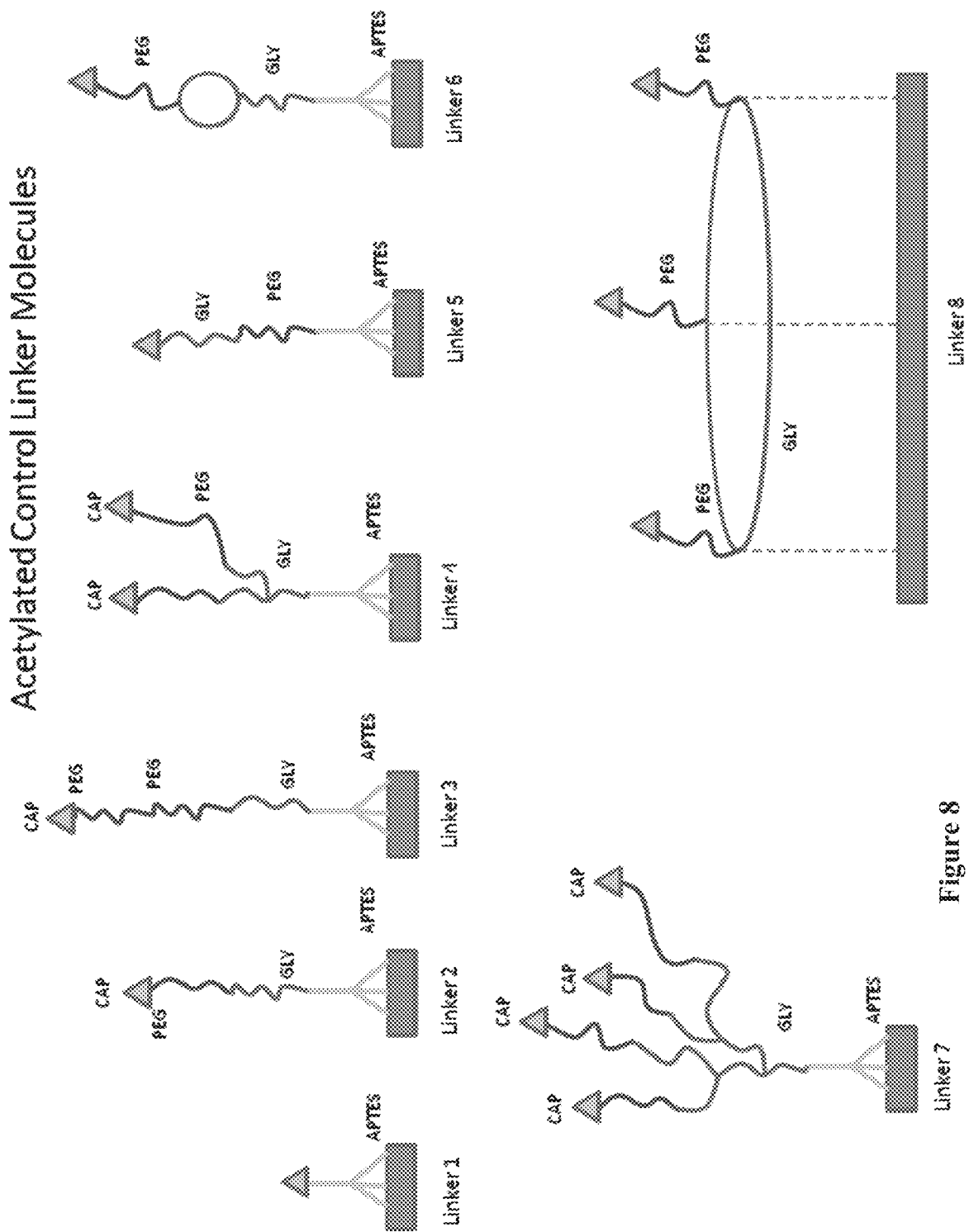
FIG. 8 shows control linker molecules that are the acetylated (CAP) versions of the linker molecules from FIG. 7, according to one embodiment.
Figure 9:
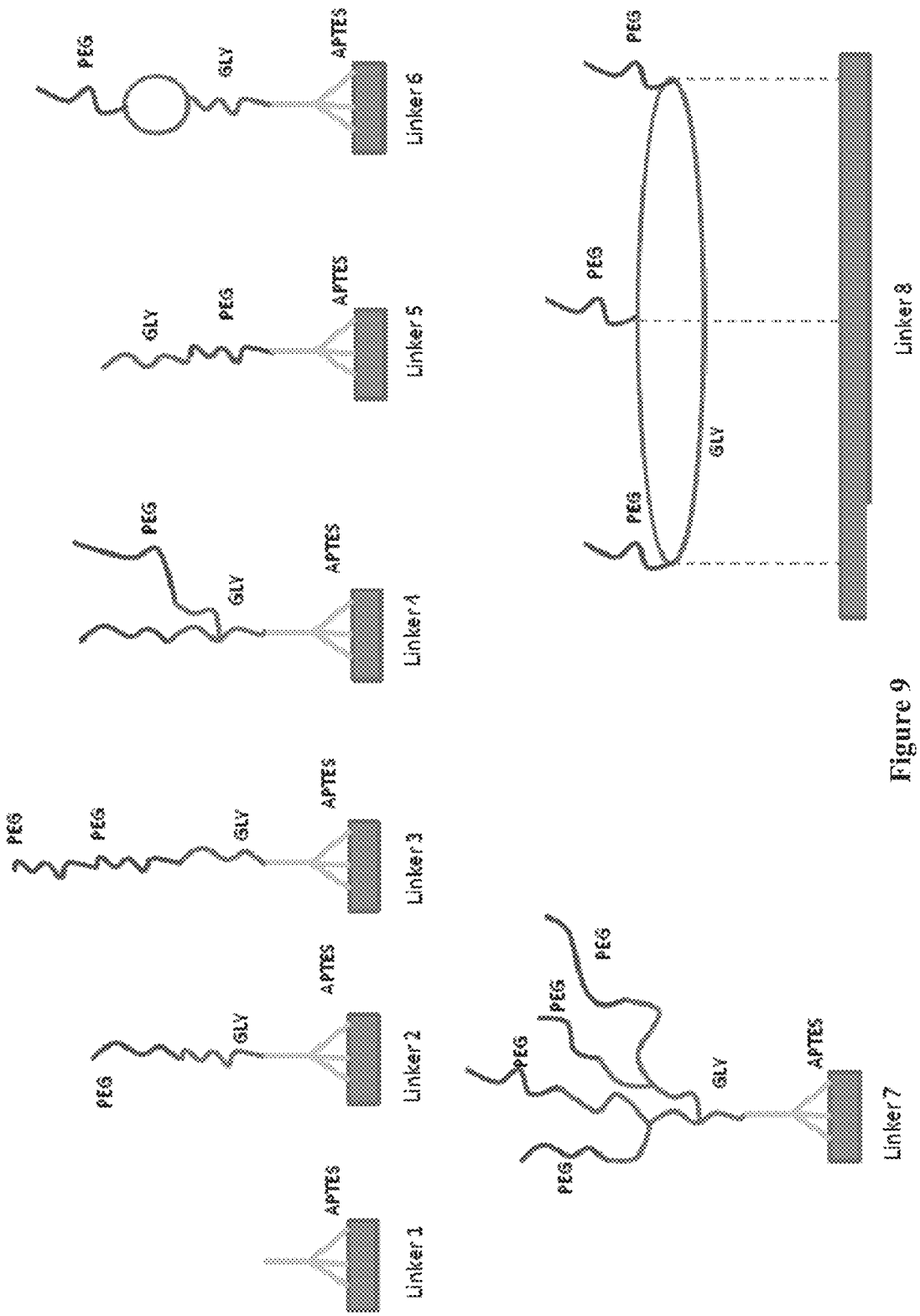
FIG. 9 shows the deprotected linker molecules, i.e. after removing the boc group and leaving the $NH_2$ group unprotected (not shown), of FIG. 7, according to one embodiment.

Silicon wafers were obtained from University wafers. A thin film of Nickel about 1000 Angstrom thick was deposited on the wafers using plasma-enhanced chemical vapor deposition (PECVD). This was followed by PECVD deposition of 500 Angstrom thick layer of nitride. The nitride was silinated using aminopropyl triethoxysilane (APTES) (FIG. 7, Linker 1). This silination step was immediately followed by coupling of a boc-protected Gly-PEG linker chain (FIG. 7, Linkers 2-8), where Gly represents a Glycine linker chain, and PEG represents polyethylene glycol. The coupling was performed using simple Merrifield chemistry. Multiple other linker molecules can be attached onto a microarray to bind other peptides or proteins. Eight examples of linker configurations are shown in FIG. 7. Linker 1 is silane-(boc), where (boc) represents a tert-butyloxycarbonyl protecting group. Linker 2 is silane-Gly-PEG(boc). Linker 3 is silane-Gly-PEG-PEG(boc). Linker 4 is silane-Gly-(PEG(boc))$_2$. Linker 5 is silane-PEG-Gly(boc). Linker 6 is silane-Gly-cyc-PEG(boc), where Gly-cyc represents a glycine chain with a cyclic glycine chain conformation. Linker 7 is silane-Gly-(PEG(boc))$_4$. Linker 8 is cyclic peptide loop formed by side chains of multiple Lysine and Glutamic acid molecules. The use of multiple different linker molecules for the same protein allows one to determine the affinity and avidity of the biological interactions. Linker molecules are not limited to this example, but can include, e.g. multiple lysine branches that are used to attach a protein or peptide to the silicon wafer chip. FIG. 8 shows the control acetylated (CAP) versions of the linker molecules from FIG. 7. FIG. 9 shows the unprotected control linker molecules of FIG. 7 without the tert-butyloxycarbonyl protecting group.

Example 2: Coupling of Anti-p53 Antibody and IL-6 Protein to a Chip

Figure 10:
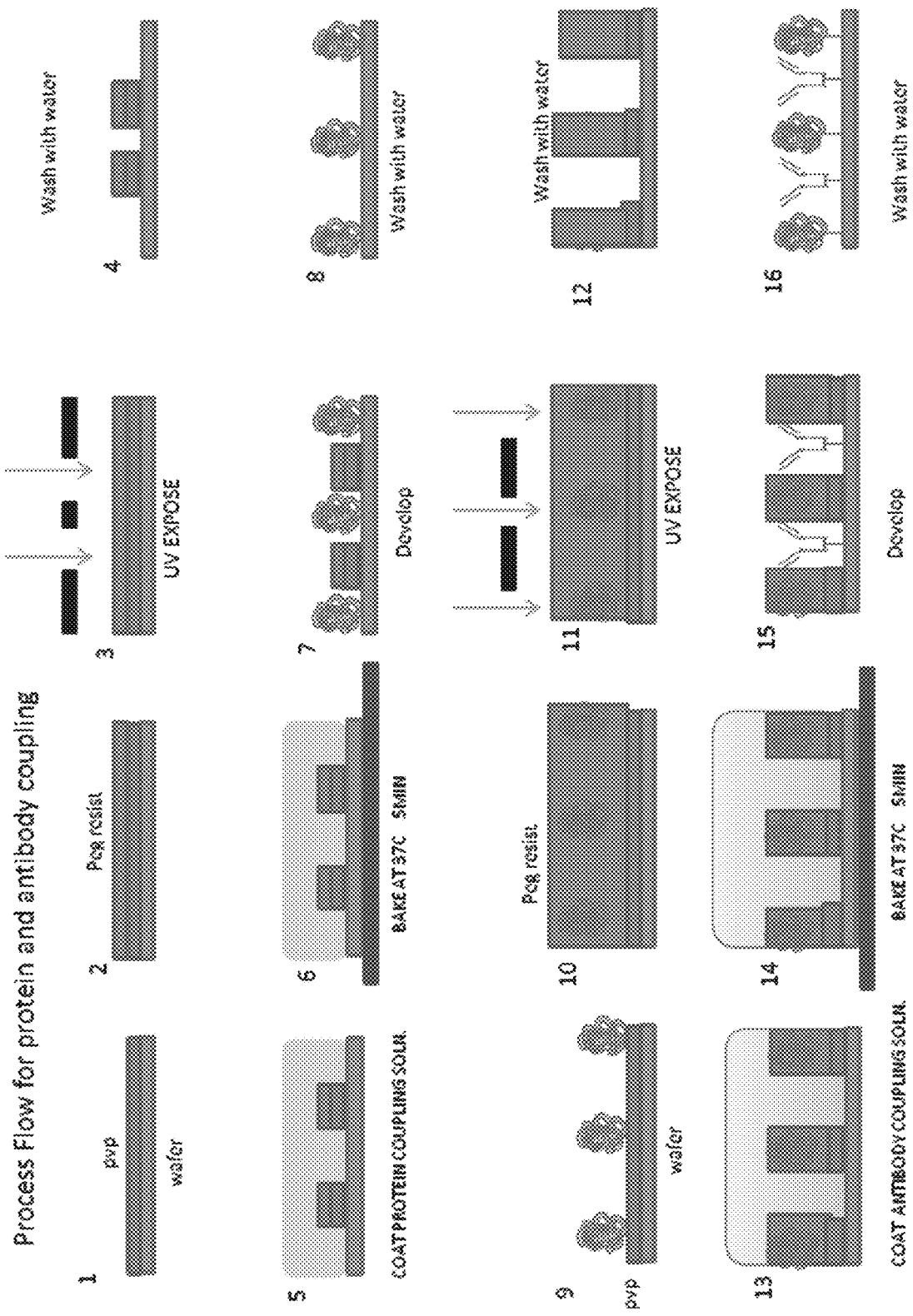
FIG. 10 shows a step by step process for adding a protein, e.g. IL-6, and an antibody, e.g. p53 antibody, to a chip, according to one embodiment.
Figure 11:
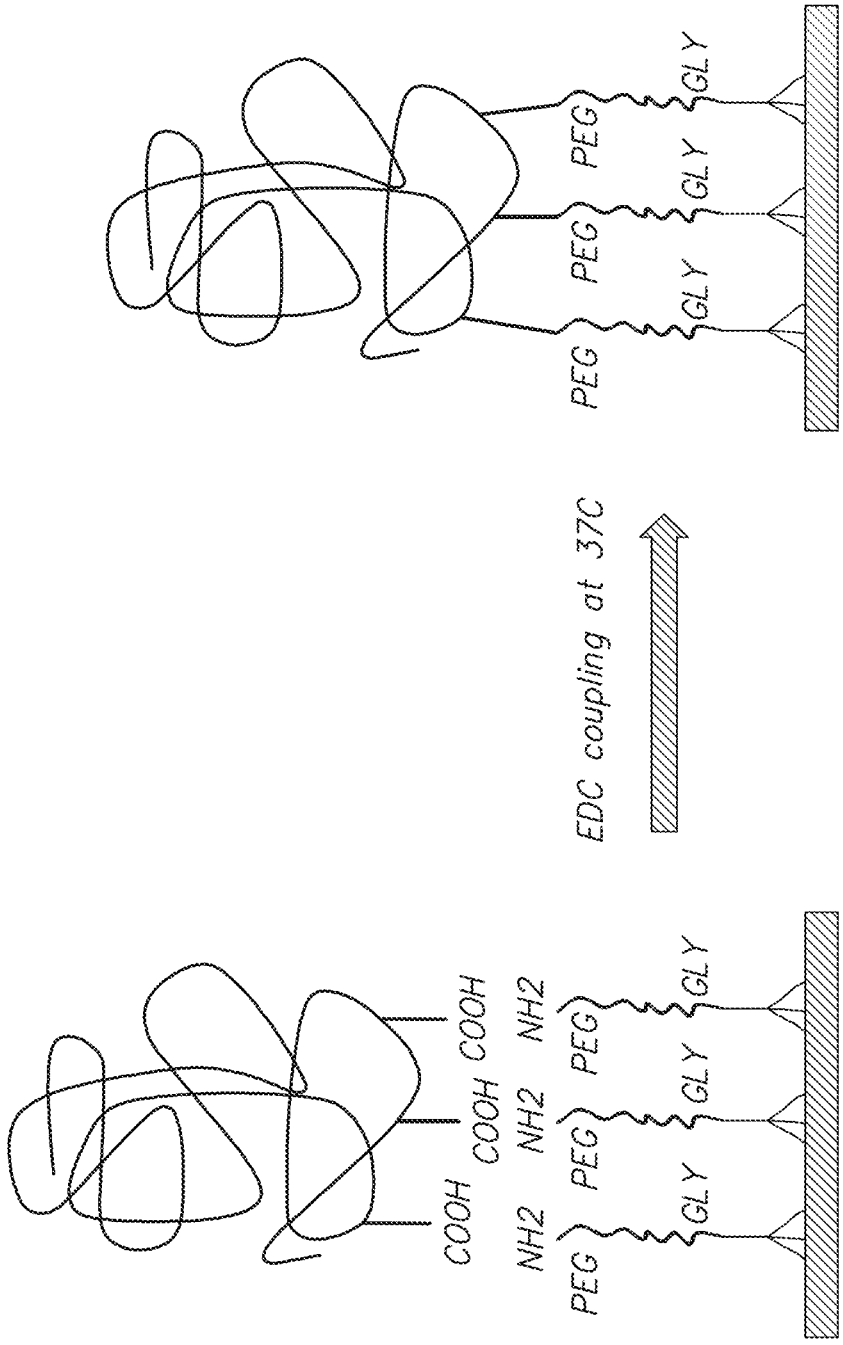
FIG. 11 shows the binding of protein to linker molecules attached to the surface of a chip via 1-ethyl-3-(3-dimethyl-aminopropyl)-carbodiimide (EDC) coupling, according to one embodiment.

A wafers was first coated with the desired linker molecules from Example 1 and a solution of 10% by weight polyvinylpyrrolidone (PVP) in water (FIG. 10, Step 1), followed by covering with a 5% Polyethylene glycol (PEG) based photoresist (FIG. 10, Step 2) and subsequent exposure with light from a Nikon NSR 203 at 50 mJ/cm$^2$ (FIG. 10, Step 3). After exposure the wafers were developed with water (FIG. 10, Step 4). The exposed areas were cross-linked while the non-exposed areas were developed with water. The features of multiple different linkers were used for coupling the IL-6 protein (FIG. 10, Step 5), wherein IL-6 protein coupling solution was prepared as follows: 0.05 mg/ml of IL-6 protein is dissolved in water along with 1 mg/ml of 1-ethyl-3-(3-dimethylaminopropyl) carbodiimide (EDC) and 10% by weight of PVP. This coupling solution was then spin coated at 1000 rpm onto the wafer to obtain a uniform coat. The wafer was then baked at 37° Celsius for 5 minutes in a hot plate (FIG. 10, Step 6). Alternatively, the coupling solution was dispensed and the wafer is stored at 4° Celsius overnight to complete the protein coupling to the linker molecules. Next, the wafer was washed with water to strip the polymeric coat (FIG. 10, Step 8). This completed the coupling of the first protein to the wafer. Since there are multiple types of linker molecules, the IL-6 protein was available at varying concentration to determine the affinity and avidity of biological binding. The binding of the protein to linker molecules attached to the surface via EDC coupling is shown in more detail in FIG. 11.

Figure 12:
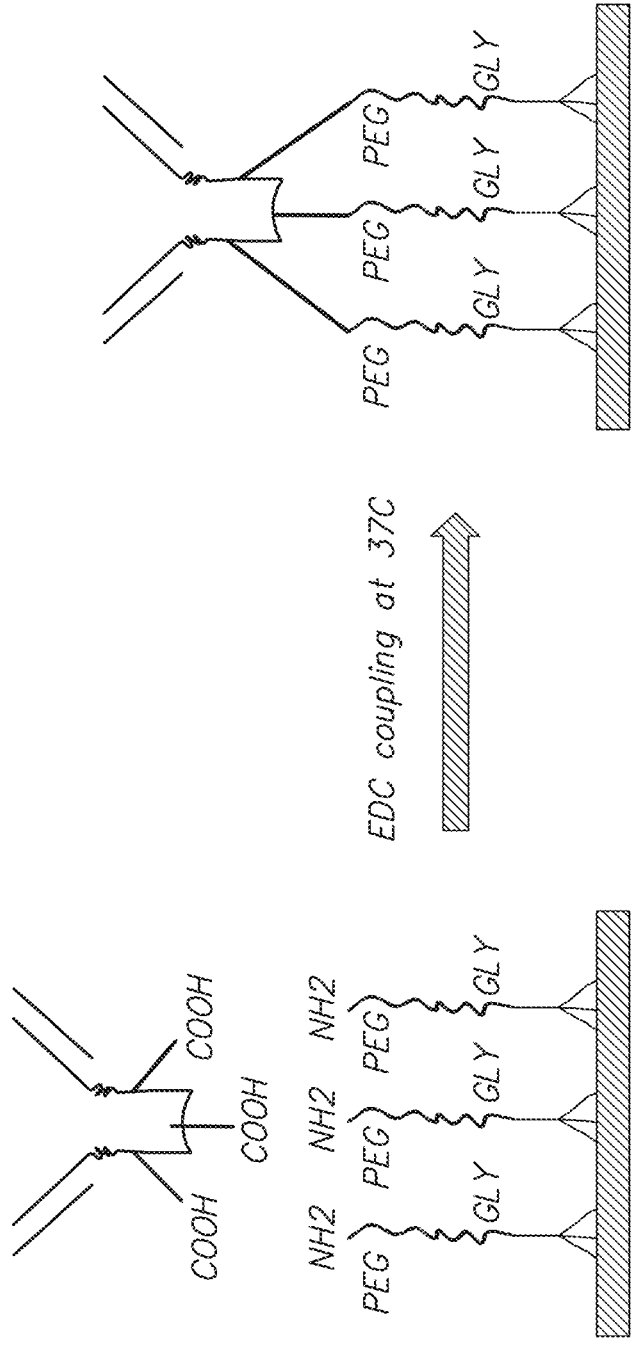
FIG. 12 shows the binding of antibody to linker molecules attached to the surface of a chip via EDC coupling, according to one embodiment.

Now the wafer was coated with 10% by weight PVP in water (FIG. 10, Step 9) followed by 5% by weight PEG-based photoresist (FIG. 10, Step 10) before exposure with light from a Nikon NSR 203 at 50mJ/cm$^2$ (FIG. 10, Step 11). After exposure the wafer was developed with water (FIG. 10, Step 12). The exposed areas were cross-linked while the non-exposed areas were developed with water. Now the wafer was spin coated with a p53 antibody coupling solution (FIG. 10, Step 13). p53 antibody coupling solution consisted of 0.05 mg/ml of p53 antibody in water along with 1 mg/ml of EDC and 10% by weight of PVP. This coupling solution was spin coated at 1000 rpm to obtain a uniform coat. The wafer is then baked at 37° Celsius for 5 minutes on a hot plate (FIG. 10, Step 14). Alternatively, the p53 antibody coupling solution was dispensed and the wafer is stored at 4° Celsius overnight to complete the antibody coupling to the linker molecules. Next, the wafer was washed with water to strip the polymeric coat (FIG. 10, Step 16). This completed the coupling of p53 antibodies. Since there are multiple types of linker molecules, the same p53 antibody was available at varying concentration to determine the affinity and avidity of biological binding. The binding of the antibody to linker molecules attached to the surface via EDC coupling is shown in more detail in FIG. 12.

Using the method described above, multiple different proteins can be coupled to a wafer in a high throughput method. The wafers were then diced into small chips of a size of 1 mm by 1 mm. The diced chips were placed into the wells of a 364-well plate.

Example 3: Chip Array with Well Plates Using PDMS Film

Figure 13:
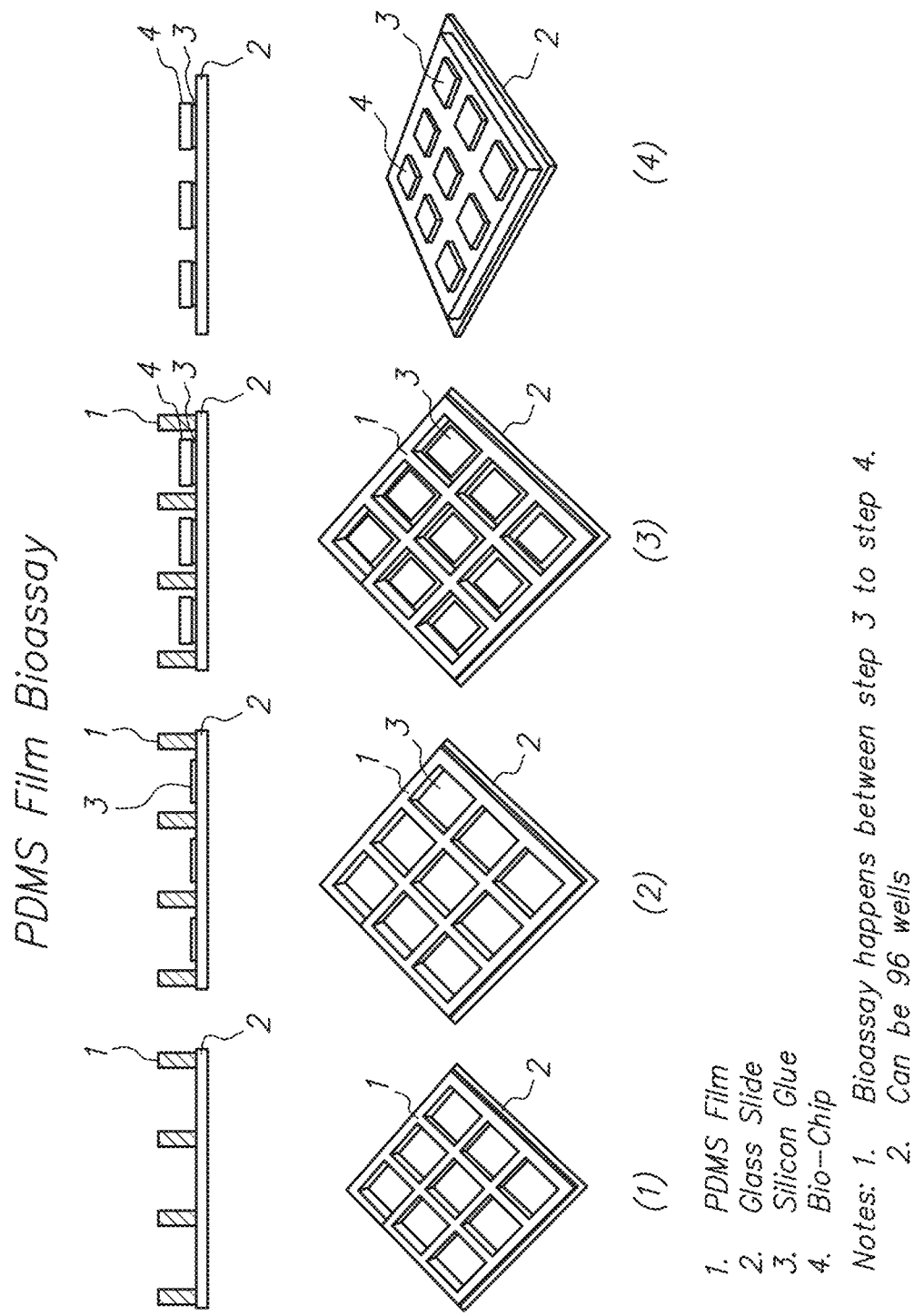
FIG. 13 shows a process of performing steps in an assay using a polydimethyl-siloxane (PDMS) film well plate and each well holding a chip, according to one embodiment.
Figure 14:
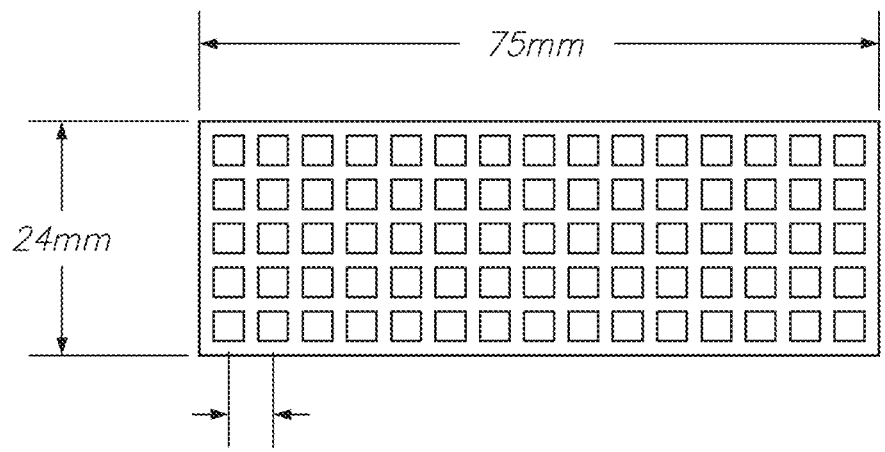
FIG. 14 shows a top view of a PDMS film well plate, according to one embodiment.
Figure 15:
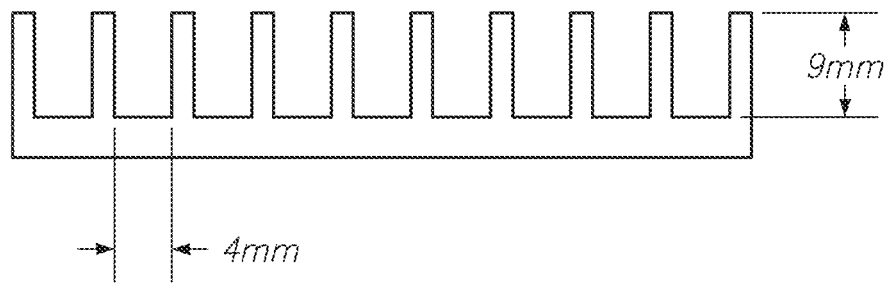
FIG. 15 shows a side view of a PDMS film well plate, according to one embodiment.

A glass slide, 1 inch by 3 inch in size, of borosilicate was obtained from VWR International. The thickness of the glass slide was 1.2 mm. A PDMS film with a minimum depth of 5 mm and a maximum depth of 9 mm was attached to the glass slide after plasma treatment of the glass slide. The thickness of the well walls was 1 mm. In this example, the size of the chip was 20 mm by 20 mm with the wells sizes measuring 4 mm by 4 mm. The edges were flat in this example. In an alternative example, the edges were tapered so that the film can easily be stripped off from the glass slide by manual or machine peeling. Subsequently, epoxy glue, EPO-TEK 301 from Epoxy Technology, was applied to the glass slide inside the wells where the chips were to be attached. With a pick-and-place robot or manually, the chips were placed on top of the epoxy glue and cured at room temperature for 24 hours. The same procedure was applied to the chips placed in the other wells. Now the glass slides were placed into frames of a standard 384-well plate and snapped on tight. The process for developing this chip array is shown in FIG. 13. A top view of the array of wells for holding chips produced by the process above is shown in FIG. 14. A side view of the chip array of wells is shown in FIG. 15. To perform a bio assay, the chip arrays were fed into a Hamilton Robotics liquid assay station. Once the wash and dry steps were completed in this assay station, the PDMS film was peeled off either manually or using a robot. The chips were then scanned to determine the results of the assay.

Example 4: Chip Array with Well Plates Using Inverted Plate Pillars

A polypropylene standard 24-, 96- or 384-well plate is used. The plate lid was a custom made injection molded using stainless steel to achieve a flatness of around 10 μm on the base and on top of the plate pillars. The diagram in FIG. 16 shows an example of the required configuration. Part 1 is a typical well plate. Part 2 is an inverted lid with plate pillars to hold the chips. The chips can either be attached to these plate pillars using epoxy glue or using part 3. In both cases, the chips were bonded tight to the substrate. In a typical liquid assay station, the wells were first filled with the required buffer solutions. Then a pick-and-place robot handled the plate lid and immerses the chips exactly into the desired wells. The height of the plate pillars was around 2-3 mm whereas the depth of the wells was around 5-6 mm so that the required amounts of buffer solution or samples when added did not spill over to the neighboring well. This amount was determined to be 100 μl. After the entire bio assay procedure was completed, the plate lid is turned upside down so the chips face upwards and were then dried using a purge of nitrogen. The chips were then scanned in a confocal scanner microscope. The stage of the confocal scanner microscope has the capability to hold the frame of a standard well plate. Multiple chips can be scanned using this set up.

Example 5: Chip Loading onto Caps and Cap Attachment to Plate Pillars

Figure 17E:
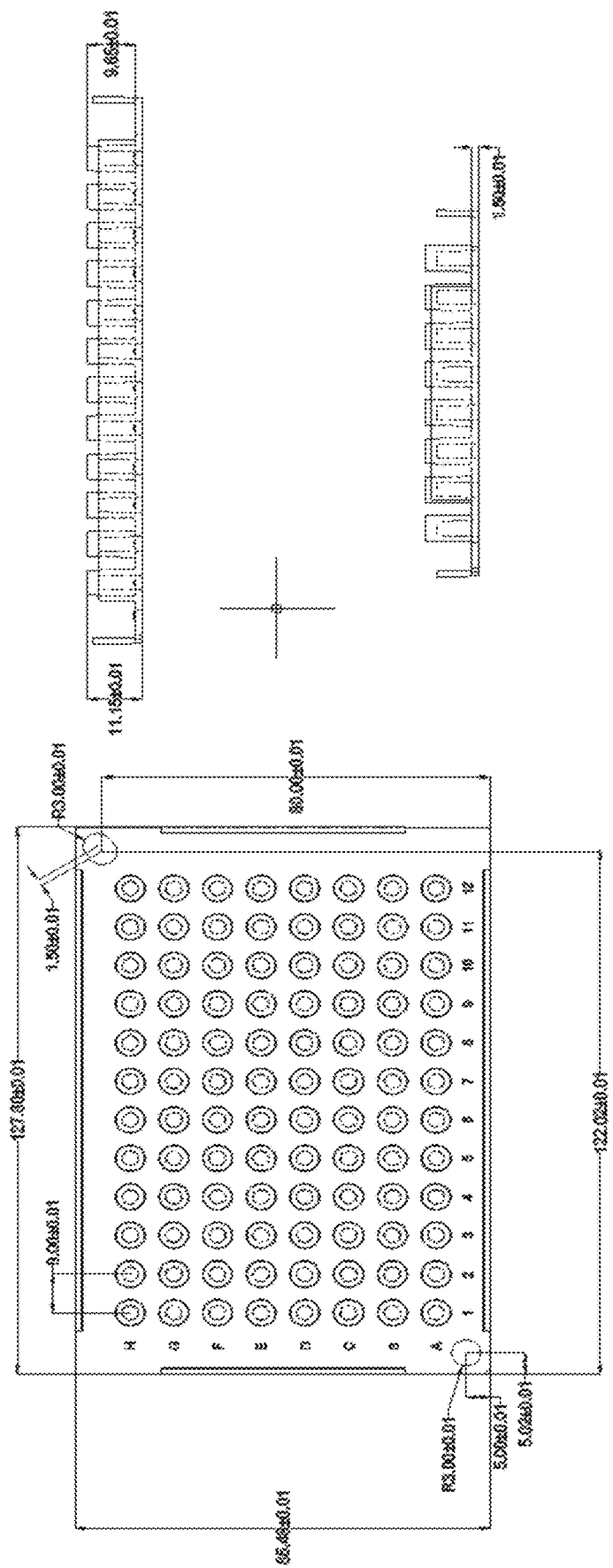

In this example, each wafer was coupled with only 1 protein using the methodology described in Example 2 above. For example, one 9 square inch wafer coupled with protein was diced into 1 mm×1 mm chips, resulting in approximately 52,000 chips carrying the same protein, e.g. p53 protein. The wafer can also be diced into chips of sizes ranging from 0.5 mm$^2$ to 10 mm$^2$. The protein chips were assembled onto protein chip caps, as shown in FIG. 17A. A plate with plate pillars as shown in FIG. 17B interfaces with the caps, allowing each cap to snap onto each plate pillar. The top of the caps consist of a plurality of chip holders with each chip. The minimum spacing between the chip holders ranges from approximately 0.25 mm to approximately 5 mm. A chip was mounted on a cap using a high throughput automated surface mount technology (SMT) pick-and-place machine. The plate pillars with caps mounted are shown in FIG. 17C. The maximum of components per hour (cph) that can be mounted via the SMT pick-and-place machine ranged from about 20,000 cph to about 150,000 cph. The resulting caps with mounted multiple protein chip arrays can be used for example with a 24-pillar or 96-pillar plate for a binding affinity assay (i.e., a serum assay). Example dimensions of a 24-pillar and 96-pillar plate are shown in FIGS. 17D and 17E, respectively.

Example 6: Assay Probing Anti-p53 Antibody and IL-6 Protein on Chip Array

The pillar plates holding protein chip arrays (as described above) were used in a serum assay to determine antibody and protein binding. For the assay sample serum is added to a chip with immobilized p53 antibody and IL-6 according to Example 2 following the general steps of: First, the chips were washed in Phosphate Buffered Saline with Tween-20 (PBST) thrice while gentle shaking the solution. Then, the chips were incubated with serum from different patients in a 384-well plate at 37° Celsius. Subsequently, the chips were washed thrice with PBST before incubating the chips with secondary antibodies to detect the target antibody-antigen binding. The chips were again washed thrice with PBST before scanning the chips in a Nikon AIR confocal or CCD scanner microscope.

The scanner microscope included a CCD camera with an image chip that has a 2048×2048 pixel resolution and frame size of 1 mm×1 mm. The frame rate of the CCD camera can be adjusted within the range of 15-30 frames/second, and typically set at 30 frames/second. To complete the data acquisition during a scan 16 frames were line integrated to yield one shot of the scanned area. The fluorescence probes attached to the secondary antibodies were each excited at wavelengths of 488 nm and 470 nm with the emission wavelengths of 525 nm and 670 nm, respectively. This allowed for the detection of two different antibodies each carrying a different fluorescence probe. To eliminate for example detection at the wavelength of 670 nm a band-pass filter in the wavelength range of 550±5 nm can be employed to filter out the emission at 670 nm. In order to distinguish among different features on a chip a resolution of 4×4 pixels per feature is used. The results of the assay are shown in FIGS. 18-22.

Figure 18:
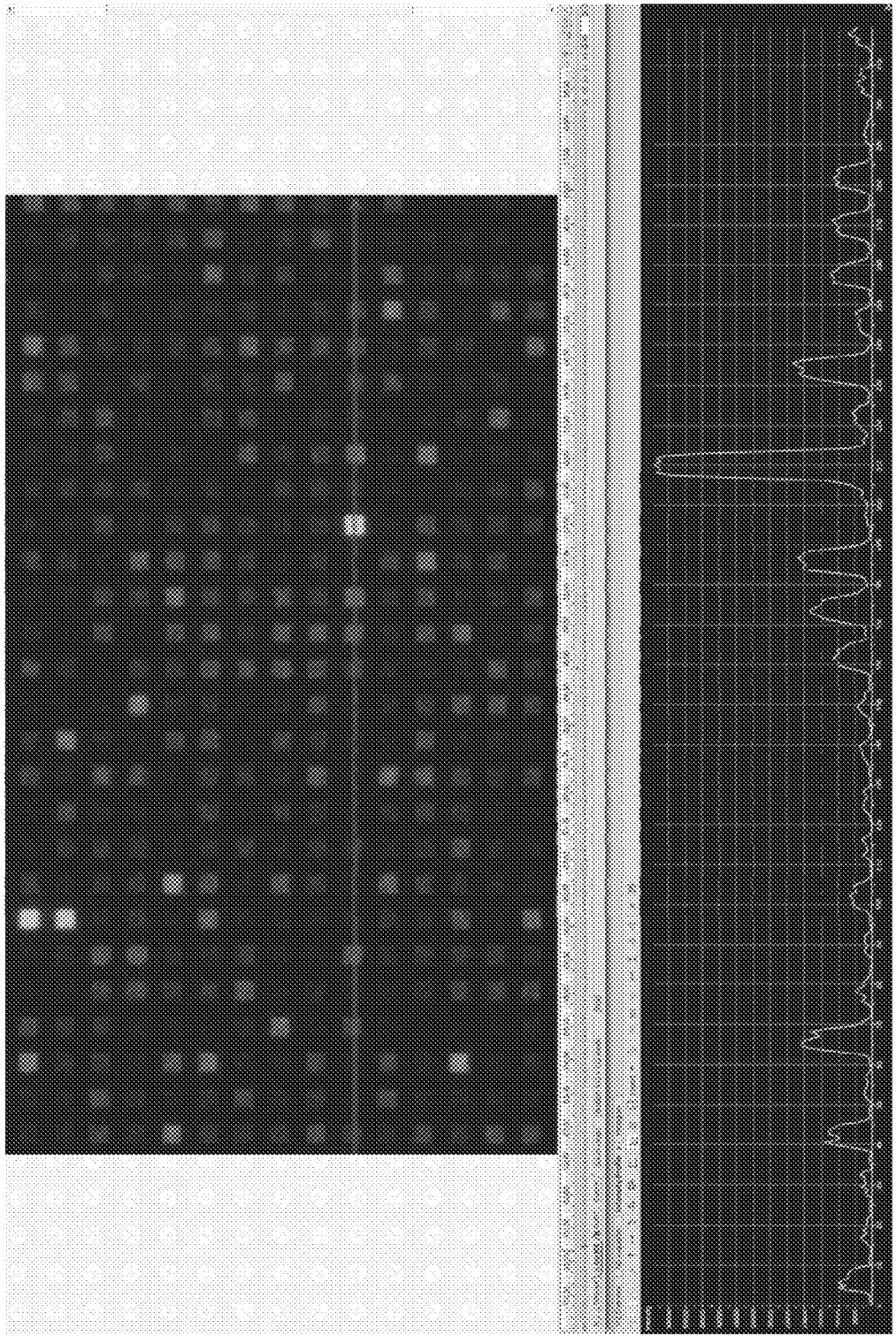
FIG. 18 shows results of an assay using a chip comprising IL-6 proteins immobilized to the chip surface with different linker molecules placing the IL-6 proteins at various distances from the chip surface, according to one embodiment.

FIG. 18 shows the results of an assay using a chip comprising IL-6 immobilized to the surface of the chip with different linker molecules, as described in Example 2. Recombinant IL-6 and polyclonal antibodies with a high binding affinity for IL-6 were obtained from Life Technologies. The variation in binding affinity of anti-IL-6 antibody to IL-6 was tested across multiple types of linkers on a single chip. IL-6 was coupled to the chip as explained in Example 2. Polyclonal rabbit antibody to human IL-6 was added to the chip at a dilution of 1:1000 in PBS. The secondary antibody which binds to the IL-6 antibody was goat anti-rabbit alexafluor 488. The chip was incubated in the dark for 1 hour to allow for the antibody to bind. FIG. 18 confirms IL-6 protein binding to multiple linker molecules on the chip. The linking sites with the highest binding affinity are ones with 4 PEGs attached to Gly.

Figure 19:
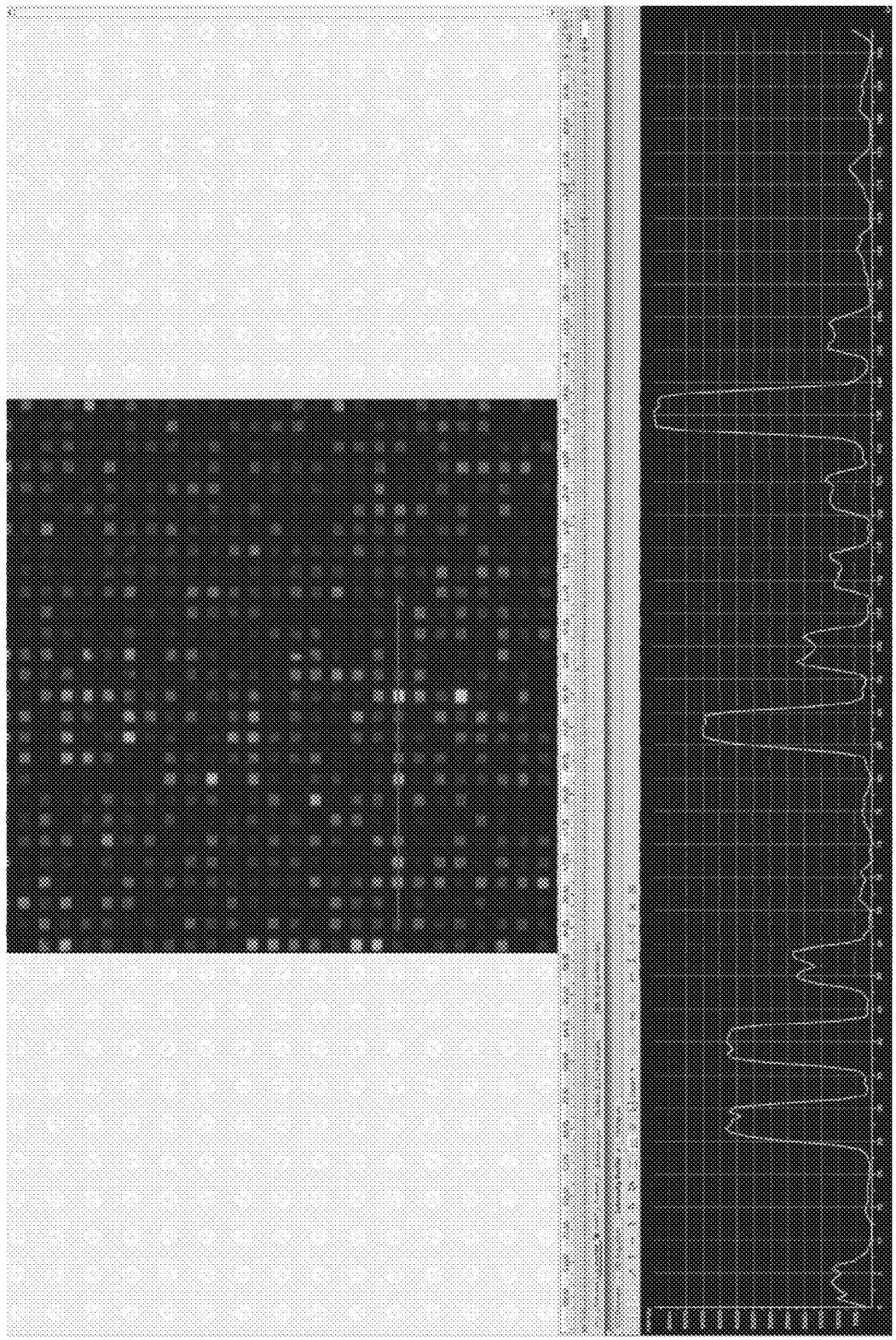
FIG. 19 shows results of an assay using a chip comprising IL-6 proteins immobilized to the surface of the chip with different linker molecules, also including acetylated linker molecules as negative controls, according to one embodiment.

FIG. 19 shows the results from an assay with a serum comprising anti-IL-6 antibodies performed on protein array chips with immobilized p53 antibody and IL-6 as described above. The binding regions showed similar results as seen in FIG. 18. The acetylated control linkers showed none or minimal binding and the linker molecules with the largest number of $NH_2$ groups displayed the highest binding affinity.

Figure 20:
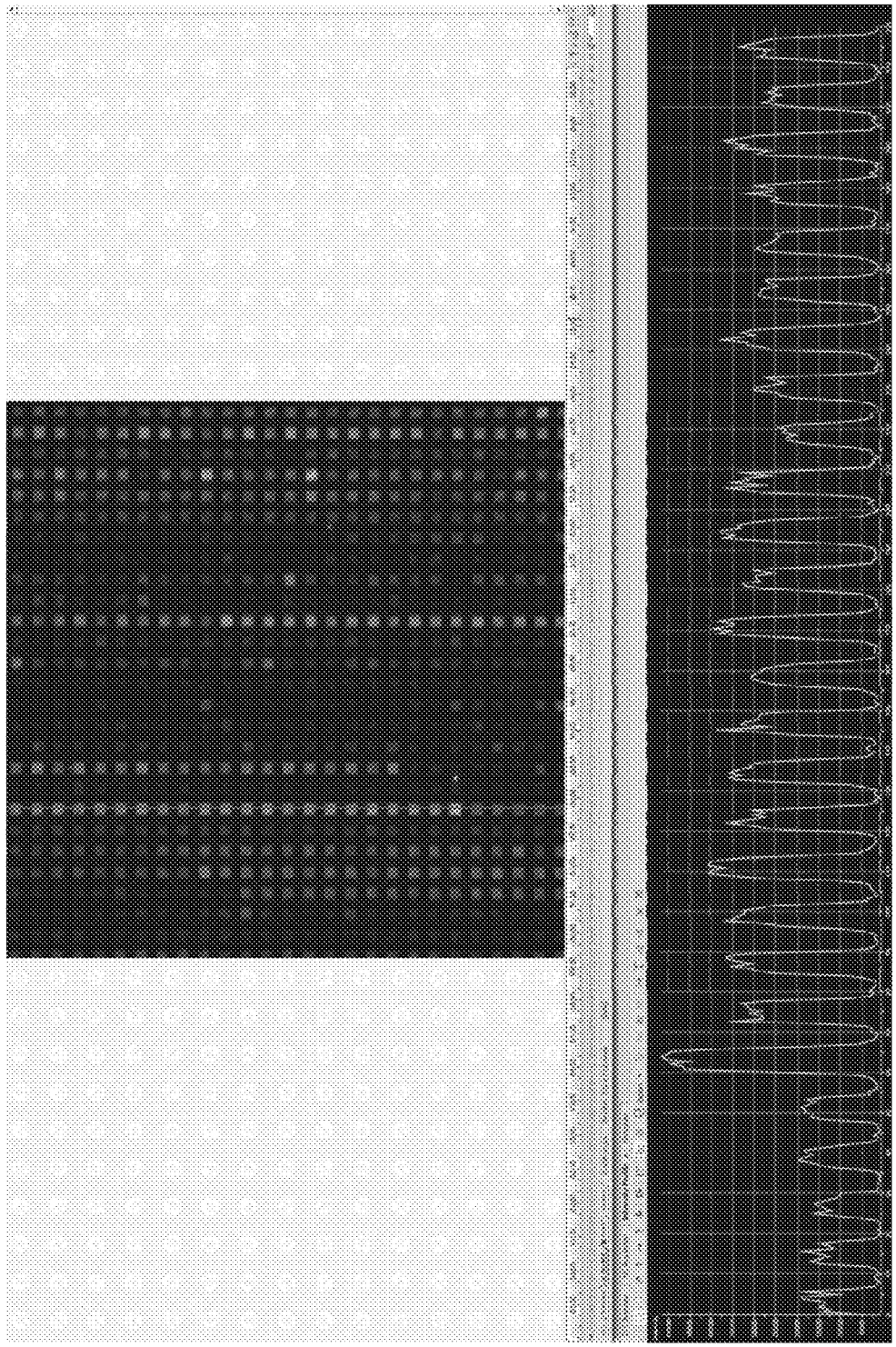
FIG. 20 shows results of an assay using a chip comprising p53 antibodies immobilized to the chip surface with different linker molecules placing the p53 antibodies at various distances from the chip surface, according to one embodiment.

FIG. 20 shows the results of an assay using a chip comprising anti-p53 antibodies. Anti-p53 polyclonal mouse antibody and recombinant human p53 protein were obtained from ABCAM. The variation in binding of anti-p53 antibody to p53 protein is tested across multiple linker molecules attached to a single chip. Anti-p53 antibody was coupled to the chip as described in Example 2. Polyclonal mouse antibody to human p53 protein was added at a dilution of 1:1000 in PBS. The secondary antibody is goat anti-mouse alexafluor 488. The chip was incubated for 1 hour in the dark to allow for the antibody binding. The results shown in FIG. 20 confirmed that anti-p53 antibody binds to multiple linker molecules attached to the chip. The highest binding affinity of anti-p53 antibody was observed at sites that include linker molecules with 4 PEGs attached to Gly.

Figure 21:
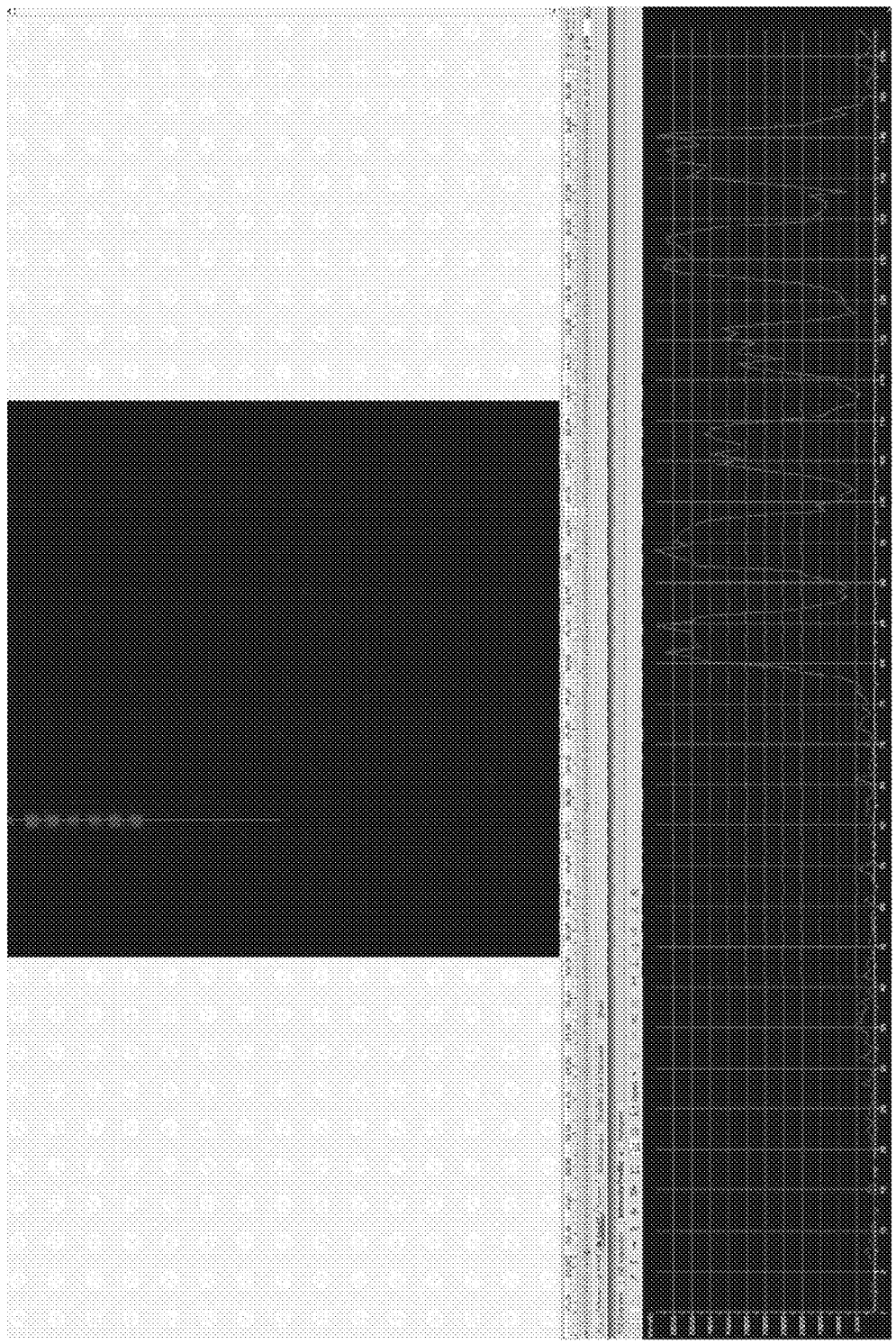
FIG. 21 shows results of an assay using a chip comprising p53 antibodies immobilized to the chip surface with different linker molecules, also including acetylated linker molecules as negative controls, according to one embodiment.

FIG. 21 shows results from the assay with p53 protein serum performed on protein array chips with immobilized p53 antibody and IL-6 as describe above. The binding regions showed similar results to those observed in FIG. 20. The acetylated control linkers showed none or minimal binding and the linker with regions having the largest number of $NH_2$ groups showed the highest binding affinity.

Figure 22:
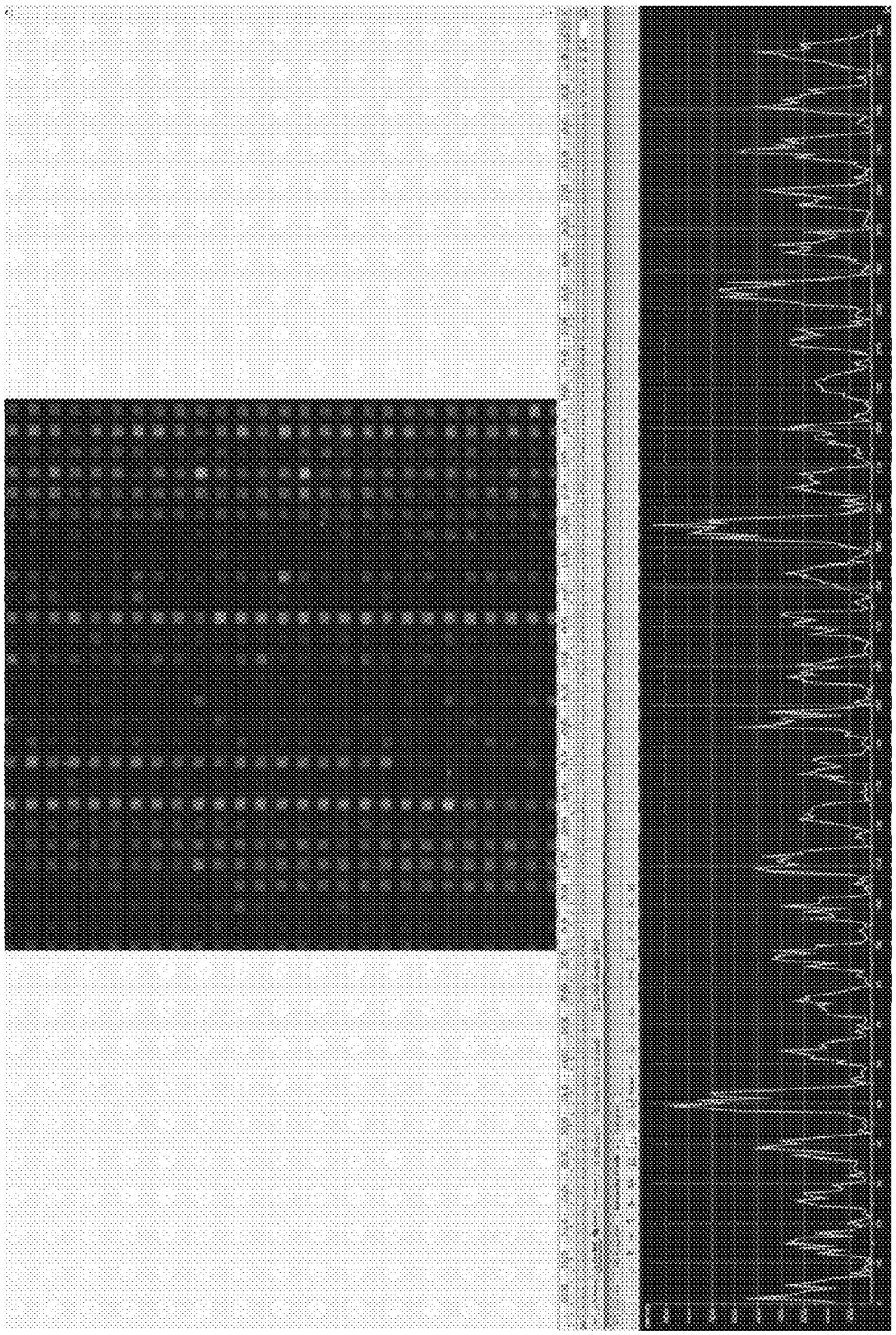
FIG. 22 shows minimal binding to the acetylated control linker molecules, according to one embodiment.

FIG. 22 shows only minimal binding to control acetylated linker molecules when no protein or antibody are attached to any of the linker molecules attached to the chip.

Figure 23:
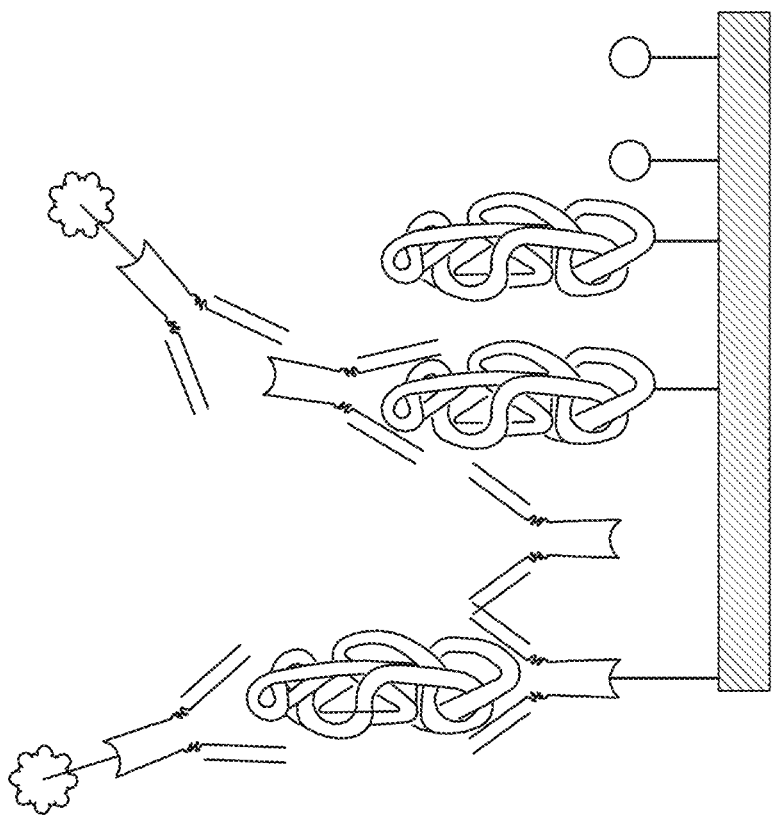
FIG. 23 shows an example of an assay using different linker molecules immobilizing selected antibodies and/or proteins to the chip surface, according to one embodiment.

A diagram of the assay illustrating the various binding events is shown in FIG. 23. When the serum was applied to the chip, both the protein and the antibody bound to the corresponding molecules coupled to the chip. Secondary antibodies comprising a fluorophore were used to detect the binding of the protein or antibody to the antibody or protein originally immobilized onto the chip surface via linker molecules.

Example 7: Assay Probing IL-6 Protein on 96-Pillar Plate

In this example, the assay protocol includes 96 chips, each sized 10 mm×10 mm and mounted on a separate pillar of a 96-pillar plate. For the assay TBS buffer, PBST buffer and BSA were obtained from VWR International and antibodies were obtained from ABCAM. Six 96-well plates were prepared beforehand with well plate no. 1 containing methanol, well plate no. 2 containing TBS buffer, well plate no. 3 containing primary antibody, well plate no. 4 containing PBST buffer, well plate no. 5 containing secondary antibody and well plate no. 6 containing DI water.

A 96-pillar plate containing the chips was consecutively placed in well plate no. 1 for 5 minutes, in well plate no. 2 for 5 minutes, in well plate no. 3 and incubated at 37° Celsius for 30 minutes, in plate no. 4 for 5 minutes, in well plate no. 5 and incubated at 37° Celsius for 30 minutes, in well plate no. 5 for 5 minutes and in well plate no. 6 for 5 minutes for a total assay time of 85 minutes.

The benefits of this assay process include: The overall assay time was reduced by avoiding the need for removing the previous solution and adding the next solution for each assay step, since all well plates were prepared before the assay is performed. Furthermore, the volume of anti-IL-6 antibody required for completely covering one chip array on the pillar plate was 10 μl compared to 25 μl required for a conventional assay using regular microarrays being placed in well plates. Finally, the number of peptides or features immobilized on each chip is approximately 2,000,000 which allows for more data to be collected from a single chip and better data analysis. Table 1 compares the assay involving chips on a 96-pillar plate with a conventional microarray assay.

TABLE 1

| Assay Comparison | | |
|---|---|---|
| Assays Parameters | 96-pillar plate | conventional assay |
| Time for assay completion | 85 minutes | 160 minutes |
| Antibody quantity | 10 μl/chip | 25 μl/well |
| Number of tested peptides | 2,000,000/chip | 135,000/well |

A more detailed comparison of the performance of various pillar plate configurations is presented in Table 2.

TABLE 2

Assay Performance Pillar Plate Comparison

| No. of pillars | Chip size (mm²) | Chip per pillar | No. of detected features (min-max) | Assay throughput | Scan and analysis throughput | Features/ sample/sec (min-max) |
|---|---|---|---|---|---|---|
| 24 | 100 | 1 | 2m-18m | 20 mins/4 plates | 2.8 hr/4 plates | 19047-171428 |
| 96 | 20.25 | 1 | 400k-3.5m | 20 mins/4 plates | 2.8 hr/4 plates | 15238-133333 |
| 384 | 4 | 1 | 81k-720k | 20 mins/4 plates | 2.8 hr/4 plates | 12342-109714 |
| 1536 | 1.56 | 1 | 30k-270k | 20 mins/4 plates | 2.8 hr/4 plates | 18292-164634 |
| 24 | 0.16 | 400 | 120k-1m | 20 mins/4 plates | 2.8 hr/4 plates | 1142-9523 |
| 96 | 0.16 | 81 | 25k-225k | 20 mins/4 plates | 2.8 hr/4 plates | 952-8571 |
| 384 | 0.16 | 16 | 5k-45k | 20 mins/4 plates | 2.8 hr/4 plates | 761-6857 |
| 1536 | 0.16 | 4 | 1k-9k | 20 mins/4 plates | 2.8 hr/4 plates | 609-5487 | m = millions; k = thousands.

Example 8: Variations and Performance in Assays Probing p53 TAD1 on Pillar Pates This Example describes a variation of the above assay protocol in Example 6 includes using anti-p53 antibody and growing the p53 10aaTAD1 transcription activation factor having the amino acid sequence LKWLDSFTEQ (SEQ ID NO: 1; disclosed in the C-term to N-term orientation) on the chips of pillar plates. The sequence is listed in the reverse order, since the peptide is synthesized on each chip in multiple locations starting from the N-terminus. The assay determined variation in results obtained from multiple locations within one chip (intra-chip), from the same location between two chips (inter-chip), from chip locations within chips that were mounted on pillars located at the same position among different plates (intra-pillar), and from chip locations within chips on pillars located at different position on a plate (inter-pillar). To ensure that these locations coincide among the different chips during the measurement, the chips were aligned based on alignment marks as described in more detail below.

Intra-chip variations in intensities were measured by analyzing the data obtained for different locations on one chip by detecting the p53 TAD1 peptide using the assay protocol as described above. The intra-chip variations in intensities listed in Table 3 were obtained from a single chip.

TABLE 3

| Intra-chip intensity variation | |
|---|---|
| Location | Binding Intensity |
| 1 | 61245 |
| 2 | 62030 |
| 3 | 61075 |
| 4 | 61145 |
| 5 | 61324 |

Inter-chip variations in intensities were measured by analyzing the data obtained from five chips with the data collected at five different locations for each chip. Again the results indicated the binding of anti-p53 antibody to p53TAD1 peptide immobilized at locations 1-5 on each chip according to the assay protocol as described above. The inter-chip variations in intensities listed in Table 4 were obtained from a single pillar plate.

TABLE 4

| Inter-chip intensity variation | | | | | |
|---|---|---|---|---|---|
| Location | Chip1 Intensity | Chip2 Intensity | Chip3 Intensity | Chip4 Intensity | Chip5 Intensity |
| 1 | 61075 | 60987 | 60471 | 60001 | 61245 |
| 2 | 60985 | 60147 | 61025 | 61234 | 62030 |
| 3 | 61040 | 60023 | 61003 | 61147 | 61075 |
| 4 | 61075 | 60754 | 61002 | 61074 | 61145 |
| 5 | 61115 | 61712 | 60965 | 60465 | 61324 |

Intra-pillar variations in intensities were measured by analyzing the data obtained from five chips on five different plates with the data collected from five different locations on each chip. In addition, the five pillars holding the chips were located at the same position within a 96-pillar plate when comparing the plates with each other. The intra-pillar variations in intensities listed in Table 5 were obtained from a five chips on five different 96-pillar plates.

TABLE 5

| Intra-pillar intensity variation | | | | | |
|---|---|---|---|---|---|
| Location | Chip1 Intensity | Chip2 Intensity | Chip3 Intensity | Chip4 Intensity | Chip5 Intensity |
| 1 | 60570 | 61985 | 61748 | 60223 | 60040 |
| 2 | 60985 | 62005 | 61025 | 60368 | 61000 |
| 3 | 61010 | 60425 | 61002 | 61085 | 60000 |
| 4 | 61005 | 60586 | 61056 | 61096 | 60963 |
| 5 | 60999 | 60789 | 60458 | 60325 | 60332 |

Inter-pillar variations in intensities were measured by analyzing the data obtained from five chips on five different pillars at different positions on the same 96-pillar plate. In addition the data was collected from five different locations on each chip. The inter-pillar variations in intensities listed in Table 6 were thus obtained from a five chips on a single 96-pillar plate.

TABLE 6

| Inter-pillar intensity variation | | | | | |
|---|---|---|---|---|---|
| Location | Chip1 Intensity | Chip2 Intensity | Chip3 Intensity | Chip4 Intensity | Chip5 Intensity |
| 1 | 60765 | 60456 | 61039 | 61042 | 61355 |
| 2 | 60452 | 62010 | 60564 | 62014 | 61421 |
| 3 | 60125 | 61078 | 61026 | 60642 | 61014 |

TABLE 6-continued

Inter-pillar intensity variation

| Location | Chip1 Intensity | Chip2 Intensity | Chip3 Intensity | Chip4 Intensity | Chip5 Intensity |
|---|---|---|---|---|---|
| 4 | 60352 | 60987 | 62356 | 60933 | 60784 |
| 5 | 60332 | 61020 | 60789 | 60000 | 60332 |

The intensity data from Tables 3-6 was then averaged over the five locations and chips for each experiment. The experimental average (=mean) in intensity variations including the mean±variation % are listed in Table 7, where the variation % was calculated by dividing the standard deviation by the mean of the collected data.

TABLE 7

Intensity variations averaged over locations and chips

| Variation Type | Intensity (Mean ± Variation %) |
|---|---|
| Intra-chip variation | 61363.8 ± 0.56% |
| Inter-chip variation | 60964.76 ± 0.69% |
| Intra-pillar variation | 60843.2 ± 0.857% |
| Inter-pillar variation | 60915.52 ± 0.938% |

Example 9: Sensitivity of Chip to Antibody Concentration

Figure 24:
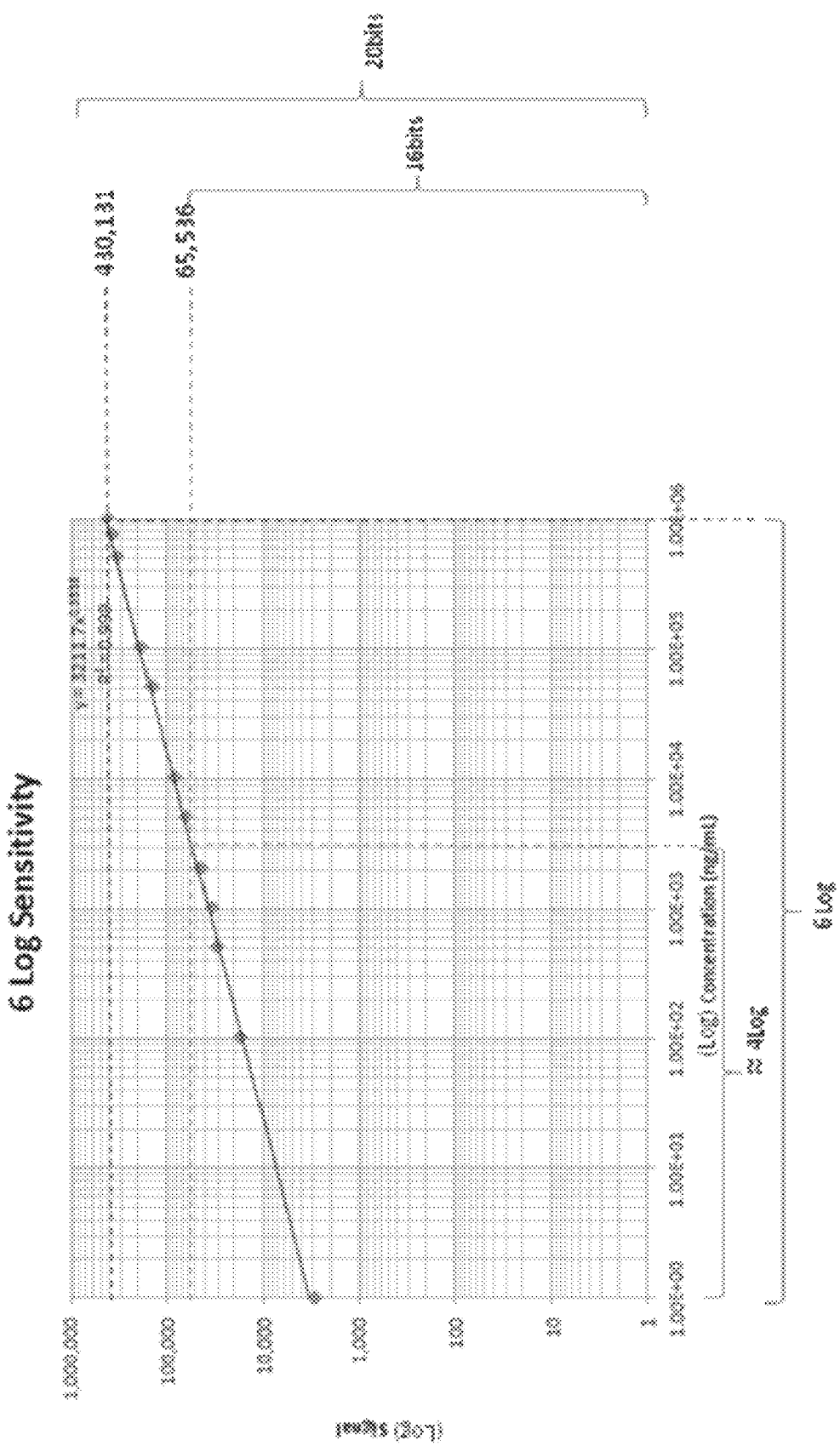
FIG. 24 shows a detection range (sensitivity) of a chip over a range of antibody concentrations, according to one embodiment.

In this example, the sensitivity of a single 10 mm by 10 mm sized chip was measured with respect to increases in antibody concentration. The assay protocol is similar to the one described in Example 8 using anti-p53 antibody upon coupling a p53 10aaTAD1 peptide to the chip surface. The confocal scanner microscope can measure a relative intensity of up to 65,536 ($=2^{16}$) when using an image chip that contained a resolution of 16-bits per pixel. With a maximum measurable intensity of 65,536 the scanner was capable of measuring a change in concentration covering 4 Log orders. Increasing the resolution to 20 bits per pixel yielded a maximum signal resolution of 1,048,576 ($=2^{16}$) with a concentration sensitivity of 6 Log orders (FIG. 24). Measurements of the intensity changes by increasing the antibody concentration are listed in Table 8, including the intensity signal of a single feature, the intensity averaged among all features on the chip and the corresponding variation % that was calculated by dividing the standard deviation by the mean (=average) of the collected feature intensity data.

TABLE 8

Contentration dependency of intensity (chip sensitivity)

| Concentration | Intensity | Average Intensity | Variation % |
|---|---|---|---|
| 1 ng/ml | 3,024 | 3,146 | 1.14% |
| 100 ng/ml | 18,202 | 19,117 | 1.04% |
| 500 ng/ml | 31,456 | 32,438 | 1.64% |
| 1 µg/ml | 35,564 | 36,765 | 1.42% |
| 2 µg/ml | 46,132 | 48,453 | 1.43% |
| 5 µg/ml | 66,692 | 69,327 | 1.46% |
| 10 µg/ml | 85,293 | 88,794 | 1.07% |
| 50 µg/ml | 150,900 | 154,631 | 1.52% |
| 100 µg/ml | 193,012 | 200,694 | 1.09% |
| 500 µg/ml | 342,400 | 356,100 | 1.87% |
| 750 µg/ml | 395,429 | 415,289 | 1.38% |
| 1,000 µg/ml | 430,131 | 455,861 | 1.90% |

Figure 25:
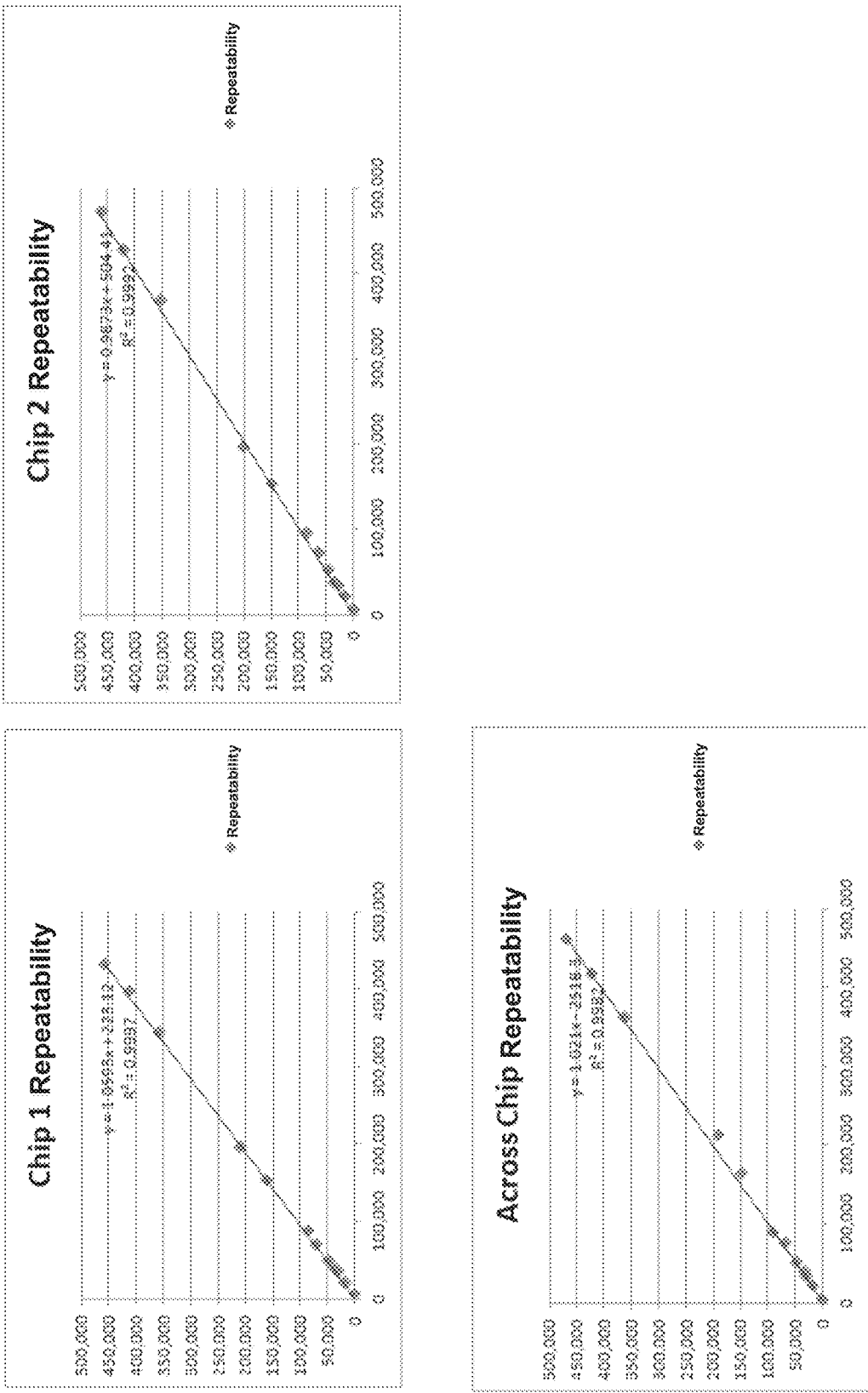
FIG. 25 shows reproducibility of assay results across multiple chips, according to one embodiment.

To confirm reproducibility, the same experiment was twice repeated for two different chips (Chip 1 and Chip 2). With an $R^2$ of 0.9997 and 0.9992 among the two experiment for each chip, respectively, and an $R^2$ of 0.9982 among the two chips the sensitivity of each chip was repeatedly reproduced (FIG. 25), and thus is reliable to a high degree.

Example 10: Analysis of Confocal or CCD Scanner Microscope Signal Output Scanning an Ultra High Feature Density Chip Array This example describes the analysis of a chip array by identifying regions of interest for piecewise scanning, correcting scanned frames for misalignment among chips, and stitching the data of each frame to account for frame overlaps. A 24-pillar or 96-pillar plate was placed on the stage of a Nikon MR confocal microscope or CCD scanner microscope. The 24-pillar and 96-pillar plates were as described in Example 5 and contained multiple chips per chip array mounted on each plate pillar. The chips were pre-aligned during mounting on the chip array with a pre-alignment accuracy of about ±50 µm as shown in the actual chip layout in FIG. 26. To get the data from the scanned frames without missing any feature rows or columns, data stitching is important. For data stitching to be accurate, the alignment of the scanned frames required a high degree of accuracy. A higher accuracy was achieved by rotating the stage around its centre (coinciding with the plate centre) before scanning a chip to correct for any misalignment of the chip within respect to other chips on the plate.

Identification of ROIs on Microarray

Figure 27:
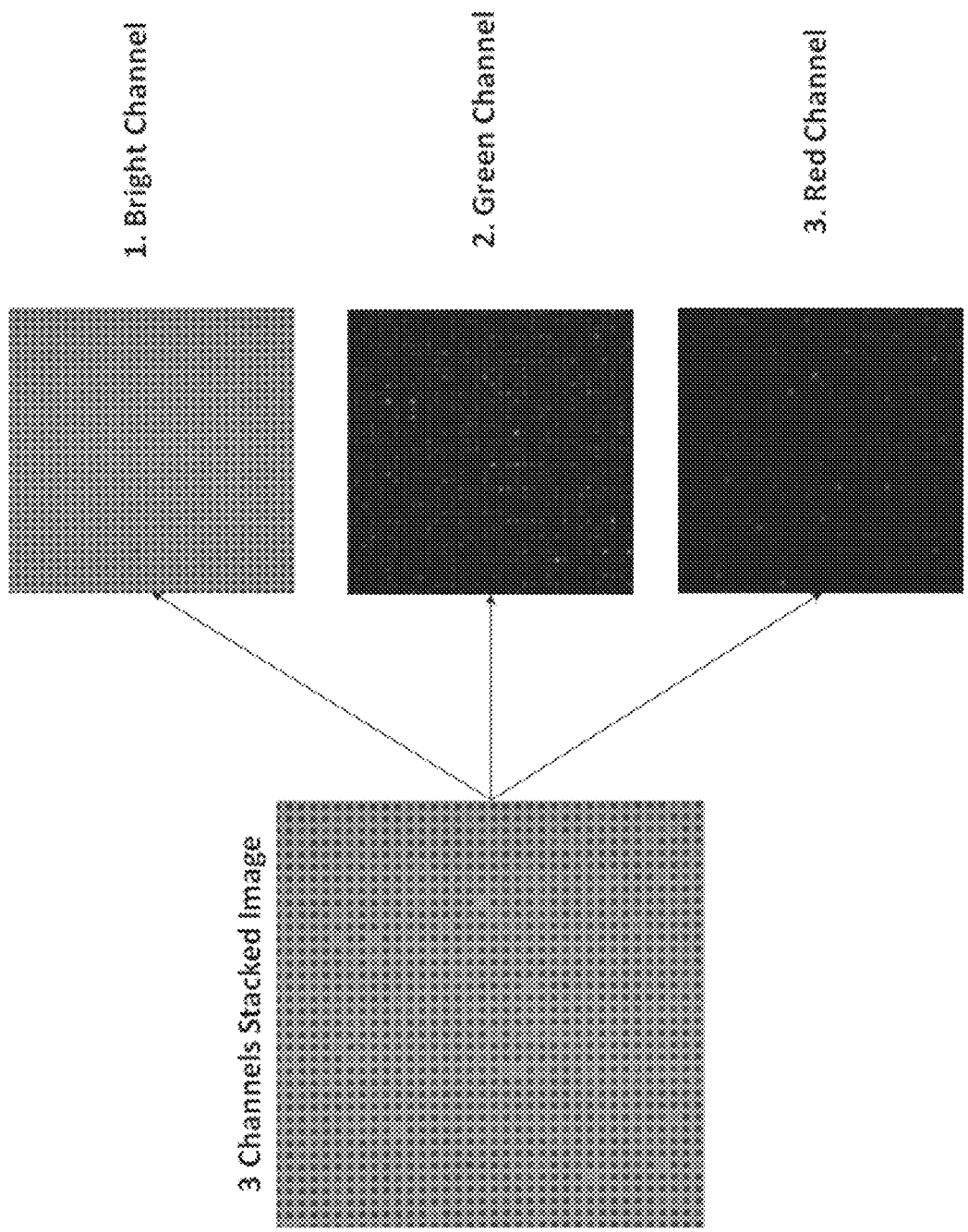
FIG. 27 shows an image of a chip array of three merged channels including reflected light (bright) and two filtered channels (red and green), according to one embodiment.

Refraction differences due to the composition of surface of a chip containing substrate pillars substrate (as described above) was used to accurately determine regions of interest (ROIs) for the analysis of a chip array. The contrast between the metal layer and the substrate (silica/nitride) where the probe molecules (features) were present provided for intensity to be picked up using reflected light from a confocal laser source. This enabled piece-wise scanning of different microarrays on a chip array. The image from the reflected light was used to map out different ROIs on a chip. One or more laser sources along with a scanner was used to excite emission and capture the reflected and emitted light for picking up signal intensities from different fluorophores located within various ROIs. An image of the reflected light and images of the red and green emission light channels from a single chip are shown in FIG. 27.

Figure 28:
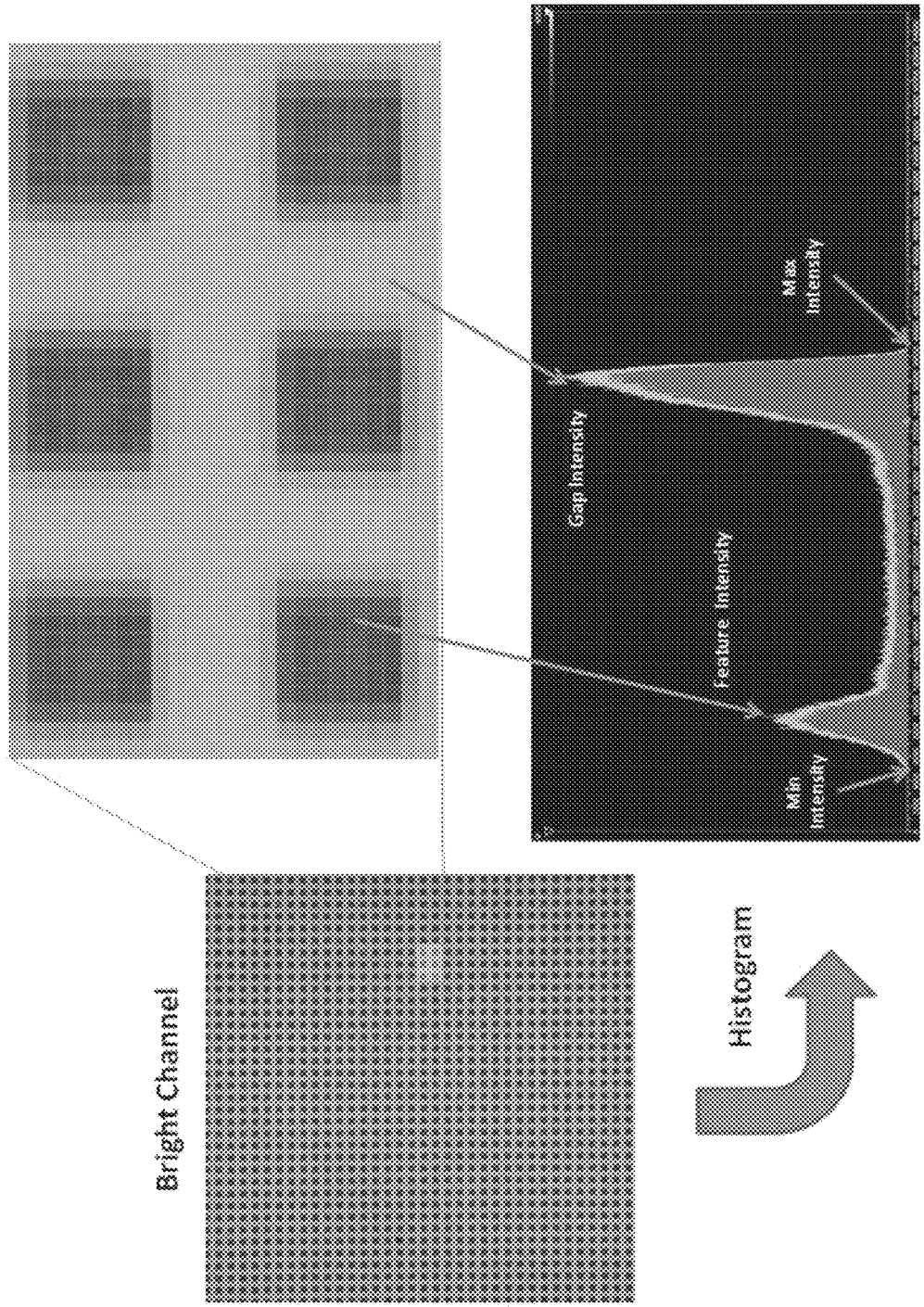
FIG. 28 shows a pixel diagram and an intensity profile of the reflected light (bright) channel across a surface of a chip array, according to one embodiment.

The reflected light image from each frame map out where the fluorophore intensities need to be measured. By setting a threshold for the reflected light image one can distinguish ROIs containing features from background areas on a chip as shown in FIG. 28. Background areas contain metal that generated a different contrast compared to the pillar substrate so that one easily differentiated those areas from the ROI areas of features. The data was collected for each frame only from ROI areas (defined by the reflected light map and containing features) which can be characterized by the stage coordinate X and stage coordinate Y position for each feature along with its averaged fluorophore intensity measured at one or multiple wavelengths (multiplex) at the same time.

Figure 29:
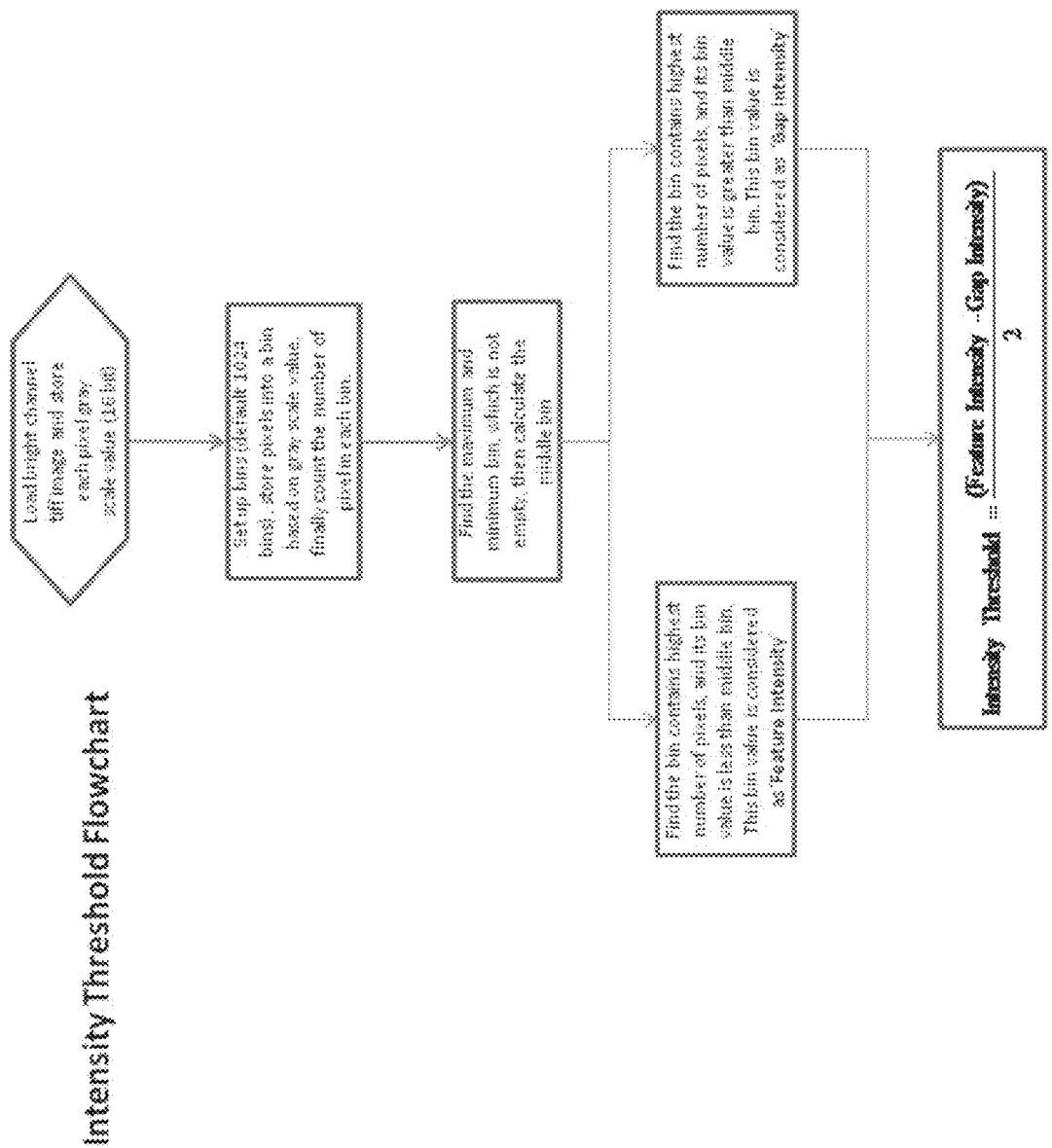
FIG. 29 shows a flowchart for calculating an intensity threshold that eliminates background noise on a chip array, according to one embodiment.
Figure 30:
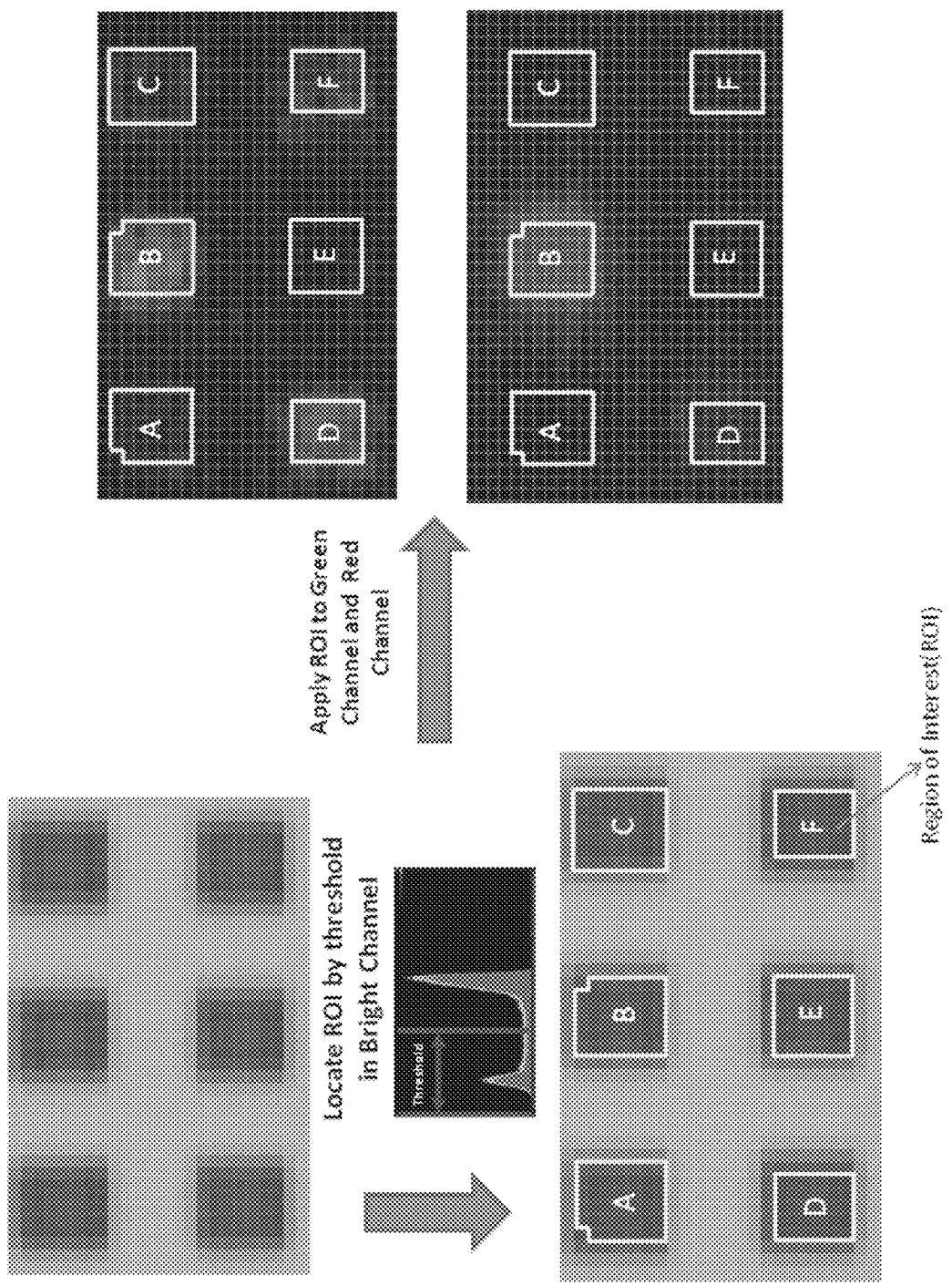
FIG. 30 shows results of using an intensity threshold to identify regions of interest (ROIs) on a chip array and applying the identified ROIs to two filter channels (red and green), according to one embodiment.

A flowchart illustrating the process of determining an intensity threshold for identifying ROIs on a chip is shown in FIG. 29. The so-determined ROIs on the chip are shown in FIG. 30.

Correction for Chip Misalignment

Figure 31:
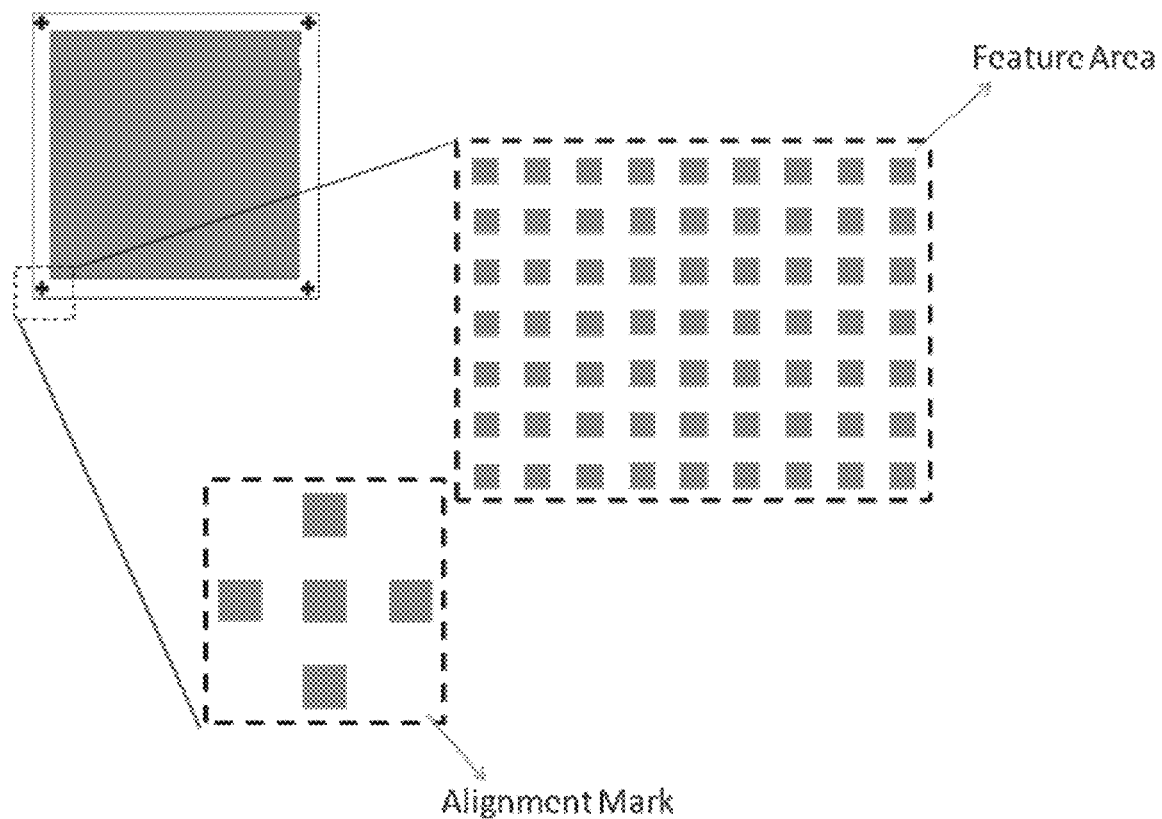
FIG. 31 shows the size of a chip's alignment mark in comparison to areas on the chip occupied by features, according to one embodiment.
Figure 32:
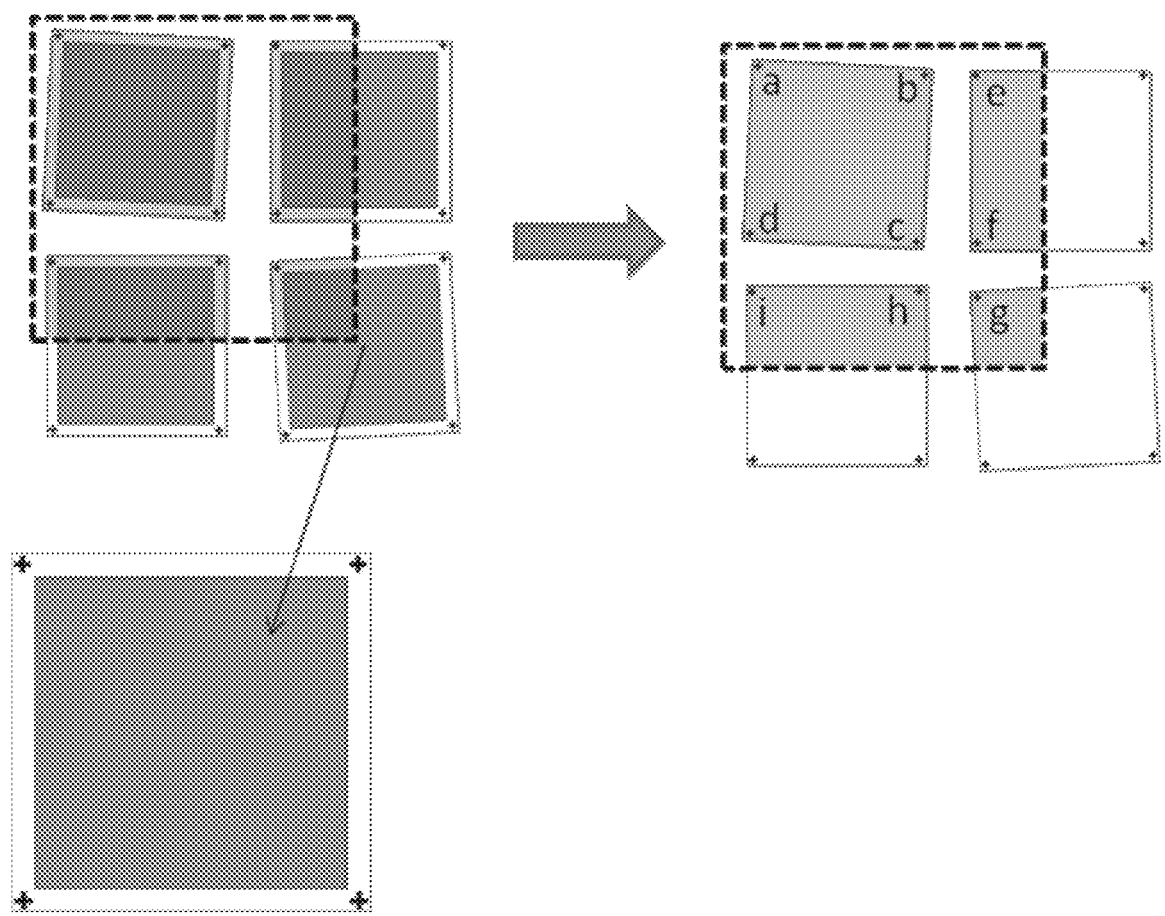
FIG. 32 shows the identification of alignment marks of different chips on a chip array within one scanning area of a confocal microscope, according to one embodiment.

In order to process multiple chips on a chip array, alignment marks were used to correct for any misalignment among the chips caused during pre-alignment. Each chip was marked with squared alignment marks that were at least 1.5 times larger than any squared feature area on a chip as shown in FIG. 31. The chip boundary was defined by four alignment marks. Thus, a software program can recognize alignment marks and feature areas based on size. Coordinates of alignment marks were used as plate stage coordinates, since the gaps between chips are much smaller than chip size with more than one chip being scanned at a time. For example shown in FIG. 32, 9 alignment marks (a-g) fall within the scanned frame if the chip was not centered within the frame and area occupied by the chip and its surrounding gaps was smaller than the frame area. To distinguish between alignment marks from the same and other chips, the distance between any scanned alignment marks was determined and only alignment marks (a-c) with distances being approximately equal to chip size belong to the same chip. For some chip, all four alignment marks (e-f, g, and h-i) did not fall within the same frame area. The process then searched for the remaining alignment marks in adjacent frames.

Figure 33:
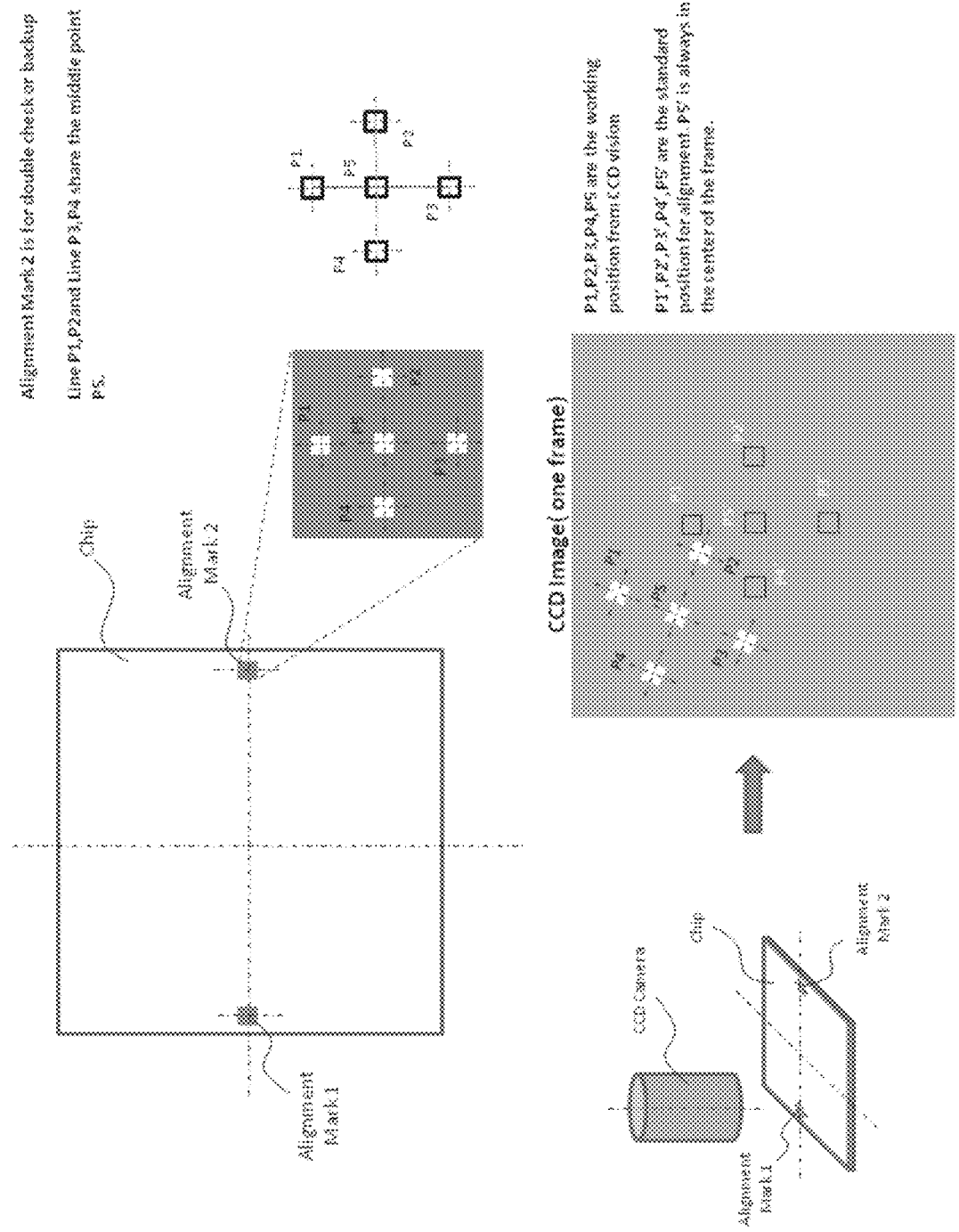
FIG. 33 shows the alignment of a chip array using alignment marks to accurately identify regions of interest, e.g. a chip, and to position the chip for scanning by a confocal microscope (CCD camera), according to one embodiment.

In another example, with the chip size far exceeding the frame size each chip had two alignment marks on two edges as shown in FIG. 33. Each alignment mark contained 5 points P1, P2, P3, P4 and P5 as a cross pattern, wherein the line connecting P1 to P2 and the line connecting P3 and P4 shared middle cross point P5. Instead of using a cross pattern these five points were located using an algorithm that differentiated the pattern from the background using a intensity histogram or the size of the alignment mark pattern as discussed above. The CCD camera then detected the five points (P1, P2, P3, P4, and P5) and a software program compared these points with the standard reference positions (P1', P2', P3', P4', and P5') with P5' being in the frame center.

Figure 34:
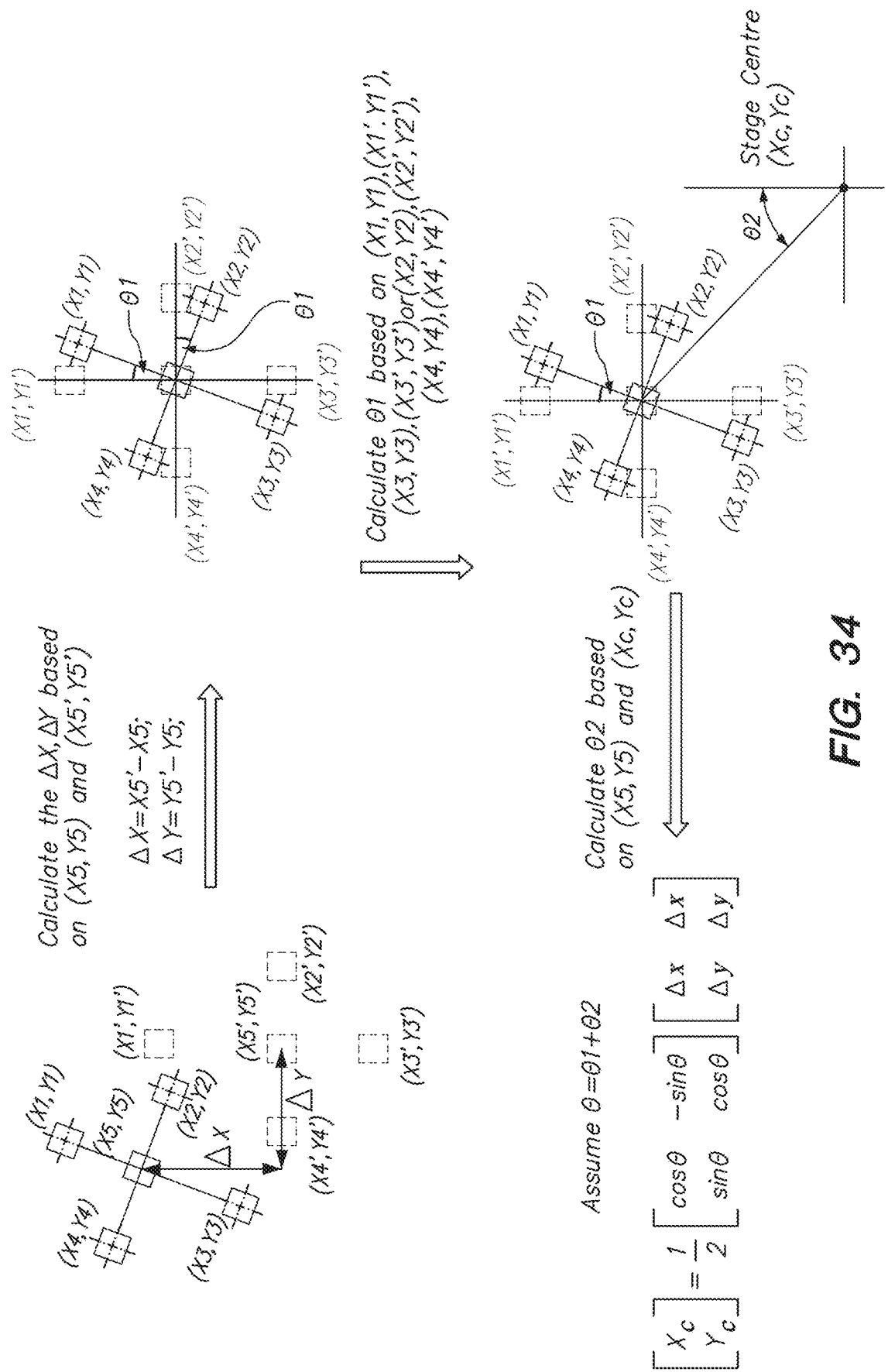
FIG. 34 shows a flow chart for position a chip on a chip array by translating and rotating the chip based on the actual and the desired position of an alignment mark on the chip, according to one embodiment.
Figure 35:
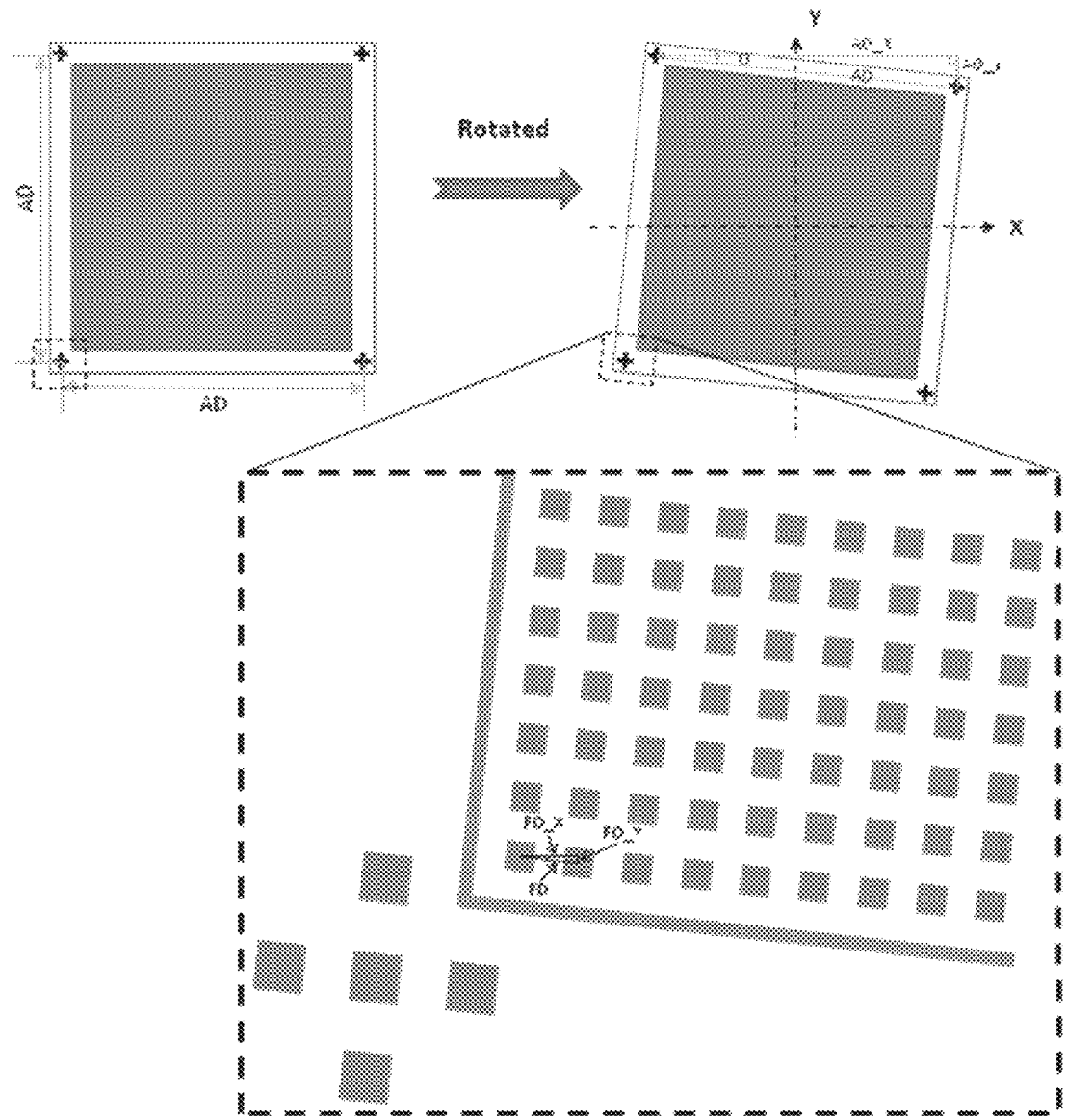
FIG. 35 shows the positioning of a chip by theta-angle rotation based on the position of an alignment mark on the chip, according to one embodiment.
Figure 36:
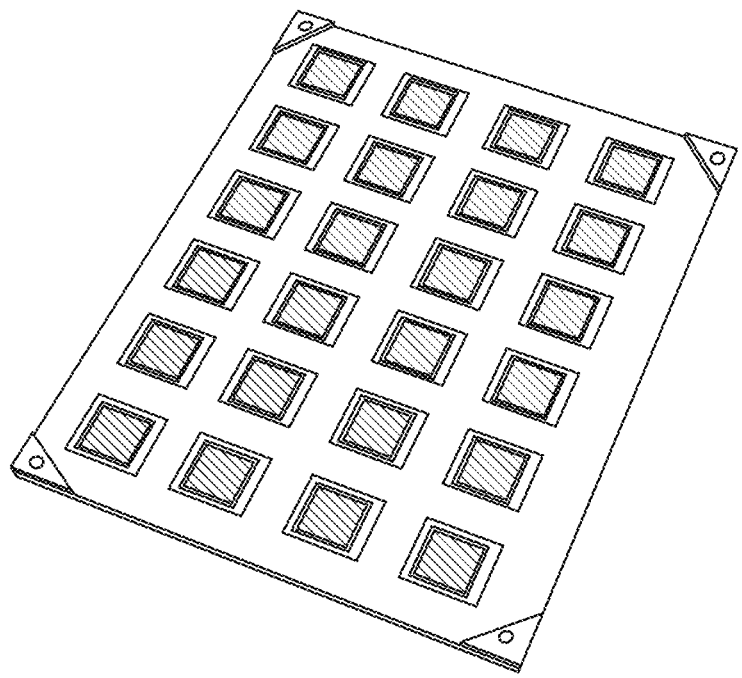
FIG. 36 shows the first step of mounting the chips in a process flow for calculating the angle of correction about the center of a chip array to correct for misalignment between chips on the chip array, according to one embodiment.
Figure 37:
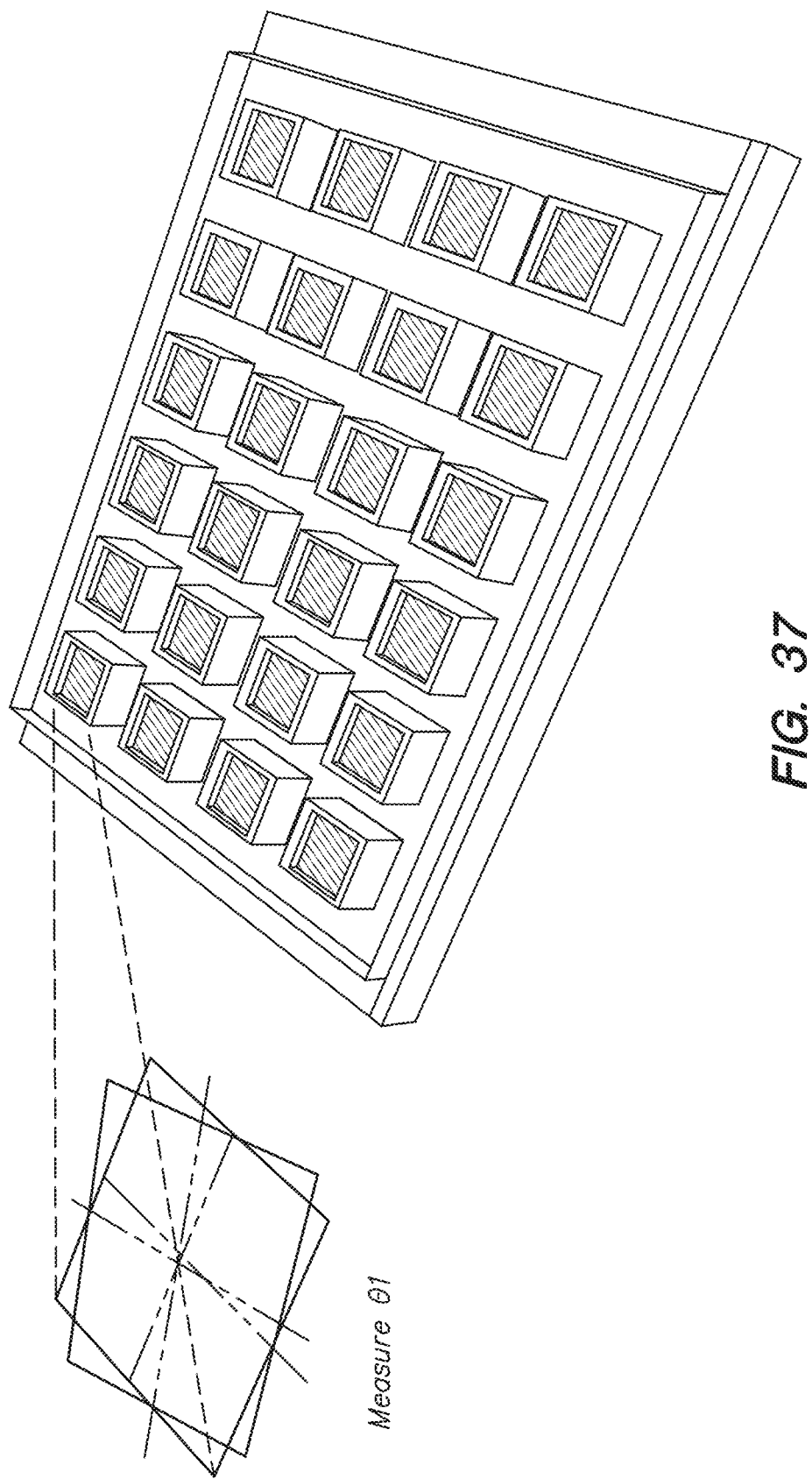
FIG. 37 shows the second step of determining the first rotation angle ($\theta_1$) for a chip in a process flow for calculating the angle of correction about the center of a chip array to correct for misalignment between chips on the chip array, according to one embodiment.
Figure 38:
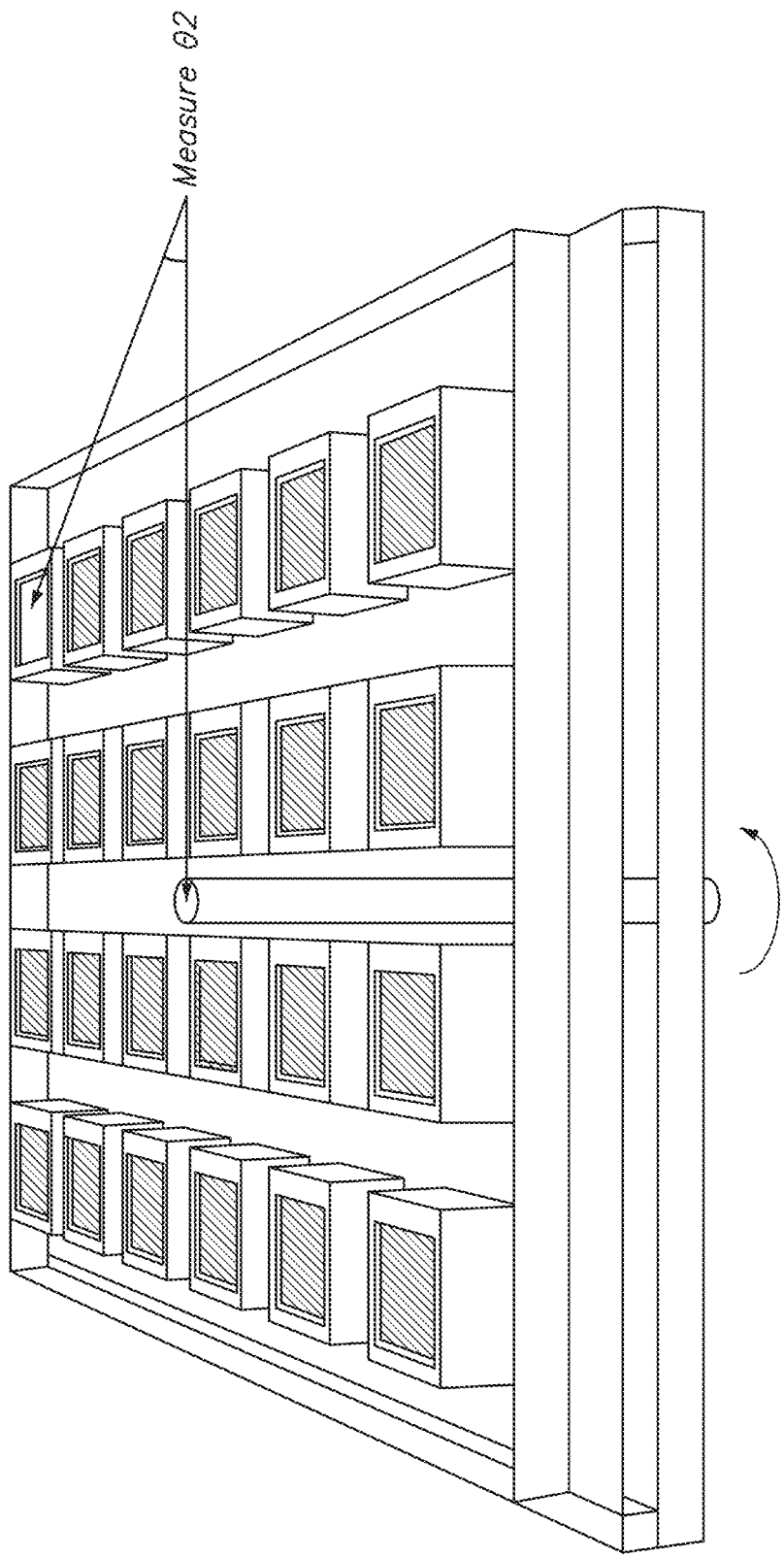
FIG. 38 shows the third step of determining the second rotation angle ($\theta_2$) for a chip in a process flow for calculating the angle of correction about the center of a chip array to correct for misalignment between chips on the chip array, according to one embodiment.
Figure 39:
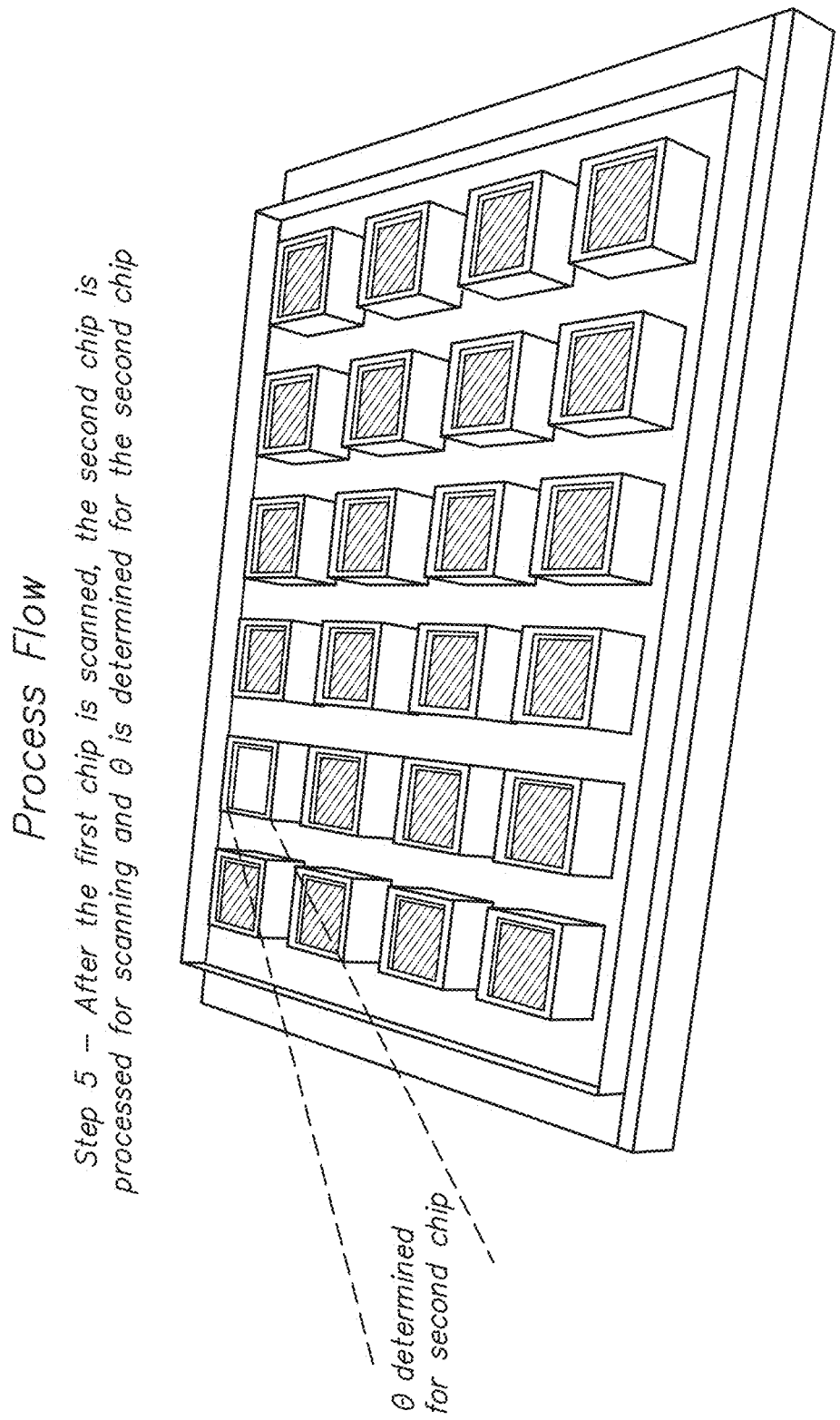
FIG. 39 shows the fourth step of determining rotation angles of another chip in a process flow for calculating the angle of correction about the center of a chip array to correct for misalignment between chips on the chip array, according to one embodiment.

In both examples, a software program then calculated a rotation angle theta (θ) and offset translation to correct for the misalignment of alignment mark with respect to a standard reference position of the chip array as illustrated in FIGS. 34 and 35. The relationships between theta and various distance parameters were given by:

$$\tan\theta = \frac{AO\_Y}{AO\_X} = \frac{FO\_Y}{FO\_X},$$

$$\cos\theta = \frac{AO\_X}{AD} = \frac{FO\_X}{AD}, \sin\theta = \frac{AO\_Y}{AD} = \frac{FO\_Y}{FD},$$

$$AD = \sqrt{AO\_X^2 + AO\_Y^2}, FD = \sqrt{FO\_X^2 + FO\_Y^2},$$

with AD being the alignment distance, AO_X the alignment offset along the X-axis, AO_Y the alignment offset along the Y-axis, FD the feature distance, FO_X the feature offset along the X-axis, and FO_Y the feature offset along the Y-axis. The subsequent steps for correcting for misalignment among chips on a chip array are shown in FIGS. 36-39 based on aligning the pillar plate by rotating the stage around its centre.

Frame Stitching

Figure 40:
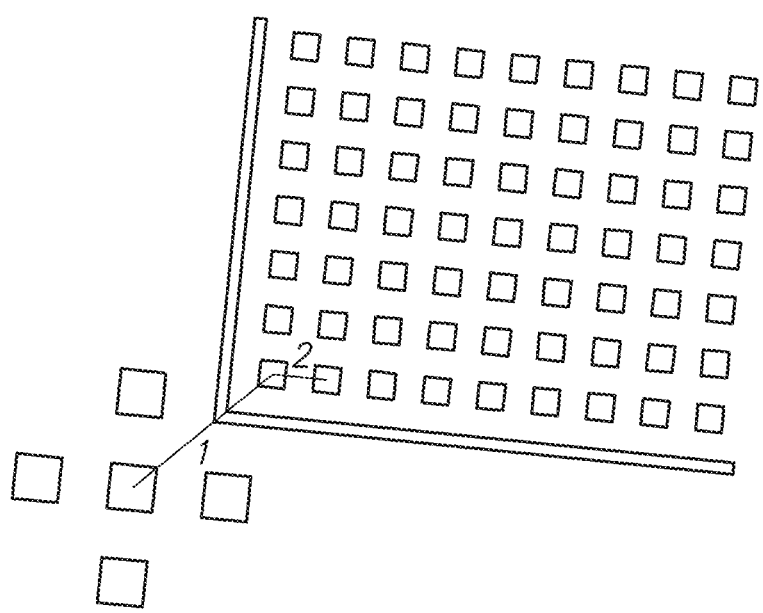
FIG. 40 shows the stitching of feature data obtained from chips on a chip array, according to one embodiment.

Data from each frame was then stitched together with each adjacent frame with two adjacent frames overlapping by 5-10% or 0.1 mm as shown in the example in FIG. 30. To determine the positions of all features on a chip, based on the alignment coordinates the corner feature of a chip was first located as shown in FIG. 40. From the corner feature, the location of next feature was calculated using FO_X and FO_Y. Subsequent features were located by repeatedly moving along the X- and Y-axis in steps of FO_X and FO_Y.

The features having the same global coordinates were then data-stitched in real time rather than image-stitched which eliminates time and discrepancies due to stitching images. Real time stitching included that after an image was acquired, the data was pulled out and stored in an external file or data storage that was continuously and simultaneously appended (stitched) when another image was scanned. The total time for scanning and stitching images of an ultra high density microarray with more than 500 k features took less than 10 minutes as compared to 35 minutes using image-processing software, e.g. Genepix. A high throughput multithreading algorithm further reduced this total time of scanning and stitching to the range of a few seconds.

Figure 41:
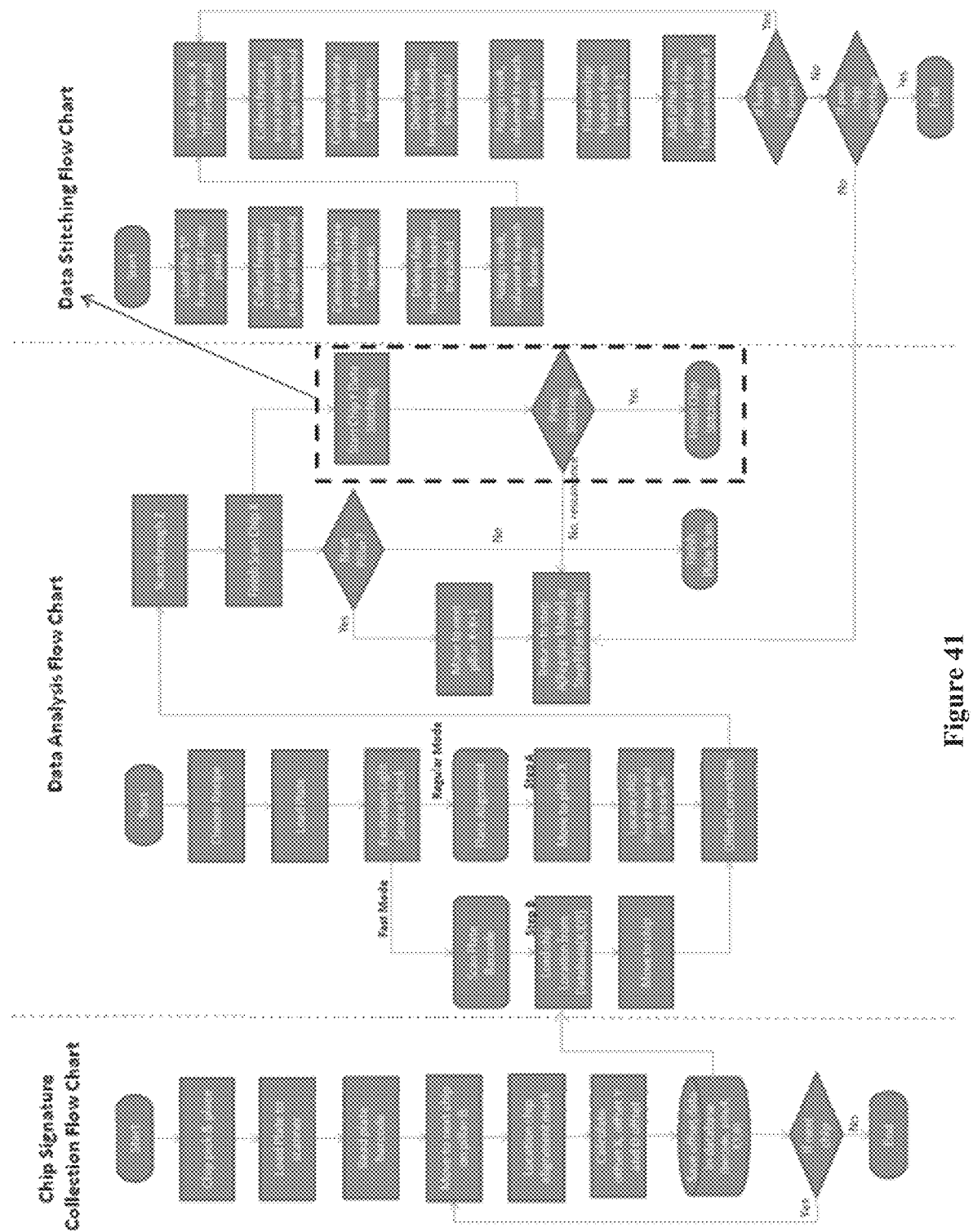
FIG. 41 shows flow charts for collecting a chip's signature data, e.g. bar code, alignment marks to determine offsets and rotation angles, for analyzing chip data from an assay and for stitching together assay data from multiple chips on a chip array, according to one embodiment.

FIG. 41 illustrates a flow chart summarizes the various steps of data analysis of an ultra high feature density chip array.

Example 11: Quality Control Monitoring System

This example describes inline and end-of-line quality control (QC) monitoring systems that assure high quality chips with ultra high feature density.

Inline Quality Control

The benefit of an inline quality control monitoring system that correct measures can be taken before the end of the manufacturing line is reached was demonstrated in this Example. This increased the throughput efficiency and decreased the manufacturing time by maintain a high yield of high quality chips.

Inline Quality Control of Chip Array Thickness

In FIG. 42, the wafer was coated in step 1 with a photobase solution containing photobase, polymer and amino acid and soft baked at 85° Celsius for 90 seconds. In the next control step 2 (QC1), the wafer thickness was measured and monitored for comparison with the expected specifications (Table 9). If the thickness measured was not within the standards specified, further processing of the wafer was stopped and the wafer was stripped, recoated and followed by repeating steps 1 and 2. The wafer was then exposed using a photomask at 248 nm in step 3 before being hard backed at 85° Celsius for 90 seconds in step 4. In the last step 5 (QC2), the wafer thickness was again measured and monitored for comparison with the expected specifications (Table 9). If the thickness measured was not within the standards specified, further processing of the wafer was stopped with the wafer being stripped and recoated and then repeating steps 1 through 5 again.

TABLE 9

| QC Step | Thickness threshold |
|---|---|
| | Pass Criteria for Thickness |
| QC1 | 2400 nm ± 30 nm |
| QC2 | 800 nm ± 10 nm |

In this example, the inline QC monitoring system was tested on a set of 15 wafers while continually monitoring the thickness for each wafer. The results of the test are listed in Table 10 with only two wafers failing the QC1 and additional two failing the QC2 step.

TABLE 10

Inline QC Test Results

| Wafer # | QC1 | QC2 | Status |
|---|---|---|---|
| W1 | 2402 nm | 795 nm | Passed |
| W2 | 2415 nm | 792 nm | Passed |
| W3 | 2385 nm | 805 nm | Passed |
| W4 | 2444 nm | — | Failed QC1 |
| W5 | 2398 nm | 810 nm | Passed |
| W6 | 2385 nm | 795 nm | Passed |
| W7 | 2407 nm | 802 nm | Passed |
| W8 | 2425 nm | 815 nm | Failed QC2 |
| W9 | 2430 nm | 794 nm | Passed |
| W10 | 2415 nm | 804 nm | Passed |
| W11 | 2375 nm | 797 nm | Passed |
| W12 | 2450 nm | — | Failed QC1 |
| W13 | 2403 nm | 808 nm | Passed |
| W14 | 2400 nm | 799 nm | Passed |
| W15 | 2398 nm | 820 nm | Failed QC2 |

Inline Diffusion and Overlay Quality Control

Figure 43A:
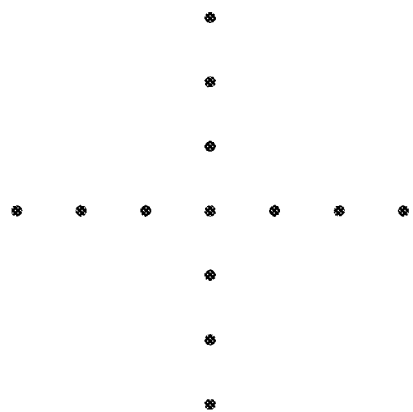
FIG. 43A-B show the diffusion and overlay test pattern of a photomask and a standard intensity pattern of a chip under a confocal microscope after UV-light exposure with the photomask and baking of the chip, respectively, according to some embodiments.

An additional inline QC monitoring step included checking for diffusion and overlay variations. In this example, after the wafer was exposed using a photomask at 248 nm and baked, the diffusion pattern of the photobase is regulated using a standard microscope to determine if the pattern matches the expected standard pattern as follows: For this monitoring step a standard test diffusion and overlay pattern was etched into photomask at predetermined locations as shown in FIG. 43A.

Figure 43B:
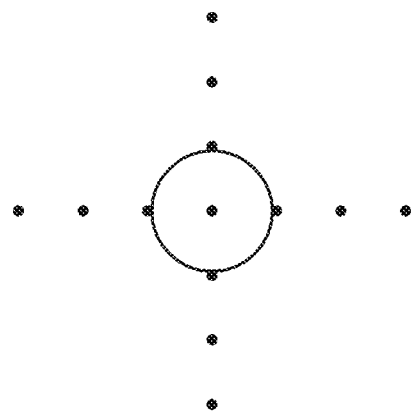

The distance between each dot was 100 nm and was equidistant in +X, −X, +Y and −Y direction. If the wafer was exposed under standard conditions, the pattern under the microscope appeared as shown in FIG. 43B (standard pattern after exposure and bake). In case of any derivation from standard conditions as a result from a difference in exposure energy or placement of the wafer, the results deviated from the standard diffusion and overlay pattern, respectively. Some test cases for correct and incorrect overlay and diffusion amount are listed in Table 11 and illustrated in FIGS. 44A-C, wherein an incorrect overlay or diffusion pattern would deviate by more than 5% from the standard pattern, respectively. Only the correct diffusion and overlay pattern shown in FIG. 44A was accepted and the wafer continued processing. In any other case, the processing of the wafer was stopped with the wafer being stripped, recoated and reassessed with the inline QC monitoring system.

TABLE 11

Diffusion and overlay test results

Figure 44A:
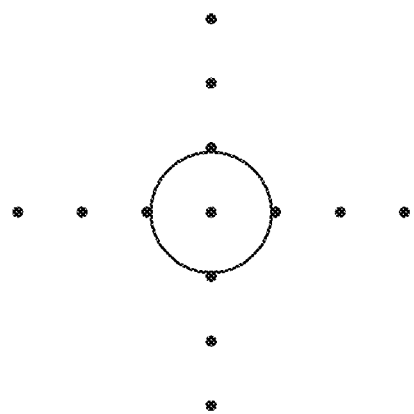
FIG. 44A-D show standard intensity pattern of a chip as shown in FIG. 38B and variations in overlay locations and diffusion amount, respectively, according to some embodiments.
Figure 44B:
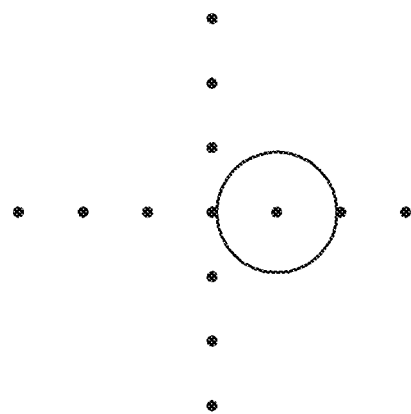
Figure 44C:
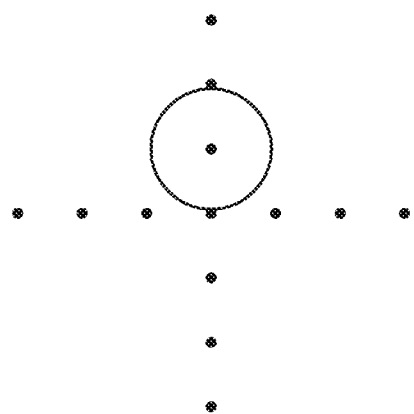
Figure 44D:
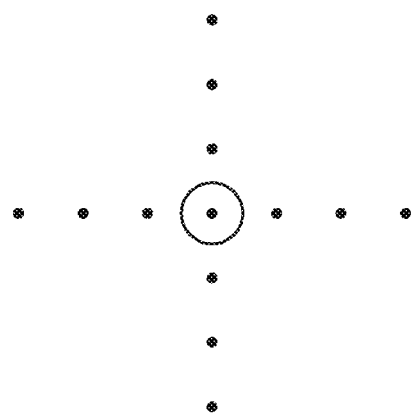
Figure 45A:
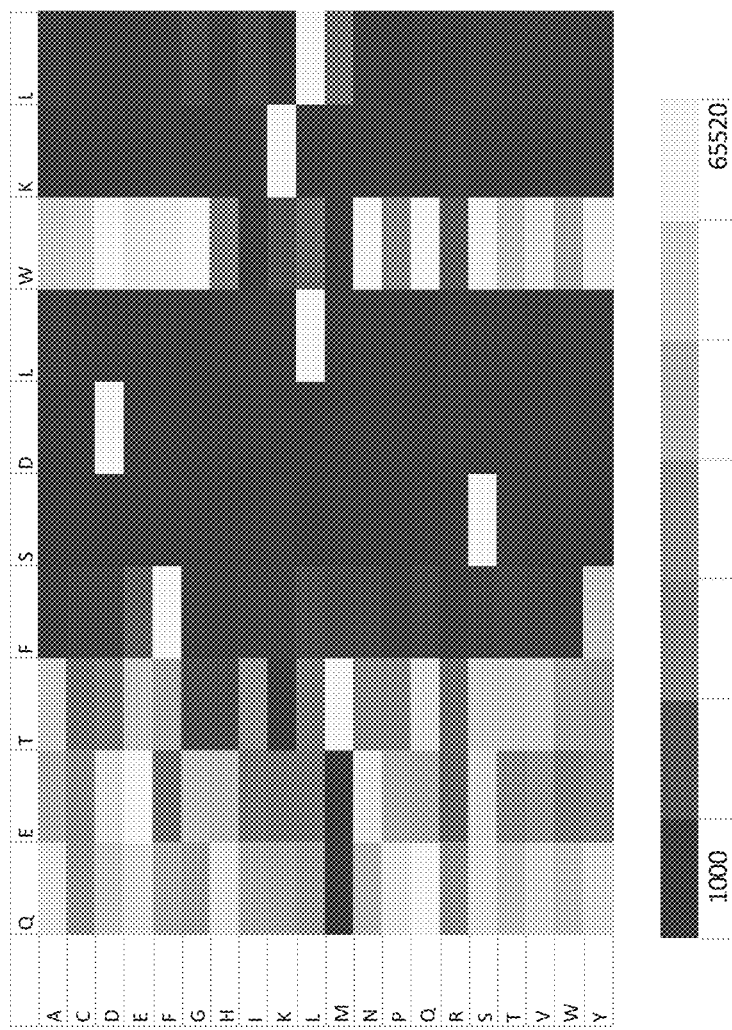
FIGS. 45A-K show intensity profiles for point mutations of peptides binding an antibody to determine which amino acids in the peptide sequence are material to binding the antibody, according to some embodiments. The original peptide sequence of amino acids is shown in single letter code along the top of each intensity profile (SEQ ID NOS 1-11, respectively, in order of appearance) with the corresponding amino acid replacement (point mutation) along the vertical axis.
Figure 45B:
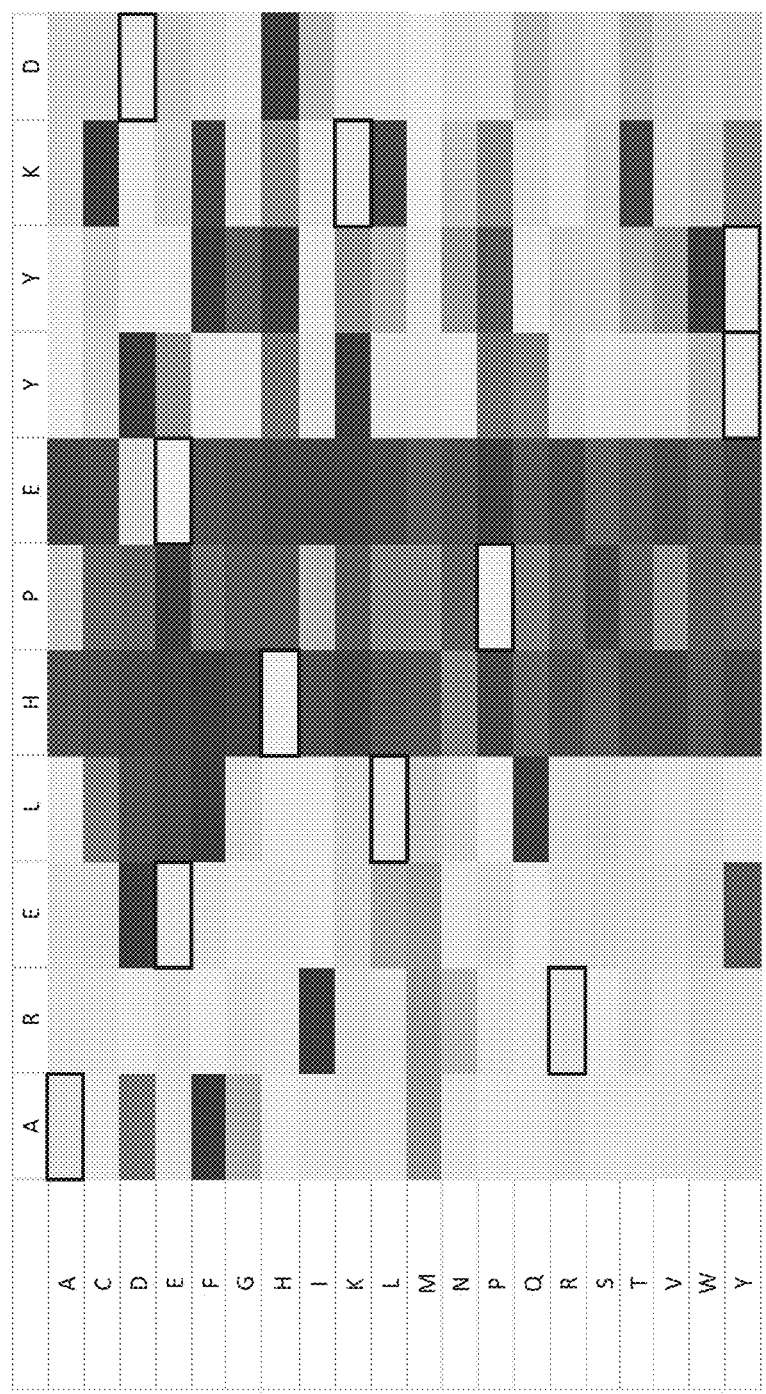
Figure 45C:
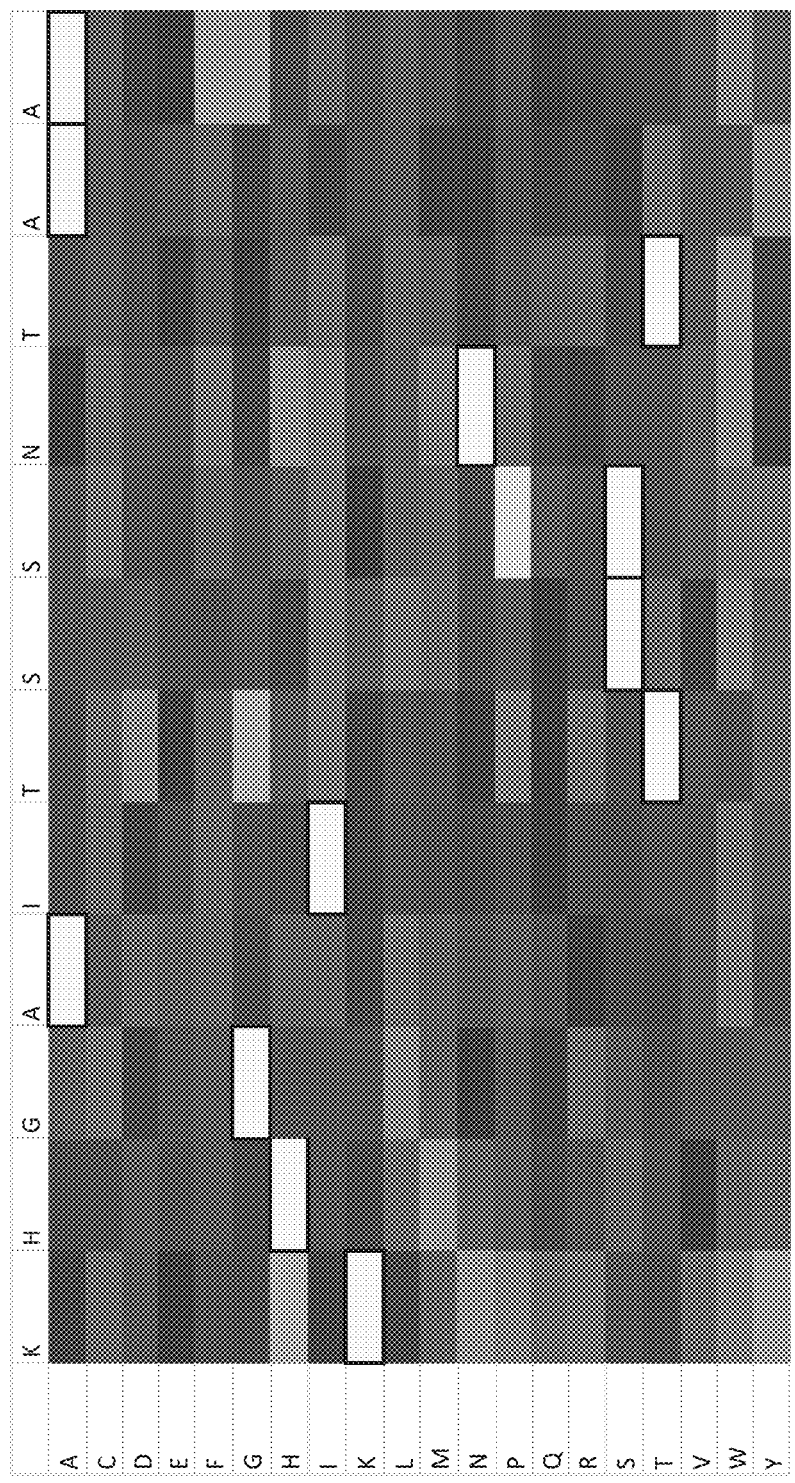
Figure 45D:
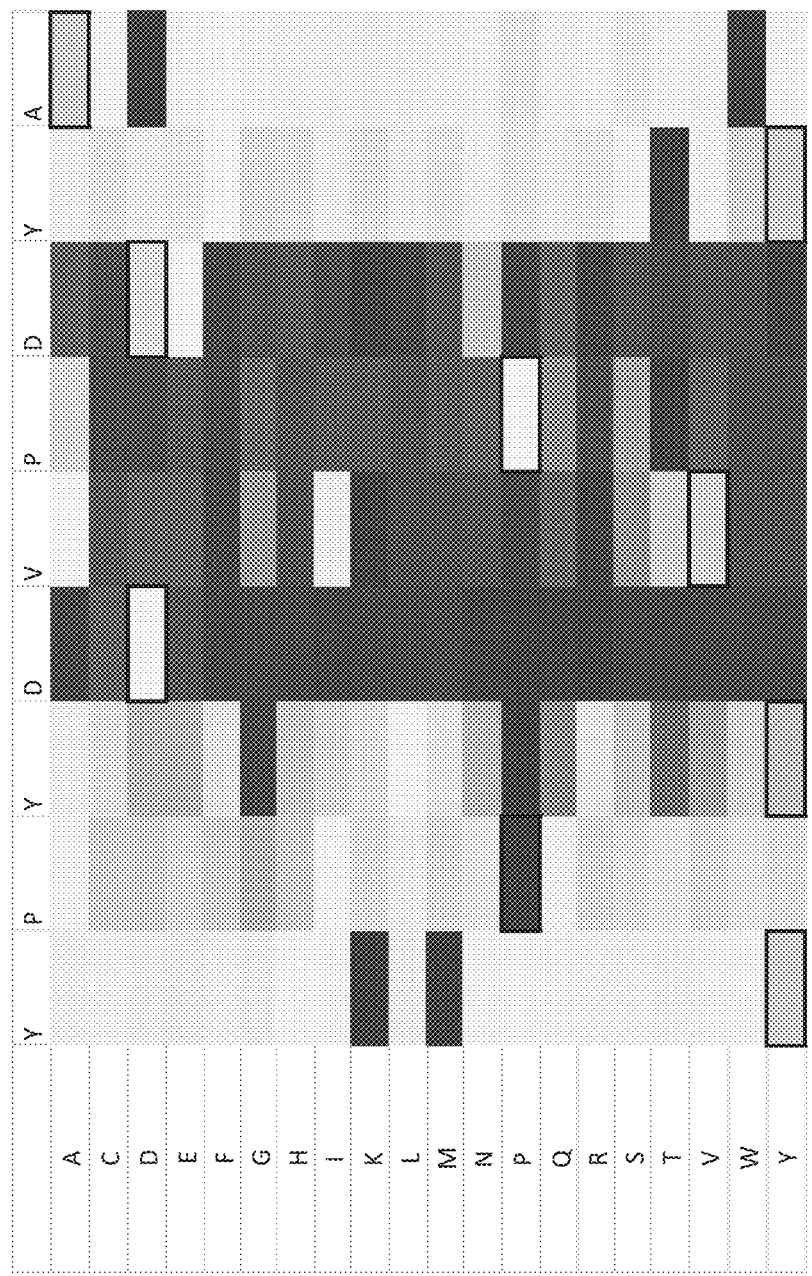
Figure 45E:
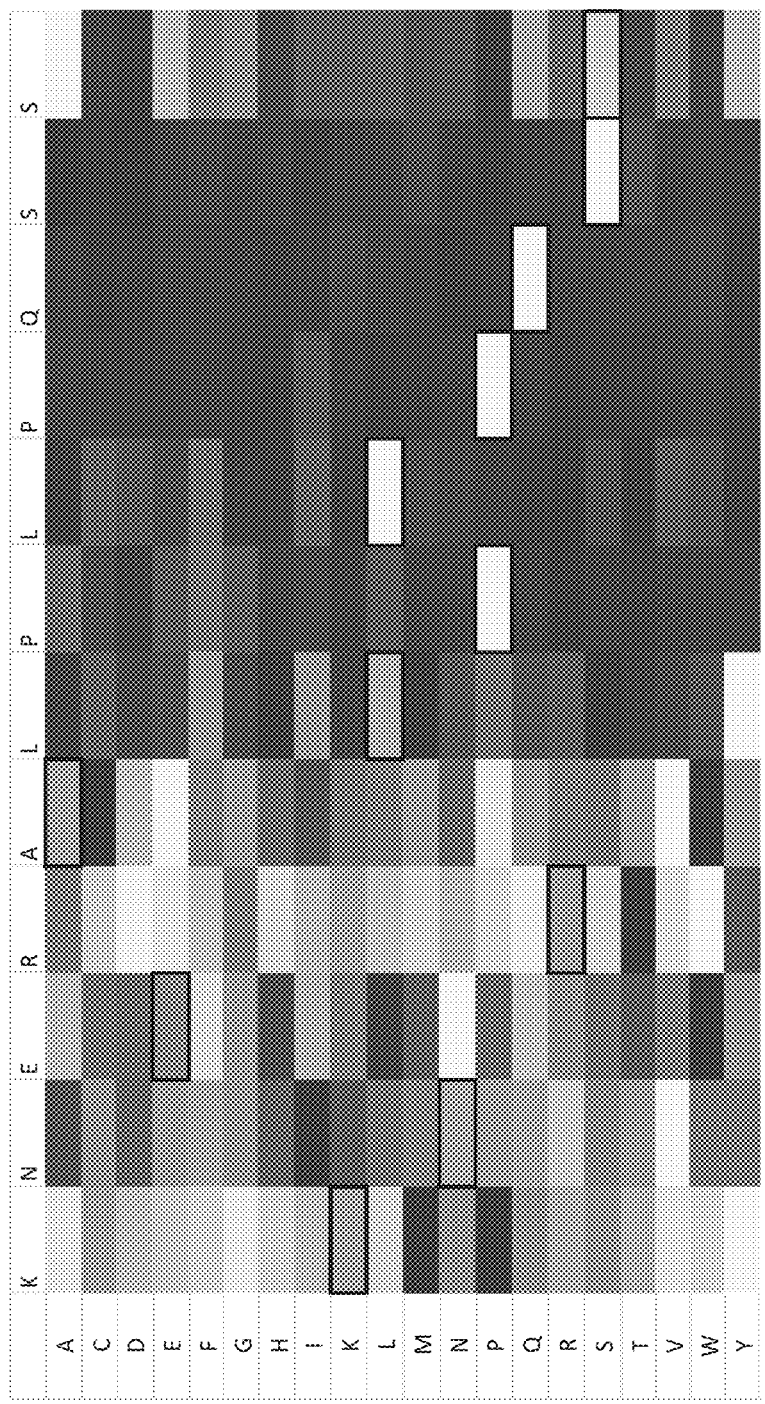
Figure 45F:
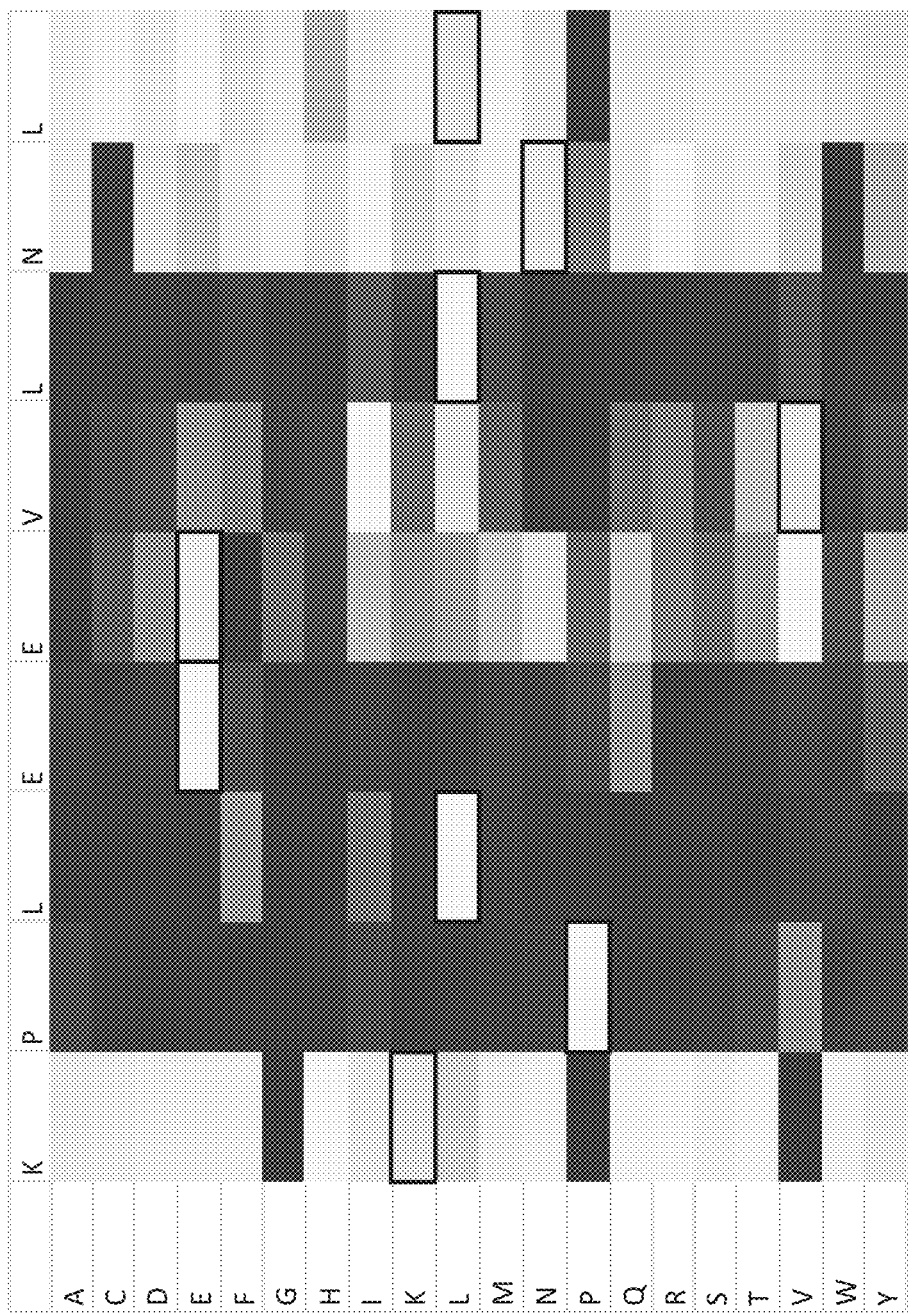
Figure 45G:
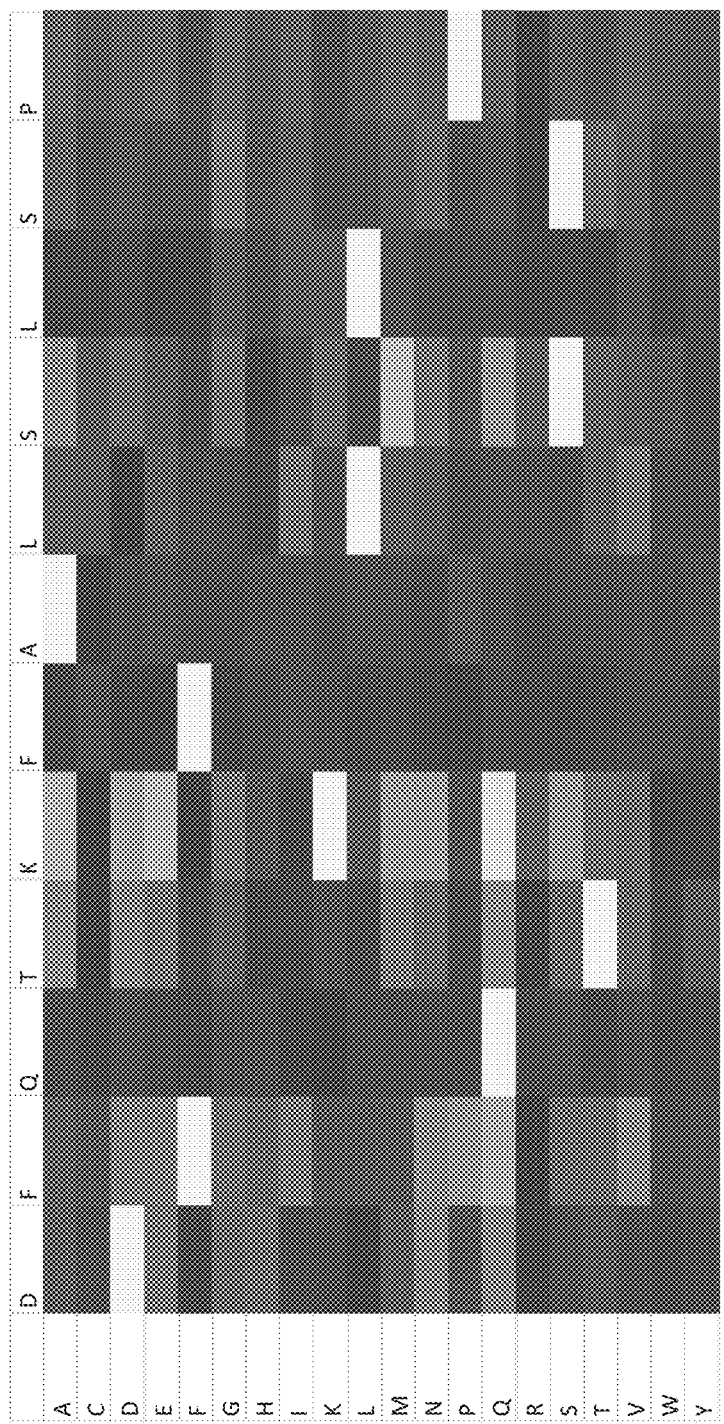
Figure 45H:
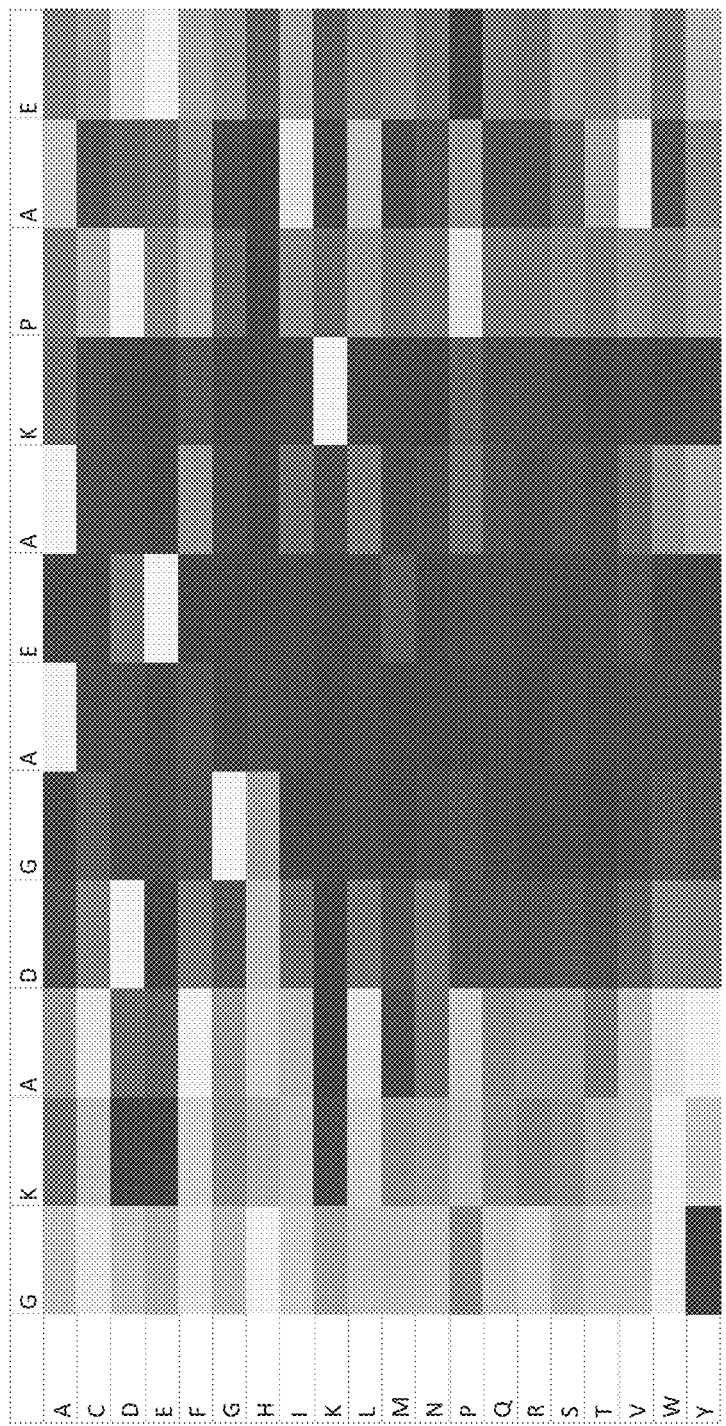
Figure 45I:
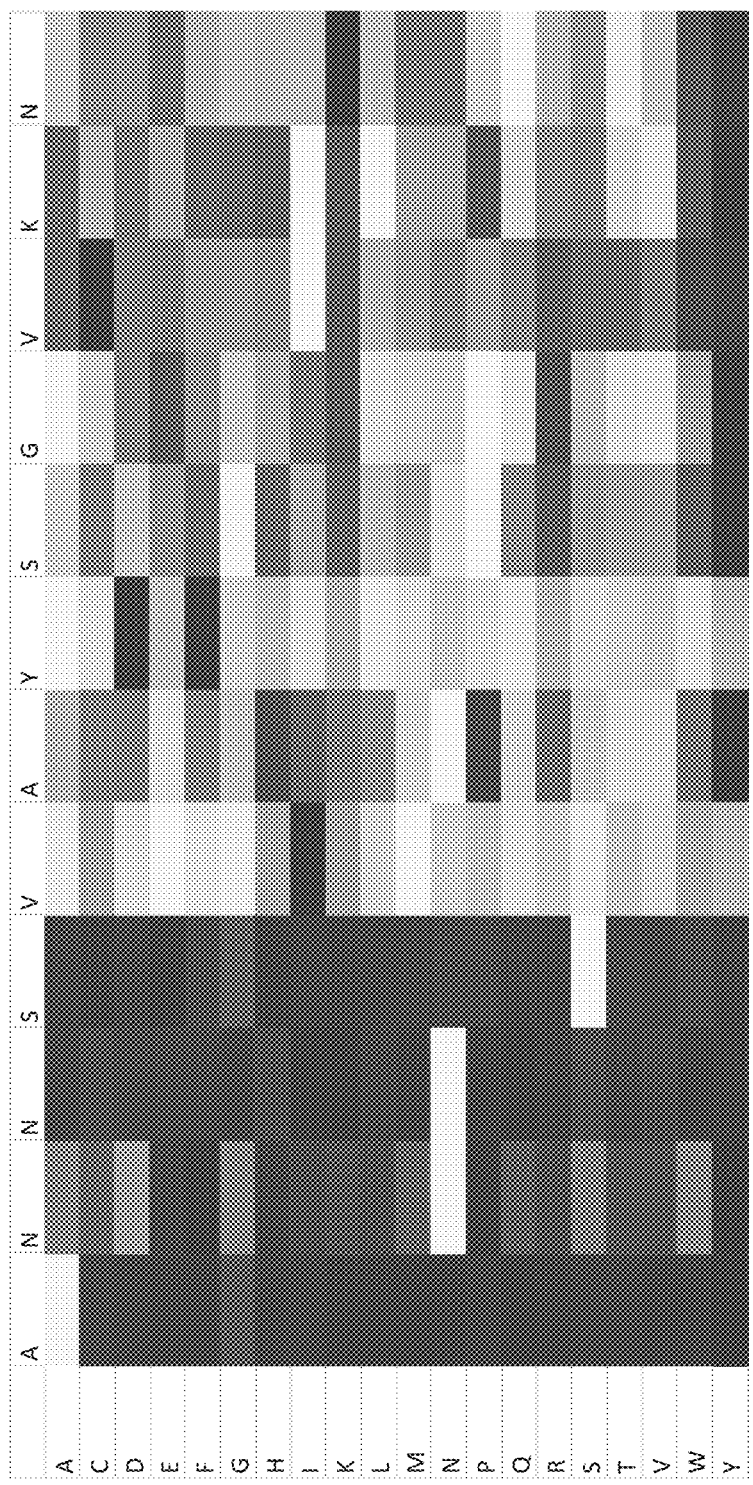
Figure 45J:
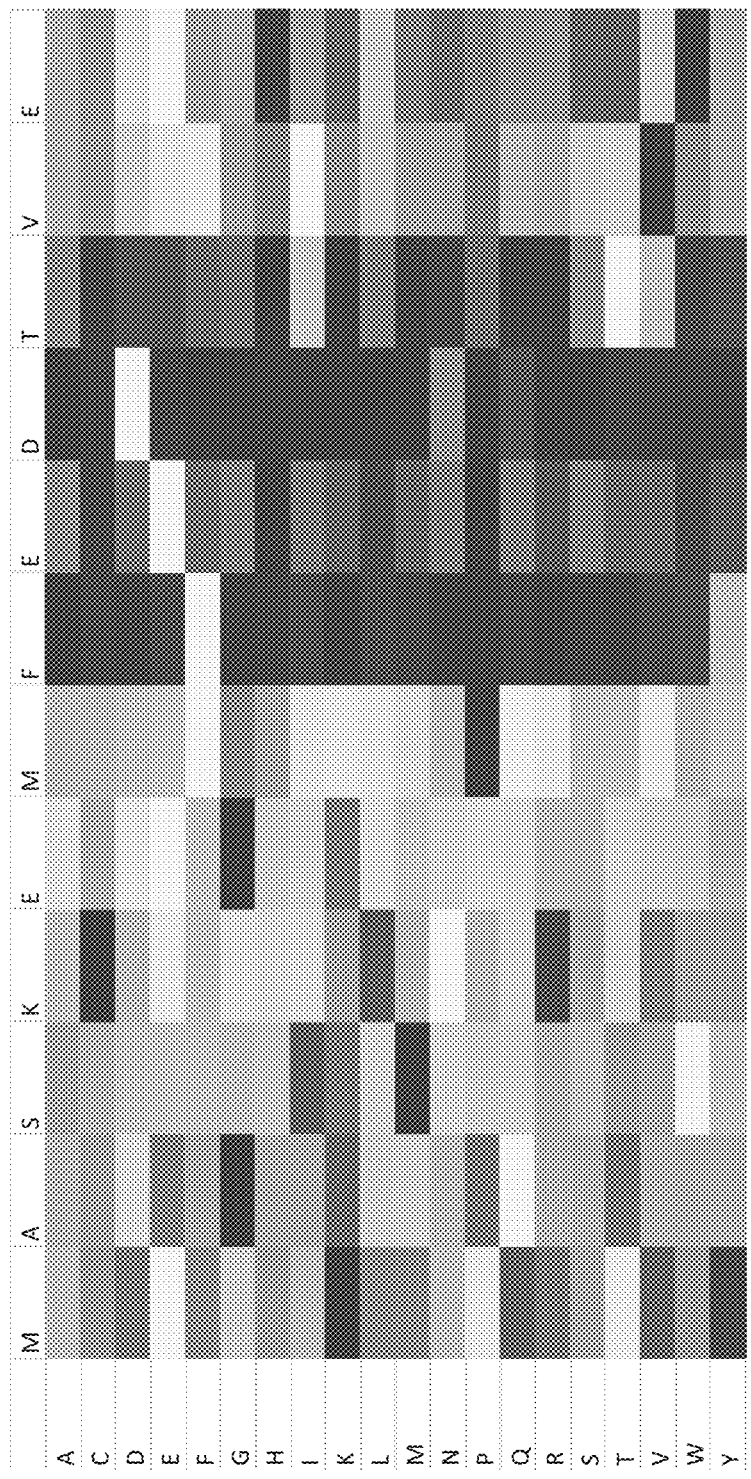
Figure 45K:
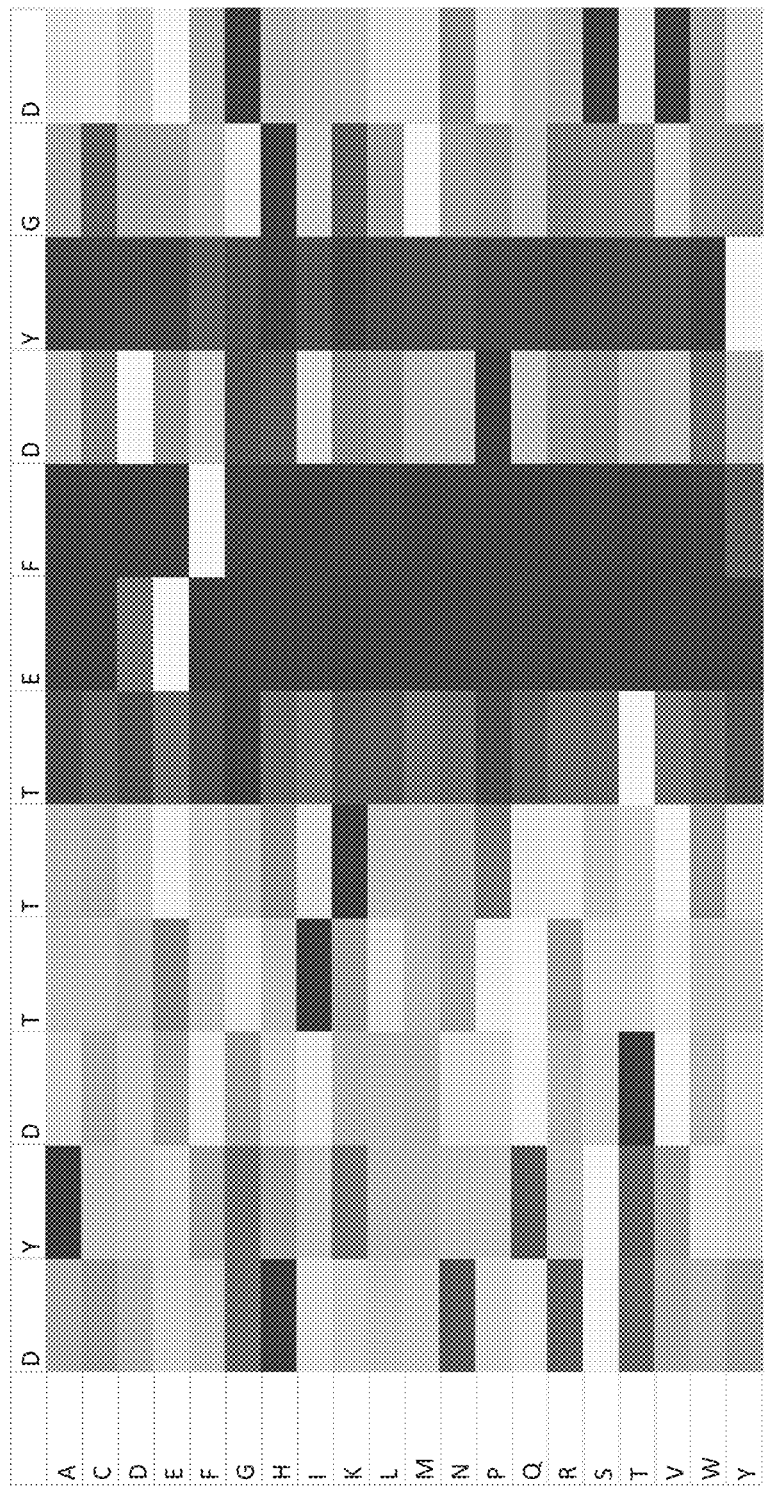

| FIG. 44A | Correct diffusion & overlay pattern |
|---|---|
| FIG. 44B | Incorrect overlay variation in +X direction |
| FIG. 44C | Incorrect overlay variation in +Y direction |
| FIG. 44D | Incorrect diffusion amount variation |

End-of-Line Quality Control

After the completion of processing the wafer in the inline QC monitoring system, end-of-line quality control was performed to further assure high quality of the chip. In this example three end-of-line quality control tests were described with the first one assessing the coupling efficiency, i.e. peptide synthesis, and the last two testing the biological performance of the synthesized peptide.

Quality Control Test 1

For each processing step, there were at least 2 (up to 25) different features which were also exposed using the photomask during the inline QC monitoring system. The amino acid coupling for each feature was measured separately using fluorescein coupled to each feature to determine the coupling efficiency. The results were then compared with a threshold pass criteria for each feature listed in Table 12 to determine the status of each wafer.

TABLE 12

Pass criteria for amino acid coupling

| Amino Acid Name | Fluoroscein Intensity Threshold |
|---|---|
| AA1 | 64125 ± 1000 |
| AA2 | 63500 ± 1000 |
| AA3 | 63000 ± 1000 |
| AA4 | 64520 ± 1000 |
| AA5 | 64185 ± 1000 |

In this example, the results of testing a set of five processed wafers are listed in Table 13 with only one wafer failing in both chip locations. If the wafer passed the threshold intensity criteria for all pre-determined locations, then it was further processed in the next end-of-line quality control step.

TABLE 13

Test results for amino acid coupling

| Wafer # | AA1 | AA2 | AA3 | AA4 | AA5 | Status |
|---|---|---|---|---|---|---|
| | | | Location 1 | | | |
| W1 | 64100 | 63500 | 63125 | 65505 | 65025 | Passed |
| W2 | 64015 | 64000 | 62985 | 65520 | 63456 | Passed |
| W3 | 64155 | 63220 | 62330 | 64985 | 63789 | Passed |
| W4 | 64550 | 63363 | 63890 | 64275 | 64010 | Passed |
| W5 | 62250 | 64055 | 63998 | 63998 | 64185 | Failed AA1 |
| | | | Location 2 | | | |
| W1 | 64120 | 63505 | 63128 | 65525 | 65028 | Passed |
| W2 | 63015 | 64087 | 62980 | 65563 | 63456 | Passed |
| W3 | 64175 | 63202 | 62315 | 64941 | 63777 | Passed |
| W4 | 64520 | 63363 | 63847 | 64212 | 64080 | Passed |
| W5 | 61650 | 64095 | 63900 | 63902 | 64112 | Failed AA1 |

Quality Control Test 2

The next end-of-line quality control step comprised testing the biological performance of particular peptides coupled to the wafer using a set of commercially available monoclonal antibodies. A set of at least 5 (up to 75) different monoclonal antibodies were tested by synthesizing their corresponding antigen peptide sequences on the wafer. The biological performance of the wafer was then tested and compared with the threshold criteria for antibody binding listed in Table 14.

TABLE 14

Pass criteria for antibody binding

| Antibody Name | Intensity |
|---|---|
| CA1 | 64050 ± 1200 |
| CA2 | 55789 ± 1000 |
| CA3 | 64125 ± 1000 |
| CA4 | 60150 ± 1000 |
| CA5 | 62335 ± 1000 |

In this example, the results of testing a set of five processed wafers are listed in Table 15 with only one wafer failing. If the wafer passed both end-of-line quality control test (Test 1 and 2), it was considered of high quality and ready for use.

TABLE 15

Test results for antibody binding

| Wafer # | CA1 | CA2 | CA3 | CA4 | CA5 | Status |
|---|---|---|---|---|---|---|
| W1 | 64020 | 56880 | 64532 | 60985 | 63015 | Passed |
| W2 | 63255 | 55020 | 64789 | 59963 | 61789 | Passed |
| W3 | 63985 | 54996 | 65020 | 60125 | 62785 | Passed |
| W4 | 63785 | 56125 | 63889 | 61002 | 62145 | Passed |
| W5 | 64785 | 50252 | 64025 | 60178 | 62330 | Failed CA2 |

Quality Control Test 3

An additional end-of-line quality control step comprised testing the biological performance of peptides coupled to the wafer by using commercially available antibodies. First, for each commercial antibody it was determined whether a particular amino acid in a peptide sequence is material for binding the antibody. An amino acid was considered material when the biological activity of the corresponding peptide is high if the amino acid is part of the peptide as compared to low when the peptide lacks the amino acid that is replaced by any other amino acid. Various antibody peptide sequences were grown on a chip to determine at least one peptide sequence in which each of the amino acids was material to that peptide for binding a particular antibody.

For example, considering the sequence LKWLDSFTEQ (SEQ ID NO: 1; disclosed in the C-term to N-term orientation), L was replaced one at a time by an amino acid selected from the group consisting of CIT, A, C, D, E, F, G, H, I, K, M, N, P, Q, R, S, T, V, W and Y. Subsequently, the remaining amino acids in the sequence were similarly replaced one at a time. All sequences were then synthesized on the wafer and were tested for biological activity using the commercial antibody for the above sequence.

In this example, goat anti-rabbit IgG, goat anti-mouse IgG and all tested commercial antibodies, including anti-citrulline antibody (ab100932), were obtained from ABCAM. TBS Buffer, PBST Buffer and BSA were obtained from VWR International. In the assay the chips containing all sequences were mounted on a 96-pillar plate and washed with methanol for 5 minutes followed by washing with TBS Buffer for 5 minutes. Primary antibody solution containing PBST and 1% BSA was incubated on the chip at 37° Celsius for 1 hour. The chip was then washed with PBST for 5 minutes thrice, followed by secondary antibody incubation at 37° Celsius for 1 hour, wherein the secondary antibody solution contained PBST, 1% BSA, and the goat anti-rabbit IgG or goat anti-mouse IgG depending on the primary antibody being used. The chip was washed with PBST for 5 minutes thrice, followed by washing with DI water for 5 minutes twice.

FIGS. 45A-K illustrates assay results for the following sequences (the following sequences are all disclosed in the C-term to N-term orientation): LKWLDSFTEQ (SEQ ID NO: 1), DKYYEPHLERA (SEQ ID NO: 2), AATNSSTI-AGHK (SEQ ID NO: 3), AYDPVDYPY (SEQ ID NO: 4), SSQPLPLARENK (SEQ ID NO: 5), LNLVEELPK (SEQ ID NO: 6), PSLSLAFKTQFD (SEQ ID NO: 7), EAPKAE-AGDAKG (SEQ ID NO: 8), NKVGSYAVSNNA (SEQ ID NO: 9), EVTDEFMEKSAM (SEQ ID NO: 10), DGYD-FETTTDYD (SEQ ID NO: 11), respectively (bolded and italicized amino acids were material for antibody binding). For example, from the intensity map shown in FIG. 45A, KWLDS (residues 5-9 SEQ ID NO: 1; disclosed in the C-term to N-term orientation) were the material amino acids for antibody binding in the LKWLDSFTEQ (SEQ ID NO: 1; disclosed in the C-term to N-term orientation) sequence. If any other amino acid was used in place of these amino acids, the sequence did not show any biological activity for antibody binding.

This experiment correlated an amino acid with a particular sequence for which it is a material amino acid. When this particular amino acid was then grown in a layer of the wafer during peptide synthesis, the correlated sequence was also grown as a test sequence in the design to check the coupling yield by evaluating the biological activity of the test sequence.

Figure 46:
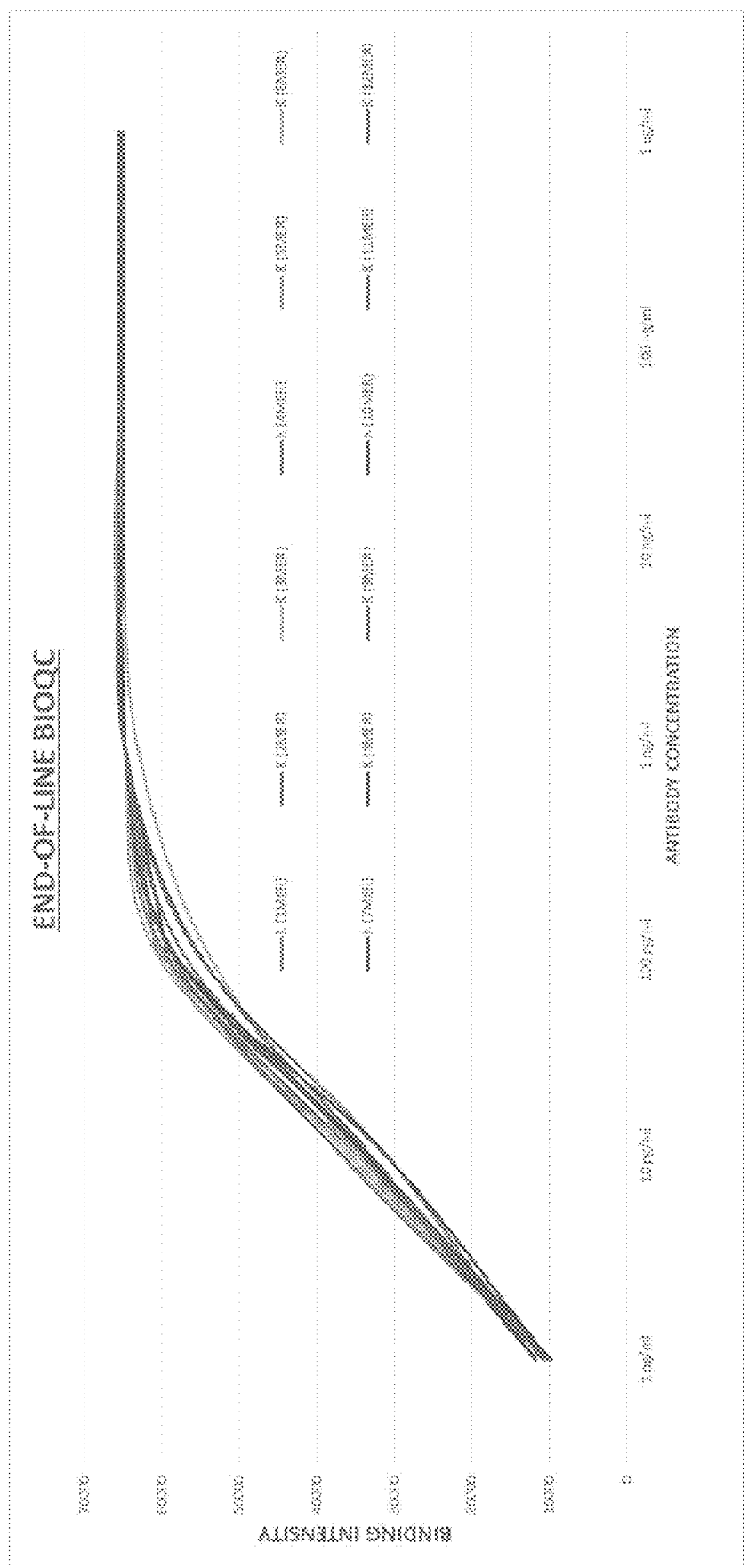
FIG. 46 shows end-of-line BioQC, according to one embodiment.
Figure 47:
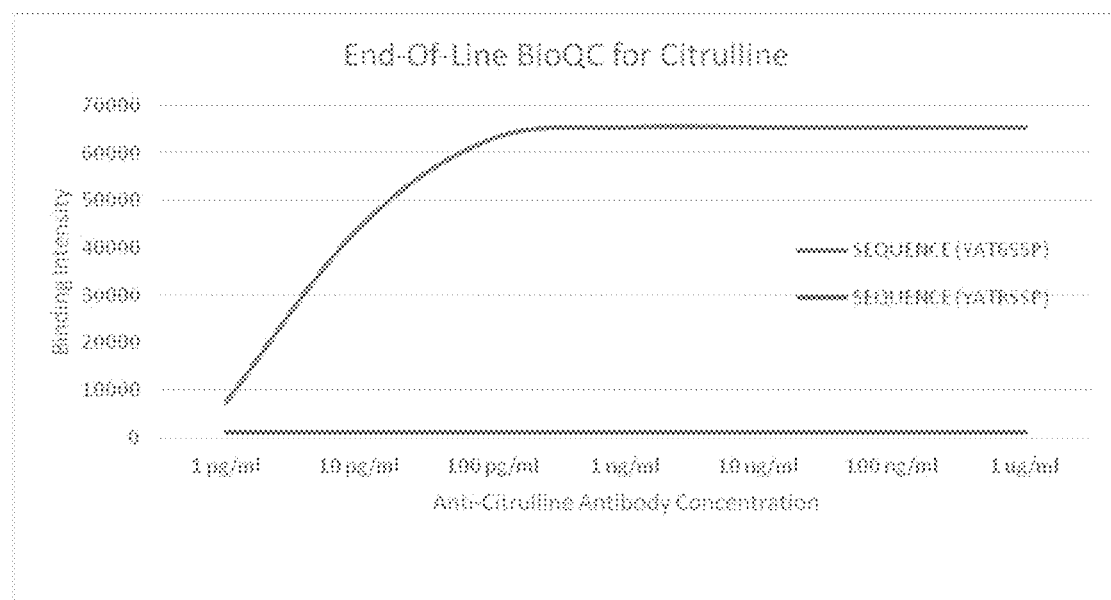
FIG. 47 shows end-of-line BioQC for Citrulline, according to one embodiment. Figure discloses SEQ ID NOS 12 and 13, respectively, in order of appearance.

For example, K was a material amino acid for the sequence LKWLDSFTEQ (SEQ ID NO: 1; disclosed in the C-term to N-term orientation). Thus, whenever K was grown for each layer during the peptide synthesis, there was a corresponding test sequence LKWLDSFTEQ (SEQ ID NO: 1; disclosed in the C-term to N-term orientation) in the design. If 12 layers of K were grown, there were 12 different locations on the wafer at which the corresponding test sequence was grown. FIG. 46 shows the results of binding intensity for the different K polymers employing an assay as described above and varying the anti-p53 antibody concentration.

In another example, biological performance for the amino acid citrulline (CIT) was validated using a sequence containing citrulline (YAT6SSP) (SEQ ID NO: 12) and anti-citrulline antibody that reacted specifically with a peptide containing citrulline irrespective of any other amino acid present sequence. The chips contained both sequences with one that contained citrulline (YAT6SSP) (SEQ ID NO: 12) and the other that lacked citrulline (YATRSSP) (SEQ ID NO: 13) and acted as a mutant sequence. This sequence was grown for each layer for which citrulline was added during the peptide synthesis and biological performance of citrulline was tested for each synthesis step (mer addition) using the anti-citrulline antibody.

In summary, an end-of-line QC monitoring system validated wafers using fluorescein coupling and evaluated biological performance of each amino acid added during the synthesis of a peptide chain on the wafer.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

The invention claimed is:

1. A method of assuring uniformly high quality features that are affixed to a surface of a microarray at positionally-defined locations, comprising:
   a) coating the microarray with a coupling formulation comprising the features;
   b) soft-baking the coated microarray;
   c) determining a thickness of the soft-baked microarray;
   d) stripping off the coat if the thickness of the soft-backed microarray falls outside a first threshold range, and repeating steps (a) through (c);
   e) exposing the soft-baked microarray to light under a photomask;
   f) hard-baking the exposed microarray; and
   g) stripping off the coat if the thickness of the hard-baked microarray falls outside a second threshold range, and repeating steps (a) through (g).

2. The method of claim 1, wherein the photomask comprises a diffusion pattern and an overlay pattern.

3. The method of claim 2, further comprising the steps of
   h) determining a percent deviation of the diffusion pattern or the overlay pattern of the hard-baked microarray as compared to a standard test diffusion or overlay pattern; and
   j) optionally stripping off the coat if the percent deviation of the diffusion pattern or the overlay pattern is greater than 5%;
   and repeating steps (a) through (i).

4. The method of claim 1, wherein the first threshold range is from 2370 nm to 2430 nm.

5. The method of claim 1, wherein the second threshold range is from 790 nm to 810 nm.

6. The method of claim 1, wherein the microarray is soft-baked at a temperature from 75° C. to 115° C.

7. The method of claim 6, wherein the microarray is soft-baked at 85° C.

8. The method of claim 1, wherein the microarray is soft-baked from between 60 seconds to 120 seconds.

9. The method of claim 8, wherein the microarray is soft-baked for 90 seconds.

10. The method of claim 1, wherein the exposing step comprises a light at 248 nm.

11. The method of claim 1, wherein the microarray is hard-baked at a temperature from 75° C. to 115° C.

12. The method of claim 11, wherein the microarray is hard-baked at 85° C.

13. The method of claim 1, wherein the microarray is hard-baked from between 60 seconds to 120 seconds.

14. The method of claim 13, wherein the microarray is hard-baked for 90 seconds.

15. The method of claim 1, wherein the coupling formulation comprises a photoactive compound, a polymer, and a coupling molecule.

16. The method of claim 15, wherein the photoactive compound comprises a photobase.

17. The method of claim 15, wherein the coupling molecule comprises an amino acid.

18. The method of claim 15, wherein the coupling formulation further comprises a coupling reagent and a solvent.

* * * * *

UNITED STATES PATENT AND TRADEMARK OFFICE
CERTIFICATE OF CORRECTION

| | | |
|---|---|---|
| PATENT NO. | : 10,746,732 B2 | Page 1 of 1 |
| APPLICATION NO. | : 15/977951 | |
| DATED | : August 18, 2020 | |
| INVENTOR(S) | : John J. Rajasekaran et al. | |

It is certified that error appears in the above-identified patent and that said Letters Patent is hereby corrected as shown below:

In the Claims

At Column 45, Claim 3, Line 40, delete "j)" and insert --i)--, therefor.

Signed and Sealed this
Seventh Day of September, 2021

Drew Hirshfeld
*Performing the Functions and Duties of the
Under Secretary of Commerce for Intellectual Property and
Director of the United States Patent and Trademark Office*

```
                         SEQUENCE LISTING

<160> NUMBER OF SEQ ID NOS: 11

<210> SEQ ID NO 1
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Gln Glu Thr Phe Ser Asp Leu Trp Lys Leu
1               5                   10

<210> SEQ ID NO 2
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Ala Arg Glu Leu His Pro Glu Tyr Tyr Lys Asp
1               5                   10

<210> SEQ ID NO 3
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Lys His Gly Ala Ile Thr Ser Ser Asn Thr Ala Ala
1               5                   10

<210> SEQ ID NO 4
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Tyr Pro Tyr Asp Val Pro Asp Tyr Ala
1               5

<210> SEQ ID NO 5
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5
```

```
Lys Asn Glu Arg Ala Leu Pro Leu Pro Gln Ser Ser
1               5                   10

<210> SEQ ID NO 6
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Lys Pro Leu Glu Glu Val Leu Asn Leu
1               5

<210> SEQ ID NO 7
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Asp Phe Gln Thr Lys Phe Ala Leu Ser Leu Ser Pro
1               5                   10

<210> SEQ ID NO 8
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Gly Lys Ala Asp Gly Ala Glu Ala Lys Pro Ala Glu
1               5                   10

<210> SEQ ID NO 9
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Ala Asn Asn Ser Val Ala Tyr Ser Gly Val Lys Asn
1               5                   10

<210> SEQ ID NO 10
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Met Ala Ser Lys Glu Met Phe Glu Asp Thr Val Glu
1               5                   10
```

```
-continued

<210> SEQ ID NO 11
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Asp Tyr Asp Thr Thr Thr Glu Phe Asp Tyr Gly Asp
1               5                   10
```